US009771567B2

(12) United States Patent
Wolf et al.

(10) Patent No.: US 9,771,567 B2
(45) Date of Patent: Sep. 26, 2017

(54) KLOTHO VARIANT POLYPEPTIDES

(71) Applicant: TEL HASHOMER MEDICAL RESEARCH INFRASTRUCTURE AND SERVICES LTD., Ramat Gan (IL)

(72) Inventors: Ido Wolf, Or Yehuda (IL); Tamar Rubinek, Or Yehuda (IL)

(73) Assignee: TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 48 days.

(21) Appl. No.: 14/394,465

(22) PCT Filed: Apr. 16, 2013

(86) PCT No.: PCT/IB2013/053001
§ 371 (c)(1),
(2) Date: Oct. 14, 2014

(87) PCT Pub. No.: WO2013/156920
PCT Pub. Date: Oct. 24, 2013

(65) Prior Publication Data
US 2015/0079065 A1 Mar. 19, 2015

Related U.S. Application Data

(60) Provisional application No. 61/624,443, filed on Apr. 16, 2012, provisional application No. 61/752,694, filed on Jan. 15, 2013.

(51) Int. Cl.
| | |
|---|---|
| *C07K 14/47* | (2006.01) |
| *C12N 9/42* | (2006.01) |
| *C07K 14/71* | (2006.01) |
| *C12N 9/24* | (2006.01) |
| *A61K 38/00* | (2006.01) |
| *A61K 48/00* | (2006.01) |

(52) U.S. Cl.
CPC ............ *C12N 9/2434* (2013.01); *C07K 14/71* (2013.01); *C12N 9/24* (2013.01); *C12Y 302/01031* (2013.01); *A61K 38/00* (2013.01); *A61K 48/005* (2013.01)

(58) Field of Classification Search
None
See application file for complete search history.

(56) References Cited

U.S. PATENT DOCUMENTS

| | | | |
|---|---|---|---|
| 6,136,780 A | 10/2000 | Zagon et al. | |
| 6,342,506 B1 | 1/2002 | Giovanella et al. | |
| 6,624,170 B2 | 9/2003 | Giovanella et al. | |
| 6,696,423 B1 | 2/2004 | Barsoum et al. | |
| 6,737,397 B1 | 5/2004 | Zagon et al. | |
| RE39,337 E | 10/2006 | Monosov et al. | |
| 7,268,120 B1 | 9/2007 | Horton et al. | |
| 2010/0330062 A1 | 12/2010 | Koeffler et al. | |

FOREIGN PATENT DOCUMENTS

| | | |
|---|---|---|
| EP | 0945506 B1 | 2/2007 |
| WO | 2004100976 A1 | 11/2004 |

OTHER PUBLICATIONS

Schlachterman et al., Combined Resveratrol, Quercetin, and Catechin Treatment Reduces Breast Tumor Growth in a Nude Mouse Model. Transl Oncol. Mar. 2008;1(1):19-27.
Shiraki-Iida et al., Structure of the mouse klotho gene and its two transcripts encoding membrane and secreted protein. FEBS Lett. Mar. 6, 1998;424(1-2):6-10.
Spector et al., Activation of AMP-activated protein kinase by human EGF receptor 2/EGF receptor tyrosine kinase inhibitor protects cardiac cells. Proc Natl Acad Sci USA Jun. 19, 2007;104(25):10607-10612.
Tachimori et al., Combination Therapy of S-1 with Selective Cyclooxygenase-2 Inhibitor for Liver Metastasis of Colorectal Carcinoma. Anticancer Res. Mar.-Apr. 2008;28(2A):629-638.
Troiani et al., The use of xenograft models for the selection of cancer treatments with the EGFR as an example. Crit Rev Oncol Hematol. Mar. 2008;65(3):200-211.
Tuomela et al., Alendronate decreases orthotopic PC-3 prostate tumor growth and metastasis to prostate-draining lymph nodes in nude mice. BMC Cancer. Mar. 28, 2008;8:81(12 pages).
Urakawa et al., Klotho converts canonical FGF receptor into a specific receptor for FGF23. Nature. Dec. 7, 2006;444 (7120):770-774.
Utsugi et al., Decreased Insulin Production and Increased Insulin Sensitivity in the Klotho Mutant Mouse, a Novel Animal Model for Human Aging. Metabolism. Sep. 2000;49(9):1118-1123.
van Weerden et al., Use of Nude Mouse Xenograft Models in Prostate Cancer Research. Prostate. Jun. 1, 2000;43 (4):263-271.
Wang and Sun, Current understanding of klotho. Ageing Res Rev. Jan. 2009;8(1):43-51.
Wang, Klotho, the Long Sought-After Elixir and a Novel Tumor Suppressor? Cancer Biol Ther. Jan. 2006;5(1):20-21.
Wolf et al., 15-Hydroxyprostaglandin Dehydrogenase is a Tumor Suppressor of Human Breast Cancer. Cancer Res. Aug. 1, 2006;66(15):7818-7823.
Wolf et al., Association between diabetes mellitus and adverse characteristics of breast cancer at presentation. Eur J Cancer. May 2006;42(8):1077-1082.
Wolf et al., FOXA1: Growth inhibitor and a favorable prognostic factor in human breast cancer. Int J Cancer. Mar. 1, 2007;120(5):1013-1022.
Wolf et al., Klotho: a tumor suppressor and a modulator of the IGF-1 and FGF pathways in human breast cancer. Oncogene. Nov. 27, 2008;27(56):7094-7105.

(Continued)

*Primary Examiner* — Christine J Saoud
(74) *Attorney, Agent, or Firm* — Acuity Law Group, PC; Michael A. Whittaker

(57) ABSTRACT

Disclosed are Klotho variant proteins in which residue Glu414 and/or residue Asp238 is substituted with an amino acid different than L-Glu or L-Asp, respectively, as well as polynucleotides encoding the variant proteins, and the use thereof in therapy, especially for the treatment of cancers, especially breast cancer and pancreatic cancer.

2 Claims, 4 Drawing Sheets

(56) References Cited

OTHER PUBLICATIONS

Wu et al., C-terminal Tail of FGF19 Determines its Specificity toward Klotho Co-receptors. J Biol Chem. Nov. 28, 2008;283(48):33304-33309.
Yamamoto et al., Regulation of Oxidative Stress by the Anti-aging Hormone Klotho. J Biol Chem. Nov. 11, 2005;280 (45):38029-38034.
Yee, Targeting insulin-like growth factor pathways. Br J Cancer. Feb. 27, 2006;94(4):465-468.
Zarrabeitia et al., Klotho Gene Polymorphism and Male Bone Mass. Calcif Tissue Int. Jan. 2007;80(1):10-14.
Arap et al., Cancer Treatment by Targeted Drug Delivery to Tumor Vasculature in a Mouse Model. Science. Jan. 16, 1998;279(5349):377-380.
Arking et al., Association of human aging with a functional variant of klotho. Proc Natl Acad Sci USA. Jan. 22, 2002;99(2):856-861.
Arking et al., KLOTHO Allele Status and the Risk of Early-Onset Occult Coronary Artery Disease. Am J Hum Genet. May 2003;72(5):1154-1161.
Bartucci et al., Differential Insulin-like Growth Factor I Receptor Signaling and Function in Estrogen Receptor (ER)-positive MCF-7 and ER-negative MDA-MB-231 Breast Cancer Cells. Cancer Res. Sep. 15, 2001;61(18):6747-6754.
Beck and Reichert, Therapeutic Fc-fusion proteins and peptides as successful alternatives to antibodies. MAbs. Sep.-Oct. 2011;3(5):415-416.
Bergmann et al., Insulin-like Growth Factor I Overexpression in Human Pancreatic Cancer: Evidence for Autocrine and Paracrine Roles. Cancer Res. May 15, 1995;55(10):2007-2011.
Brownstein et al., A translocation causing increased alpha-Klotho level results in hypophosphatemic rickets and hyperparathyroidism. Proc Natl Acad Sci U S A. Mar. 4, 2008;105(9):3455-3460.
Cha et al., Removal of sialic acid involving Klotho causes cell-surface retention of TRPV5 channel via binding to galectin-1. Proc Natl Acad Sci U S A. Jul. 15, 2008;105(28):9805-9810 plus supporting information pp. 1-6.
Chen et al., Insulin stimulates the cleavage and release of the extracellular domain of Klotho by ADAM10 and ADAM17. Proc Natl Acad Sci USA. Dec. 11, 2007;104(50):19796-19801.
Chihara et al., Klotho Protein Promotes Adipocyte Differentiation. Endocrinology. Aug. 2006;147(8):3835-3842.
de Oliveira, Klotho RNAi induces premature senescence of human cells via a p53/p21 dependent pathway. FEBS Lett. Oct. 16, 2006;580(24):5753-5758.
Edderkaoui et al., Insulin-like Growth Factor-I Receptor Mediates the Prosurvival Effect of Fibronectin. J Biol Chem. Sep. 14, 2007;282(37):26646-26655.
El-Shewy et al., The Insulin-like Growth Factor Type 1 and Insulin-like Growth Factor Type 2/Mannose-6-phosphate Receptors Independently Regulate ERK1/2 Activity in HEK293 Cells. J Biol Chem. Sep. 7, 2007;282(36):26150-26157.
Geier et al., Insulin-like Growth Factor-I Inhibits Cell Death Induced by Anticancer Drugs in the MCF-7 Cells: Involvement of Growth Factors in Drug Resistance. Cancer Invest. 1995;13(5):480-486.
Gery et al., Down-Regulation and Growth Inhibitory Role of C/EBPalpha in Breast Cancer. Clin Cancer Res. May 1, 2005;11(9):3184-3190.
Gillet et al., The Development of Gene Therapy: From Monogenic Recessive Disorders to Complex Diseases Such as Cancer. Methods Mol Biol. 2009;542:5-54.
Gomis et al., C/EBPβ at the core of the TGFβ cytostatic response and its evasion in metastatic breast cancer cells. Cancer Cell. Sep. 2006;10(3):203-214.
Gura, Systems for Identifying New Drugs Are Often Faulty. Science. Nov. 7, 1997;278(5340):1041-1042.
Haimsohn et al., Aurintricarboxylic Acid Induces a Distinct Activation of the IGF-I Receptor Signaling within MDA-231 Cells. Endocrinology. Mar. 2002;143(3):837-845.
Haluska et al., In vitro and In vivo Antitumor Effects of the Dual Insulin-Like Growth Factor-I/Insulin Receptor Inhibitor, BMS-554417. Cancer Res. Jan. 1, 2006;66(1):362-371.
Honors and Kinzig, The role of insulin resistance in the development of muscle wasting during cancer cachexia. J Cachexia Sarcopenia Muscle. Mar. 2012;3(1):5-11.
Huang, Regulation of ion channels by secreted Klotho: mechanisms and implications. Kidney Int. May 2010;77 (10):855-860.
Ikushima et al., Anti-apoptotic and anti-senescence effects of Klotho on vascular endothelial cells. Biochem Biophys Res Commun. Jan. 20, 2006;339(3):827-832.
Imura et al., Secreted Klotho protein in sera and CSF: implication for post-translational cleavage in release of Klotho protein from cell membrane. FEBS Lett. May 7, 2004;565(1-3):143-147.
Imura et al., α-Klotho as a Regulator of Calcium Homeostasis. Science. Jun. 15, 2007;316(5831):1615-1618.
International Preliminary Report on Patentability dated Nov. 10, 2009 in corresponding International Application No. PCT/IL2008/000618.
International Search Report dated May 9, 2008 in corresponding International Application No. PCT/IL2008/000618.
Ito et al., Molecular cloning and expression analyses of mouse [beta ]klotho, which encodes a novel Klotho family protein. Mech Dev. Nov. 2000;98(1-2):115-119.
Jonsson et al., Synergistic interactions of combinations of toptecan with standard drugs in primary cultures of human tumor cells from patients. Eur J Clin Pharmacol. Sep. 1998;54(7):509-514.
Karna et al., Serum and tissue level of insulin-like growth factor-I (IGF-I) and IGF-I binding proteins as an index of pancreatitis and pancreatic cancer. Int J Exp Pathol. Oct. 2002;83(5):239-245.
Kato et al., Establishment of the Anti-Klotho Monoclonal Antibodies and Detection of Klotho Protein in Kidneys. Biochem Biophys Res Commun. Jan. 19, 2000;267(2):597-602.
Kim et al., Klotho is a genetic risk factor for ischemic stroke caused by cardioembolism in Korean females. Neurosci Lett. Oct. 30, 2006;407(3):189-194.
Kuro-O et al., Mutation of the mouse klotho gene leads to a syndrome resembling ageing. Nature. Nov. 6, 1997;390(6655):45-51.
Kurosu et al., Regulation of Fibroblast Growth Factor-23 Signaling by Klotho. J Biol Chem. Mar. 10, 2006;281(10):6120-6123.
Kurosu et al., Suppression of Aging in Mice by the Hormone Klotho. Science. Sep. 16, 2005;309(5742):1829-1833 plus supplemental material accessed Dec. 18, 2014:1-16.
Lacroix and Leclercq , Relevance of breast cancer cell lines as models for breast tumours: an update. Breast Cancer Res Treat. Feb. 2004;83(3):249-289.
Li et al., Role of cdk2 in the sequential phosphorylation/activation of C/EBPβ during adipocyte differentiation. Proc Natl Acad Sci USA Jul. 10, 2007;104(28):11597-11602.
Liu et al., Klotho suppresses RIG-I-mediated senescence-associated inflammation. Nat Cell Biol. Mar. 2011;13(3):254-262.
Lorenzi et al., Evidence against a direct role of klotho in insulin resistance. Pflugers Arch. Feb. 2010;459(3):465-473.
Lu et al., Klotho Expression in Epithelial Ovarian Cancer and its Association with Insulin-Like Growth Factors and Disease Progression. Cancer Invest. Mar. 2008;26(2):185-192.
Masiakos et al., Human Ovarian Cancer, Cell Lines, and Primary Ascites Cells Express the Human Mullerian Inhibiting Substance (MIS) Type II Receptor, Bind, and Are Responsive to MIS. Clin Cancer Res. Nov. 1999;5 (11):3488-3499.
Matsumura et al., Identification of the Human Klotho Gene and Its Two Transcripts Encoding Membrane and Secreted Klotho Protein. Biochem Biophys Res Commun. Jan. 26, 1998;242(3):626-630.
McElroy et al., Fluorescent LYVE-1 antibody to image lymphatic trafficking of cancer cells. J Surg Res. Jan. 2009;151(1):68-73.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-230.
Molta, Etanercept in Biologics in General Medicine. Boehncke et al., Springer-Verlag Berlin Heidelberg, 2007; Chap 4:32-41.

(56) References Cited

OTHER PUBLICATIONS

Nabeshima and Imura, α-Klotho: A Regulator That Integrates Calcium Homeostasis. Am J Nephrol. 2008;28(3):455-464.
Noro et al., Gefitinib (IRESSA) sensitive lung cancer cell lines show phosphorylation of Akt without ligand stimulation. BMC Cancer. Dec. 6, 2006;6:277 (12 pages).
Ohyama et al., Molecular Cloning of Rat klotho cDNA: Markedly Decreased Expression of klotho by Acute Inflammatory Stress. Biochem Biophys Res Commun. Oct. 29, 1998;251(3):920-925.
Osterberg and Green, Guidance for Industry and Reviewers: Estimating the Safe Starting Dose in Clinical Trials for Therapeutics in Adult Healthy Volunteers. Federal Register, Jan. 2003;68(11): 1-26 . Accessible on-line at http:/fwww__fda__gov/cder/guidance/index__htm or http:/fwww__fda__gov/ohrms/dockets/defaulthtm.
Ryan et al., Advances in PEGylation of Important Biotech Molecules: Delivery Aspects. Expert Opin Drug Deliv. Apr. 2008;5(4):371-383.
International Search Report and Written Opinion issued in PCT/IB2013/053001 on Aug. 8, 2013.
Wolf et al., "Functional variant of KLOTHO: a breast cancer risk modifier among BRCA1 mutation carriers of Ashkenazi origin", Oncogene, 2010, 29(1):26-33 (Abstract).
Abramovitz et al., "KL1 Internal Repeat Mediates Klotho Tumor Suppressor Activities and Inhibits bFGF and IGF-1 Signaling in Pancreatic Cancer", Clin Cancere Research, 2011, 17(13):4254-66.
Bektas et al., "Klotho gene variation and expression in 20 inbred mouse strains," Mammalian Genome, vol. 15, 759-767 (2004).
Arking et al., "Association Between a Functional Variant of the KLOTHO Gene and High-Density Lipoprotein Cholesterol, Blood Pressure, Stroke, and Longevity," Circulation Research, vol. 96, No. 4, Mar. 4, 2005, pp. 412-418.
Extended European Search Report for application 13777824.7, Mar. 14, 2016.

KLOTHO VARIANT POLYPEPTIDES

RELATED APPLICATION

The present invention is filed under 35 U.S.C. §371 as the U.S. national phase of International Application No. PCT/IB2013/053001, filed Apr. 16, 2013, which designated the U.S. and claims the benefit of priority to U.S. Provisional Patent Application No. 61/624,443 filed Apr. 16, 2012 and to U.S. Provisional Patent Application No. 61/752,694 filed Jan. 15, 2013, which are all hereby incorporated in their entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Oct. 14, 2014, is named GUR0015US_SeqListing.txt and is 392 kilobytes in size.

FIELD AND BACKGROUND OF THE INVENTION

The present invention, in some embodiments, relates to the field of therapeutics, and more specifically to Klotho variant polypeptides, polynucleotides encoding same, and the use thereof in therapy, especially for the treatment of cancer.

Klotho protein is a single-pass transmembrane protein.

Human Klotho protein (SEQ ID NO:1) is 1012 amino acid residues long while murine Klotho protein (SEQ ID NO:81) is 1014 amino acid residues long. All alignment programs confirm a shift of 2 amino acids between the human (1012 amino acids) and mouse (1014 amino acids) Klotho polypeptide sequences. For example, Glu414 in human Klotho protein is the equivalent of Glu416 in mouse Klotho protein and Asp238 in human Klotho protein is Asp240 in mouse Klotho protein.

Klotho protein has been implicated in a number of biological activities including forming a complex with Fibroblast Growth Factor (FGF) receptors and functioning as an obligate co-receptor for FGF23, a bone-derived hormone that induces phosphate excretion into urine. Mice lacking Klotho or FGF23 not only exhibit phosphate retention but also display a premature-aging syndrome, revealing an unexpected link between phosphate metabolism and aging.

Secreted Klotho has been implicated in a number of biological activities including a humoral factor that regulates activity of multiple glycoproteins on the cell surface, including ion channels and growth factor receptors such as Insulin/Insulin-Like Growth Factor-1 receptors.

In US 2010/0330062, the Inventors disclosed that Klotho protein and related compounds have anti-cancer properties and also disclosed the use of Klotho protein and related compounds in the treatment of cancer.

SUMMARY OF THE INVENTION

The invention, in some embodiments thereof, relates to Klotho variant polypeptides as well as to the use of such variant polypeptides as therapeutic agents, especially for the treatment of cancer.

Aspects of some embodiments of the invention relate to the Inventors' discovery that the KL1 domain of Klotho protein bears an active site, and that some of the biological activities of Klotho and of the isolated KL1 can be at least partially neutralized while retaining the anti-cancer activity of the Klotho polypeptide or of the isolated KL1 domain. In some embodiments the neutralization of the biological activities is concomitant with a reduction in adverse side effects.

According to an aspect of some embodiments of the invention, there is provided an isolated polypeptide comprising an amino-acid residue sequence having a omology of not less than 80% with a polypeptide having an amino-acid residue sequence selected from the group consisting of the amino-acid residue sequences represented by: SEQ ID NO:1 (residues 1-1012); residues 29-1012 of SEQ ID NO:1 (SEQ ID NO:2); residues 1-980 of SEQ ID NO:1 (SEQ ID NO:3); residues 29-980 of SEQ ID NO:1 (SEQ ID NO:4); residues 1-568 of SEQ ID NO:1 (SEQ ID NO:5); residues 29-568 of SEQ ID NO:1 (SEQ ID NO:6); residues 34-549 of SEQ ID NO:1 (SEQ ID NO:7); SEQ ID NO:8 (residues 1-549); residues 29-549 of SEQ ID NO:8 (SEQ ID NO:9); and residues 34-549 of SEQ ID NO:8 (SEQ ID NO:10) wherein: the L-Glu of residue 414 is substituted with an a-amino acid residue different from L-Glu having an amino acid sequence set forth in SEQ ID NO:11-20; the L-Asp of residue 238 is substituted with an α-amino acid different from L-Asp having an amino acid sequence set forth in SEQ ID NO:21-30; or the L-Glu of residue 414 is substituted with an α-amino acid residue different from L-Glu and the L-Asp of residue 238 is substituted with an α-amino acid different from L-Asp having an amino acid sequence set forth in SEQ ID NO:31-40, numbered with reference to SEQ ID NO:1.

According to an aspect of some embodiments of the invention, there is also provided the isolated polypeptide, or a DNA encoding therefor, for use in a method of treatment of a disease.

In some embodiments provided is an isolated polynucleotide encoding a Klotho variant polypeptide selected from any one of SEQ ID NO:11-40.

In preferred embodiments the isolated polypeptide has an amino acid sequence set forth in any one of SEQ ID NO:11-40. In some embodiments the isolated polypeptide is a variant of SEQ ID NO:1 wherein the L-Glu at position 414 is substituted with an amino acid other than L-Glu and has an amino acid sequence set forth in any one of SEQ ID NO:11-20. In some embodiments the isolated polypeptide is a variant of SEQ ID NO:1 wherein the L-Asp at position 238 is substituted with an amino acid other than L-Asp and has an amino acid sequence set forth in any one of SEQ ID NO:21-30. In some embodiments the isolated polypeptide is a variant of SEQ ID NO:1 wherein the L-Glu at position 414 is substituted with an amino acid other than L-Glu; wherein the L-Asp at position 238 is substituted with an amino acid other than L-Asp and wherein the polypeptide has an amino acid sequence set forth in any one of SEQ ID NO:31-40.

In some embodiments provided is an isolated polynucleotide encoding a Klotho variant polypeptide having a polynucleotide sequence set forth in any one of SEQ ID NO:51-80.

In preferred embodiments the polynucleotide encoding the isolated polypeptide has a polynucleotide sequence set forth in any one of SEQ ID NO:51-80. In some embodiments the polynucleotide sequence comprises a variant of SEQ ID NO:41 wherein the nucleotides encoding the L-Glu at position 414 encode an amino acid other than L-Glu; and wherein the polynucleotide sequence is set forth in any one of SEQ ID NO:51-60. In some embodiments the polynucleotide sequence comprises a variant of SEQ ID NO:41 wherein the nucleotides encoding the L-Asp at position 238 encode an amino acid other than L-Asp; and wherein the polynucleotide sequence is set forth in any one of SEQ ID NO:61-70. In some embodiments the polynucleotide sequence comprises a variant of SEQ ID NO:41 wherein the nucleotides encoding L-Glu encode an amino acid other than L-Glu; wherein the nucleotides encoding L-Asp at position 238 is substituted encode an amino acid other than L-Asp; and wherein the polynucleotide sequence is set forth in any one of SEQ ID NO:71-80.

In some embodiments provided is an expression vector comprising an isolated polynucleotide encoding a Klotho variant polypeptide having a polynucleotide sequence set forth in any one of SEQ ID NO:51-80.

In some embodiments provided is a composition comprising an expression vector comprising an isolated polynucleotide encoding a variant polypeptide having a polynucleotide sequence set forth in any one of SEQ ID NO:51-80; and a carrier. In preferred embodiments the carrier is a pharmaceutically acceptable carrier.

Further provided is a host cell comprising an expression vector comprising an isolated polynucleotide encoding a variant polypeptide having a polynucleotide sequence set forth in any one of SEQ ID NO:51-80.

In some embodiments the host cell is a prokaryotic cell or a eukaryotic cell. Preferably the cell is a mammalian cell.

According to an aspect of some embodiments of the invention, there is also provided the use of the isolated polypeptide, or a DNA encoding therefor, for the preparation of a medicament for treating a disease.

According to an aspect of some embodiments of the invention, there is also provided the isolated polypeptide, or a DNA encoding therefor, for use as a medicament for treating a disease.

According to an aspect of some embodiments of the invention, there is also provided a method for the treatment of a disease, comprising, administering a pharmaceutically-acceptable effective amount of the isolated polypeptide, or a DNA encoding therefor, to a subject (human or non-human animal) in need thereof.

According to an aspect of some embodiments of the invention, there is also provided a pharmaceutical composition comprising an isolated polypeptide having an amino acid sequence set forth in any one of SEQ ID NO: 11-40; and a pharmaceutically-acceptable carrier.

According to an aspect of some embodiments of the invention, there is also provided a pharmaceutical composition comprising a DNA encoding an isolated polypeptide having an amino acid sequence set forth in any one of SEQ ID NO : 11-40, having a polynucleotide sequence set forth in any one of SEQ ID NO:51-80; and a pharmaceutically-acceptable carrier.

In some embodiments, the disease is cancer.

According to an aspect of some embodiments of the invention, there is also provided an isolated polypeptide comprising a Klotho amino acid sequence and having at least one amino acid mutation in the catalytic domain of Klotho, wherein the isolated polypeptide maintains an anti cancer activity. In some embodiments, the catalytic domain of Klotho is the KL1 domain.

In some embodiments, the amino acid mutation is in at least one amino acid residue corresponding to an amino acid coordinate selected from the group consisting of Glu414 and Asp238 of human Klotho (SEQ ID NO: 1).

In some embodiments, the isolated polypeptide comprises a reduced FGF23 mediated signaling activity as compared to that of human Klotho (SEQ ID NO: 1).

In some embodiments, the isolated polypeptide has a reduced IGF-1 signaling inhibitory activity as compared to that of human Klotho (SEQ ID NO: 1).

In some embodiments, the at least one amino acid mutation is of amino acid residues corresponding to amino acid coordinates Glu414 and Asp238 of human Klotho (SEQ ID NO: 1)

In some embodiments, the amino acid mutation is an amino acid substitution.

In some embodiments, the amino acid substitution is to an amino acid residue selected from the group consisting of a non-charged amino acid, a polar amino acid and a non-polar amino acid residue.

In some embodiments, the amino acid substitution is to a polar amino acid residue.

In some embodiments, the amino acid substitution is selected from the group consisting of Glu414Gln and Asp238Asn.

In some embodiments, the isolated polypeptide is devoid of a domain selected from the group consisting of native signal and KL2.

In some embodiments, the Klotho comprises human Klotho.

In some embodiments, the isolated polypeptide is selected from the group consisting of SEQ ID NO: 11-40.

According to an aspect of some embodiments of the invention, there is also provided an isolated polynucleotide comprising a nucleic acid sequence encoding any of the above polypeptides.

According to an aspect of some embodiments of the invention, there is also provided a nucleic acid construct comprising the nucleic acid sequence.

According to an aspect of some embodiments of the invention, there is also provided a pharmaceutical composition comprising as an active ingredient an isolated polypeptide as described above or the isolated polynucleotide described above or the nucleic acid construct described above and a pharmaceutically acceptable carrier or diluent.

According to an aspect of some embodiments of the invention, there is also provided a cell comprising the nucleic acid construct described above.

According to an aspect of some embodiments of the invention, there is also provided a method of treating cancer comprising administering to a subject in need thereof the pharmaceutical composition described above, thereby treating cancer.

According to an aspect of some embodiments of the invention, there is also provided an isolated polypeptide as described above, an isolated polynucleotide as described above or the nucleic acid construct described above for use in treating cancer, in some embodiments, breast cancer.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "medicament" and "therapeutic agent" are used synonymously.

As used herein, the term "treating" includes curing a condition, treating a condition, preventing a condition, treating symptoms of a condition, curing symptoms of a condition, ameliorating symptoms of a condition, treating effects of a condition, ameliorating effects of a condition, and preventing results of a condition.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

A "polynucleotide" as used herein refers to an oligonucleotide or nucleotide and fragments or portions thereof, and to DNA or RNA of genomic or synthetic origin which may be single- or double-stranded, and represent the sense or antisense strand. Similarly, "polypeptide" as used herein refers to an oligopeptide, peptide, amino acid sequence or protein sequence, and fragments or portions thereof, and to naturally occurring, synthetic or recombinant molecules.

The term "expression vector" and "recombinant expression vector" as used herein refers to a recombinant DNA molecule containing a desired coding sequence and appropriate nucleic acid sequences necessary for the expression of the operably linked coding sequence, i.e., a polynucleotide encoding a Klotho variant polypeptide, in a particular host organism. The expression vector may comprise sequences encoding heterologous domains including but not limited to protein detection, purification or cleavage sequences that may be fused at the N- or C-terminus to the desired coding sequence, to yield a fusion protein.

As used herein, the indefinite articles "a" and "an" mean "at least one" or "one or more" unless the context clearly dictates otherwise.

In some instances, especially in US 61/624,443, the term "protein" is used instead of the intended term "polypeptide". Protein and polypeptide may be used interchangeably.

In some instances, especially in US 61/624,443, the term "mutant Klotho protein" is used instead of the intended "Klotho variant polypeptide". The terms "mutant Klotho protein" "Klotho variant polypeptide" may be used interchangeably.

As used herein, when a numerical value is preceded by the term "about", the term "about" is intended to indicate +/−10%.

BRIEF DESCRIPTION OF THE FIGURES

Some embodiments of the invention are herein described, by way of example only, with reference to the accompanying figures. The description, together with the figures, makes apparent how embodiments of the invention may be practiced to those skilled in the art. It is stressed that the particulars shown in the figures are by way of example and for purposes of illustrative discussion of embodiments of the invention.

In the figures.

DESCRIPTION OF SOME EMBODIMENTS OF THE INVENTION

Figure 1A:
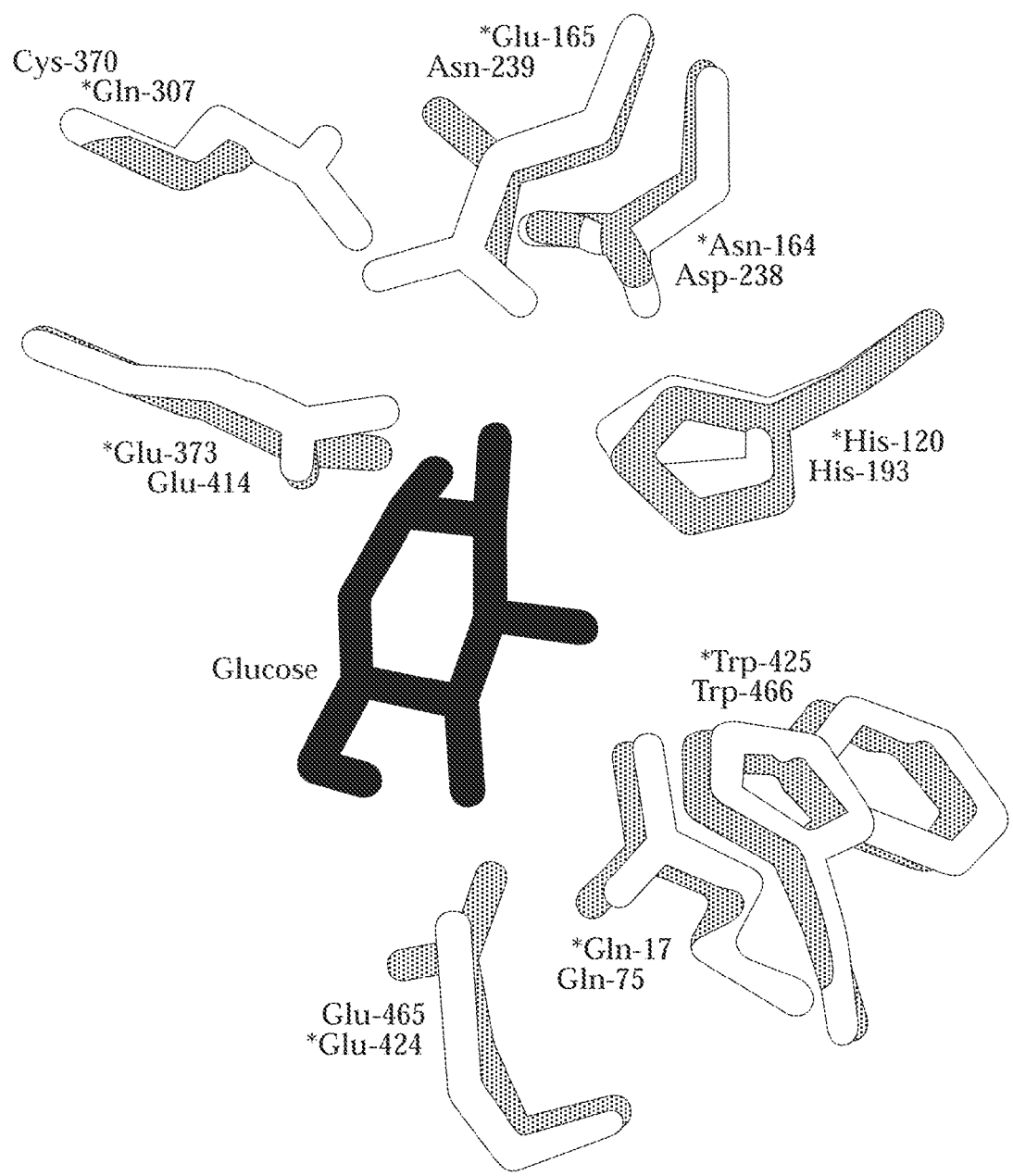
FIG. 1A schematically depicts portions of KLrP (klotho-related protein) surrounding a glucose molecule, on which portions of native Klotho protein KL1 domain is superimposed, demonstrating the similarity of the respective active sites.

The invention, in some embodiments thereof, relates to Klotho polypeptides as well as to the use of such polypeptides as therapeutic agents, especially for the treatment of cancer.

Klotho protein is a single pass transmembrane protein located at the cell membrane (Ito et al., 2000; Kuro-o et al., 1997; Matsumura et al., 1998; Shiraki-Iida et al., 1998) and also detected in the Golgi apparatus (Imura et al., 2007). Human Klotho protein (full-length (FL)-hKL; SEQ ID NO:1, accession no. AAQ41828) is 1012 amino acid residues long while murine Klotho protein (full-length (FL)-mKL; SEQ ID NO:81, accession no AAQ41830) is 1014 amino acid residues long. The N-terminus of human Klotho protein (residues 1-28) trails from KL1. Human Klotho protein is anchored in a cell membrane through the C-terminus (residues 981-1012).

The extracellular domain of Klotho protein is composed of two spherically-folded discrete domains, KL1 (human residues 29-568, 540 residues long) and KL2 (human residues 569-980, 411 residues long), which share amino acid sequence homology to β-glucosidase but lack glucosidase catalytic activity (Kuro-o et al., 1997). KL1 may also be transcribed through an alternative splicing. It is known that in vivo, KL1-KL2 can be cleaved together to form a single 130 kDa secreted Klotho protein, also called soluble Klotho protein, (sol-hKL or sol-mKL, residues 1-980, also called secreted Klotho protein) which is shed into the serum and acts as a circulating hormone (Imura et al., 2004), or can be cleaved separately as a 68 kDa protein (KL1) and a 64 kDa protein (KL2). It has been shown recently that A Desintegrin and Metalloproteinase (ADAM) 10 and 17 participate in this process in response to insulin stimulation (Chen et al., 2007). Only full length Klotho can function as a co-receptor for FGF23 (Kurosu et al., 2006; Wu et al., 2008).

Soluble Klotho protein has been implicated in a number of biological activities including a humoral factor that regulates activity of multiple glycoproteins on the cell surface including ion channels and growth factor receptors such as insulin/insulin-like growth factor-1 receptors.

mRNA expression analysis identified Klotho protein mainly in the distal renal tubules and the choroid plexus in the brain, but also in sex-hormone-responsive tissues including the placenta, testes and ovaries (Kuro-o et al., 1997; Ohyama et al., 1998; Shiraki-Iida et al., 1998). The expression of Klotho protein in breast or pancreatic tissue has been explored by the Inventors and disclosed in US 2010/0330062.

Klotho protein-modulated receptors include the insulin receptor (IR) (Kuro-o et al., 1997), the IGF-1 receptor (IGF-1R) and several fibroblast growth factor receptors (FGFR), but not the epidermal growth factor receptor (EGFR) (Kurosu et al., 2006; Urakawa et al., 2006). Treatment of cultured cells with soluble Klotho protein inhibited insulin-induced glucose uptake, and reduced stimulation-induced phosphorylation of the IR, the IGF-1R and the insulin receptor substrates (IRS)-1 and -2 (Kurosu et al., 2005). Moreover, Klotho protein-deficient mice are hypoglycemic and extremely sensitive to insulin (Kuro-o et al., 1997; Utsugi et al., 2000), while Klotho protein overexpressing mice are associated with insulin resistance (Kurosu et al., 2005). Klotho protein also functions as an obligate co-receptor for FGF23, a bone-derived hormone that induces phosphate excretion into urine. Mice lacking Klotho protein, and/or FGF23 not only exhibit phosphate retention but also display a premature-aging syndrome, revealing an unexpected link between phosphate metabolism and aging. Klotho protein inhibits activation of the FGFRs by bFGF in human embryonic kidney (HEK) 293 and COS7 cells (Wolf et al., 2008; Urakawa et al., 2006; Kurosu et al., 2006).

Klotho protein-induced inhibition of the IGF-1R may also affect the expression of the transcription factors CCAAT/enhancer-binding protein (C/EBP) α and β. These factors are down-regulated by the IGF-1 pathway and were recently identified as breast cancer growth suppressors (Gery et al., 2005; Gomis et al., 2006; Wolf et al., 2006a). The C/EBP family is involved in adipocyte differentiation and Klotho protein-deficient mice have barely detectable amounts of white adipose tissue (Kuro-o et al., 1997). Indeed, Klotho protein has been identified recently as an inducer of adipocyte differentiation, and this activity is mediated through up-regulation of these transcription factors (Chihara et al., 2006).

Klotho protein may play a role in human diseases, and Klotho protein polymorphism was associated with reduced life span, coronary heart disease and osteoporosis (Arking et al., 2003; Arking et al., 2002; Kim et al., 2006; Zarrabeitia et al., 2007).

Klotho protein has been shown to affect the activity of several signaling pathways, which may participate in breast cancer tumorigenesis, through modulation of ligand-dependent activation of their specific membranal receptors. Increased serum insulin levels are associated with adverse prognosis in breast cancer, high circulating IGF-1 levels are associated with increased risk of premenopausal breast cancer, and inhibition of the insulin and IGF-1 pathways inhibits growth of breast cancer cells (Bartucci et al., 2001; Wolf et al., 2006b; Yee, 2006).

In US2010/0330062 the Inventors identified high Klotho protein expression in normal breast tissue and low Klotho protein expression in breast cancer; noted inhibition of breast cancer cell growth following over-expression of Klotho protein, and growth enhancement of Klotho protein-expressing cells following Klotho protein knock-down; and revealed modulation of the IGF-1 and the insulin pathways by Klotho protein. Taken together, the results suggested Klotho protein as a novel breast cancer tumor suppressor.

Insulin like growth factor-1 (IGF-1) is also a powerful mediator of pancreatic cancer. Both IGF-1 and IGF-1 receptor (IGF-1R) are overexpressed in human pancreatic tumors as well as in pancreatic cancer cell lines (Bergmann, U., et al, 1995, Karna, E., et al, 2002). Blockage of the IGF-1R by a dominant negative inhibitor suppresses tumorigenicity both in vitro and in vivo and increases sensitivity of pancreatic tumors to radiation and chemotherapy-induced apoptosis (Edderkaoui, M., et al, 2007). Thus, the inventors consider that the IGF-1 pathway may serve as an attractive target for novel therapies against pancreatic cancer.

Klotho protein has previously been identified as an inhibitor of the IGF-1 system in hepatocytes and muscle cells. The effects of Klotho protein on inhibition of the IGF-1 system in cancer cells, such as pancreatic and breast cancer cells, have not hitherto been studied.

The appended sequence listing includes polypeptide and polynucleotide sequences encoding the polypeptides, as set forth in Table 1, infra, in the Examples.

The normal polypeptide and DNA sequences, specifically SEQ ID NO:1, 8, 41, 48 and 81-84 are fully described in PCT/JP1997/004585 published as WO1998029544.

The Inventors have since discovered and now report that some of the biological activity of human Klotho protein (e.g., formation of a complex with FGF receptors to activate FGF23 in the kidney and modulation of calcium levels in the body of an organism) is at least partially dependent on the presence of at least one of two specific amino acid residues in the KL1 domain of Klotho protein: the L-Glu of residue 414 and the L-Asp of residue 238.

The Inventors have further discovered that replacing either one or both of these amino acid residues with a different α-amino acid residue to yield a novel variant polypeptide according to some embodiments of the invention, does not necessarily adversely affect the anti-cancer activity of the polypeptide. Importantly, the Inventors have now further discovered that the IGF1 receptor activity of variant polypeptides according to some embodiments of the invention where either one or both of these amino acid residues has been replaced with a different α-amino acid residue is reduced or neutralized, indicating that the anti-cancer mechanism of the variants and of native Klotho is unrelated to IGF1 signaling. Therefore, the Klotho variant polypeptides in accordance with the teachings herein may serve as better candidates for therapeutic use than either full length native Klotho or KL1.

The Inventors conclude and hereby disclose that at least some polypeptides as described herein, Klotho variant polypeptides in which residue 414 and/or residue 238 is substituted with any α-amino acid different from the native L-Glu or L-Asp respectively, are not only novel, but are unexpectedly useful as therapeutic agents, especially as therapeutic agents for the treatment of cancer. Specifically, some embodiments of such polypeptides are effective therapeutic agents, yet have reduced side-effects due to the at least partial neutralization of the native biological activity affected by substitution of the native residue 414 and/or residue 238.

According to an aspect of some embodiments of the teachings herein, there is provided an isolated polypeptide comprising an amino-acid residue sequence having a homology of not less than 80% with a polypeptide having an amino-acid residue sequence selected from the group consisting of the amino-acid residue sequences represented by:

SEQ ID NO:1 (full length human Klotho protein, FL-hKL, accession no. AAQ41828);

residues 29-1012 of SEQ ID NO:1 (human Klotho protein without the N-terminal "tail");

residues 1-980 of SEQ ID NO:1 (soluble human Klotho protein, sol-hKL);

residues 29-980 of SEQ ID NO:1 (sol-hKL without the N-terminal tail);

residues 1-568 of SEQ ID NO:1 (KL1 with N-terminal tail of human Klotho protein);

residues 29-568 of SEQ ID NO:1 (KL1 of human Klotho protein);

residues 34-549 of SEQ ID NO:1 (a shortened KL1 of human Klotho protein);

SEQ ID NO:8 (the recombinant version of KL1, with additional residues 1-33, accession no. AAQ41829);

residues 29-549 of SEQ ID NO:8 (the recombinant version of KL1, with additional residues 29-33);

residues 34-549 of SEQ ID NO:8 (a recombinant version of KL1, commercially available from Peprotech, Rocky Hill, N.J., USA)

wherein:

the L-Glu of residue 414 is substituted with an α-amino acid residue different from L-Glu;

the L-Asp of residue 238 is substituted with an α-amino acid different from L-Asp; or the L-Glu of residue 414 is substituted with an α-amino acid residue different from L-Glu and the L-Asp of residue 238 is substituted with an α-amino acid different from L-Asp numbered with reference to SEQ ID NO:1.

As used herein the "klotho gene" refers to the Klotho polypeptide coding sequence open reading frame, as shown in (SEQ ID NO:41), or any homologous sequence thereof preferably having at least 70% identity, more preferable 80% identity, even more preferably 90% or 95% identity. This encompasses sequences derived from SEQ ID NO:41 which have undergone mutations, alterations or modifications as described herein. Thus, in a preferred embodiment Klotho polypeptide is encoded by a nucleic acid sequence according to SEQ. ID. NO. 41. It is also to be acknowledged that based on the amino acid sequence of Klotho polypeptide (SEQ ID NO:1) or variants described herein, any nucleic acid sequence coding for such amino acid sequence can be perceived by the one skilled in the art based on the genetic code.

"Klotho polypeptide" and "KL1" refer to the polypeptides of the Klotho gene and KL1 domain of the Klotho gene respectively, and is understood to include splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the Klotho or KL1 coding sequence, such as, inter alia, point mutations, substitutions, deletions and insertions which may cause a difference in a few amino acids between the resultant polypeptide and the naturally occurring Klotho polypeptide. Polypeptides encoded by nucleic acid sequences which bind to the Klotho coding sequence or genomic sequence under conditions of highly stringent hybridization, which are well-known in the art are also encompassed by this term. Chemically-modified Klotho polypeptide or chemically-modified fragments of Klotho polypeptide are also included in the term, so long as the biological activity is retained. Human Klotho polypeptide preferably has or comprises an amino acid sequence, amino acids 1-1012, according to SEQ I. NO:1. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids disclosed herein. Particular fragments of the human Klotho polypeptide include amino acid residues 29-1012 (SEQ ID NO:2), 1-980 (SEQ ID NO:3), 29-980 (SEQ ID NO:4), 1-568 (SEQ ID NO:5), 29-568 (SEQ ID NO:6) and 34-549 (SEQ ID NO:7). Particular fragments of Human KL1 (SEQ ID NO:8, residues 1-549) include amino acid residues 29-549 (SEQ ID NO:9) and 34-549 (SEQ ID NO:10).

A "variant polypeptide" is a polypeptide having one or more sequence substitutions, deletions, and/or additions as compared to the native sequence. The variants disclosed herein are artificially constructed; typically generated from the corresponding nucleic acid molecules. In preferred embodiments, the variants have 1 or 2 amino acid substitutions and retain at least some of the activity of the native polypeptide. In some embodiments the variants disclosed herein retain at least part of the anti-cancer activity of the native Klotho polypeptide and elicit reduced side effects. This unexpected property of the Klotho variant polypeptides disclosed herein warrants their use as therapeutic agents for the treatment of cancer.

In some embodiments, the isolated polypeptide has an amino acid sequence represented by SEQ ID NO:1 (full length human Klotho protein, FL-hKL), wherein:

the L-Glu of residue 414 is substituted with an α-amino acid different from L-Glu;

the L-Asp of residue 238 is substituted with an α-amino acid different from L-Asp; or the L-Glu of residue 414 is substituted with an α-amino acid residue different from L-Glu and the L-Asp of residue 238 is substituted with an α-amino acid different from L-Asp numbered with reference to SEQ ID NO:1.

In some embodiments, the isolated polypeptide has an amino acid sequence represented by residues 29-1012 of SEQ ID NO:1 (set forth in SEQ ID NO:2) human Klotho protein without the N-terminal "tail"), wherein:

the L-Glu of residue 414 is substituted with an α-amino acid different from L-Glu;

the L-Asp of residue 238 is substituted with an α-amino acid different from L-Asp; or the L-Glu of residue 414 is substituted with an α-amino acid residue different from L-Glu and the L-Asp of residue 238 is substituted with an α-amino acid different from L-Asp numbered with reference to SEQ ID NO:1.

In some embodiments, the isolated polypeptide has an amino acid sequence represented by residues 1-980 of SEQ ID NO:1 (set forth in SEQ ID NO:3) soluble human Klotho protein, sol-hKL), wherein:

the L-Glu of residue 414 is substituted with an α-amino acid different from L-Glu;

the L-Asp of residue 238 is substituted with an α-amino acid different from L-Asp;
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 29-980 of SEQ ID NO:1 (set forth in SEQ ID NO:4) sol-hKL without the N-terminal tail), wherein:
the L-Glu of residue 414 is substituted with an α-amino acid different from L-Glu;
the L-Asp of residue 238 is substituted with an α-amino acid different from L-Asp; or
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 1-568 of SEQ ID NO:1 (set forth in SEQ ID NO:5) KL1 with N-terminal tail of human Klotho protein), wherein:
the L-Glu of residue 414 is substituted with an α-amino acid different from L-Glu;
the L-Asp of residue 238 is substituted with an α-amino acid different from L-Asp; or
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 29-568 of SEQ ID NO:1 (set forth in SEQ ID NO:6) KL1 of human Klotho protein), wherein:
the L-Glu of residue 414 is substituted with an α-amino acid different from L-Glu;
the L-Asp of residue 238 is substituted with an α-amino acid different from L-Asp; or
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 34-549 of SEQ ID NO:1 (set forth in SEQ ID NO:7) a shortened KL1 of human Klotho protein), wherein:
the L-Glu of residue 414 is substituted with an α-amino acid different from L-Glu;
the L-Asp of residue 238 is substituted with an α-amino acid different from L-Asp; or
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 34 to 549 of SEQ ID NO:8 (set forth in SEQ ID NO:10) the recombinant version of KL1, wherein:
the L-Glu of residue 414 is substituted with an α-amino acid different from L-Glu;
the L-Asp of residue 238 is substituted with an α-amino acid different from L-Asp;
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by SEQ ID NO:8 (the recombinant version of KL1, with additional residues 1-33), wherein:
the L-Glu of residue 414 is substituted with an α-amino acid different from L-Glu;
the L-Asp of residue 238 is substituted with an α-amino acid different from L-Asp; or
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the isolated polypeptide has an amino acid sequence represented by residues 29 to 549 of SEQ ID NO:8 (set forth in SEQ ID NO:9) the recombinant version of KL1, with additional residues 29-33, wherein:
the L-Glu of residue 414 is substituted with an α-amino acid different from L-Glu;
the L-Asp of residue 238 is substituted with an α-amino acid different from L-Asp;
the L-Glu of residue 414 is substituted with an α-amino acid residue different from L-Glu and
the L-Asp of residue 238 is substituted with an α-amino acid different from L-Asp numbered with reference to SEQ ID NO:1.

In some embodiments, the L-Glu of residue 414 is substituted with an α-amino acid residue different from L-Glu.

In some embodiments, the L-Glu of residue 414 is substituted with an R-α-amino acid residue. In some such embodiments, the R-α-amino acid residue is R-Glu. In some embodiments, the R-α-amino acid residue is different from R-Glu.

In some embodiments, the L-Glu of residue 414 is substituted with an L-α-amino acid residue different from L-Glu. In some such embodiments, the L-α-amino acid residue is selected from the group consisting of Ala, Arg, Asn, Asp, Cys, Gln, Gly, His, Ile, Leu, Lys, Met, Phe, Pro, Ser, Thr, Trp, Tyr, Val, ornithine, selenocysteine (Sec), 2-aminoisobutyric acid, hydroxyproline (Hyp) and selenomethionine.

In some embodiments, the L-Glu of residue 414 is substituted with an α-amino acid residue that is devoid of an acid side chain.

In some embodiments, the L-Glu of residue 414 is substituted with an L-α-Gln. An advantage of such embodiments is that L-α-Gln is devoid of the acid group required for L-Glu activity and is of substantially the same size and shape as the native L-α-Gln, so that the change in shape of the polypeptide caused by the substitution is minimal.

In some embodiments, the L-Asp of residue 238 is substituted with an α-amino acid residue different from L-Asp.

In some embodiments, the L-Asp of residue 238 is substituted with an R-α-amino acid residue. In some such embodiments, the R-α-amino acid residue is R-Asp. In some such embodiments, the R-α-amino acid residue is different from R-Asp.

In some embodiments, the L-Asp of residue 238 is substituted with an L-α-amino acid residue different from L-Asp. In some such embodiments, the L-α-amino acid residue is selected from the group consisting of Ala, Arg, Asn, Cys, Gln, Glu, Gly, His, Ile, Leu, Lys, Met, Phe, Pro, Ser, Thr, Trp, Tyr, Val, ornithine, selenocysteine (Sec), 2-aminoisobutyric acid, hydroxyproline (Hyp) and selenomethionine.

In some embodiments, the L-Asp of residue 238 is substituted with an α-amino acid residue that is devoid of an acid side chain.

In some embodiments, the L-Asp of residue 238 is substituted with an L-α-Asn. An advantage of such embodiments is that L-α-Asn is devoid of the acid group required for L-Asp activity and is of substantially the same size and shape as the native L-α-Asp, so that the change in shape of the polypeptide caused by the substitution is minimal.

Treatments, Such as of Cancer

As discussed herein and as described in detail in the Examples section below, it has been surprisingly found that some embodiments of a polypeptide as disclosed herein have a biological activity that renders the polypeptide useful for treatment of a disease, for example cancer. In preferred embodiments, the polypeptide having an amino acid sequence set forth in any one of SEQ ID NO:11-40 retains anti-cancer activity. In preferred embodiments, the polypeptide having an amino acid sequence set forth in any one of SEQ ID NO:11-20 retains anti-cancer activity. In preferred embodiments, the polypeptide having an amino acid sequence set forth in any one of SEQ ID NO:21-30 retains anti-cancer activity. In preferred embodiments, the polypeptide having an amino acid sequence set forth in any one of SEQ ID NO:31-40 retains anti-cancer activity. In some embodiments, such a polypeptide retains anti-cancer activity and also has one or more advantages, for example, has reduced adverse side effects compared to a polypeptide having an amino acid sequence set forth in one or more of SEQ ID NO:1-10

Thus, according to an aspect of some embodiments of the teachings herein, there is also provided an isolated polypeptide as disclosed herein, or a DNA encoding therefor, for use in a method of treatment of a disease.

According to an aspect of some embodiments of the teachings herein, there is also provided an isolated polypeptide as disclosed herein, or a DNA encoding therefor, for use as a medicament for treating a disease.

According to an aspect of some embodiments of the teachings herein, there is also provided an isolated polypeptide as disclosed herein, or a DNA encoding therefor, for use in therapy.

According to an aspect of some embodiments of the teachings herein there is also provided a pharmaceutical composition comprising: an isolated polypeptide as disclosed herein, or a DNA encoding therefor; and a pharmaceutically-acceptable carrier.

According to an aspect of some embodiments of the teachings herein there is also provided the use of an isolated polypeptide as disclosed herein, or a DNA encoding therefor, for the preparation of a medicament for treating a disease.

According to an aspect of some embodiments of the teachings herein, there is also provided a method for the treatment of a disease, comprising, administering a pharmaceutically-acceptable effective amount of an isolated polypeptide as disclosed herein, or a DNA encoding therefor, to a subject in need thereof. In some embodiments, the subject is a human. In some embodiments, the subject is a non-human animal.

The DNA encoding for an isolated polypeptide as disclosed herein includes a DNA which hybridizes with the above-mentioned DNA under stringent conditions.

In some embodiments, it is advantageous to coadminister a polypeptide as disclosed herein or a DNA encoding therefor together with a chemotherapeutic agent. Suitable such chemotherapeutic agents are described in detail hereinbelow.

Thus, according to an aspect of some embodiments of the teachings herein there is also provided a pharmaceutical composition comprising: an isolated polypeptide as disclosed herein, or a DNA encoding therefor; a chemotherapeutic agent; and a pharmaceutically-acceptable carrier.

According to an aspect of some embodiments of the teachings herein there is also provided the use of an isolated polypeptide as disclosed herein, or a DNA encoding therefor, together with a chemotherapeutic agent for the preparation of a medicament for treating a disease.

According to an aspect of some embodiments of the teachings herein, there is also provided a method for the treatment of a disease, comprising, co-administering a pharmaceutically-acceptable effective amount of an isolated polypeptide as disclosed herein, or a DNA encoding therefor, together with a chemotherapeutic agent to a subject in need thereof. In some embodiments, the subject is a human. In some embodiments, the subject is a non-human animal. In some embodiments, the polypeptide or DNA encoding therefor and such a co-administered chemotherapeutic agent are administered in a single dosage form or alternatively are administered sequentially or simultaneously in separate dosage forms.

In some embodiments, a polypeptide as disclosed herein is pegylated, to improve pharmacokinetics or other parameters. Various advantages of pegylation and methods for pegylation of proteins such as Klotho proteins are known in the art, see for example Ryan S M, Mantovani G, Wang X, Haddleton D M, Brayden D J "Advances in PEGylation of important biotech molecules: delivery aspects" in Expert Opin Drug Deliv. 2008, 5(4), 371-383.

Administration

For implementing the teachings herein, a polypeptide as disclosed herein is administered by any suitable route, for example as described in PCT/JP1997/004585. For example, the polypeptide may be administered by parenteral (including intravenous, intradermal, intraperitoneal, intramuscular and subcutaneous) routes. Alternatively, the polypeptide may be administered by other delivery routes, including oral, nasal, buccal, sublingual, intra-tracheal, transdermal, transmucosal, and pulmonary. The polypeptide may be administered by continuous release or delivery, using, for example, an infusion pump, continuous infusion, controlled release formulations utilizing polymer, oil or water insoluble matrices.

Carriers or excipients known in the art can also be used to facilitate administration of the polypeptide. Examples of carriers and excipients include calcium carbonate, calcium phosphate, various sugars such as lactose, or types of starch, cellulose derivatives, gelatin, vegetable oils, polyethylene glycols and physiologically compatible solvents.

According to some embodiments, the polypeptide is administered in extended release form, which is capable of releasing the polypeptide over a predetermined release period, such that a clinically effective plasma level of the polypeptide is maintained for at least 24 hours, such as at least 48 hours, at least 72 hours, at least one week, or at least one month.

According to some embodiments, the polypeptide is administered in combination with one or more chemotherapeutic agents, including, for example, alkylating agents, antimetabolites, anthracyclines, plant alkaloids, topoisomerase inhibitors, hormone receptor modulators, hormone level modulators, and other antitumour agents.

Examples of suitable alkylating agents include, without limitation, busulfan, carboplatin, carmustine, cisplatin, chloroambucil, cyclophosphamide, dacarbazine, hexamethylmelamine, ifosfamide, mechlorethamine, melphalan, oxoplatin, streptozocin, temozolomide, thiotepa, and uramustine.

Non-limiting examples of suitable antimetabolites include azathioprine, capecitabine, carmofur, cladribine, clofarabine, cytarabine, fludarabine, fluorouracil, gemcitabine, mercaptopurine, methotrexate, premetrexed, raltitrexed, tegafur, and tioguanine Suitable anthracyclines include, for example, daunorubicin, doxorubicin, epirubicin, idarubicin, mitoxantrone and valrubicin.

Examples of suitable plant alkaloids include docetaxel, paclitaxel, vinblastine, vincristine, vindesine, and vinorelbine. Examples of suitable topoisomerase inhibitors include amsacrine, etoposide, etoposide phosphate, irinotecan, teniposide, and topotecan. Examples of suitable hormone receptor modulators include tamoxifen; and estrogen antagonists, such as faslodex. Examples of suitable hormone level modulators include aromatose inhibitors, such as letrozole, anastrazole and aromasin. Examples of other antitumor agents include dactinomycin, and other chemotherapeutic agents for treatment of obesity-related cancers, such as trastuzumab (herceptin), lapatinib, bevacizumab (avastin), cetuximab (erbitux), panitumumab, erlotinib, and sunitinib.

In such embodiments, the polypeptide as disclosed herein and the chemotherapeutic agent are administered by subcutaneous or intravenous injection.

The chemotherapeutic agent may optionally be provided in a combined dosage form, together with the polypeptide. Alternatively, the chemotherapeutic agent may be provided in a separate dosage form, for simultaneous or sequential co-administration, either before or after administration of the polypeptide.

The teachings herein further provide a composition comprising pharmaceutically acceptable amounts of a polypeptide as disclosed herein and a chemotherapeutic agent as an additional active pharmaceutical ingredient.

The composition may optionally be provided in extended-release form, as described above with regard to the polypeptide alone.

According to some embodiments of the teachings herein, there is provided a composition comprising a combination of at least two active pharmaceutical ingredients, at least one of which is a polypeptide as described herein and at least one of which is a chemotherapeutic agent, wherein the amount of polypeptide and amount of the chemotherapeutic agent alone is insufficient to achieve the therapeutic effect achieved by the administration of the combination of two or more of the active pharmaceutical ingredients. Such a composition comprises, in addition to the active pharmaceutical ingredients, a pharmaceutically acceptable carrier, and may optionally further comprise one or more pharmaceutically acceptable excipients.

Pharmaceutically-acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered subcutaneously. Saline solutions and aqueous dextrose and glycerol solutions can also be employed as liquid carriers, particularly for injectable solutions.

If desired, solutions of the above dosage compositions may be thickened with a thickening agent such as methylcellulose. They may be prepared in emulsified form, such as either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

In general, a composition as described herein is prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

Treatment Using Gene Therapy

Discussed above are various embodiments where a polypeptide as disclosed herein is administered to a subject, for example in order to treat cancer. In some embodiments, rather than administering a polypeptide, gene therapy may be preferred, whereby a DNA encoding for a polypeptide as described herein, is administered, in the usual way, to a subject. The thus-administered DNA causes the body of the subject to produce endogenous polypeptide as disclosed herein in amounts sufficient to lead to the desired therapeutic (e.g., anti-cancer) effect. In some embodiments, the DNA is delivered inserted in a recombinant vector (e.g., a bacteria) suitable for gene therapy.

In preferred embodiments the polynucleotide encoding a variant peptide has an amino acid sequence forth in any one of SEQ ID NO:51-80. In preferred embodiments the polynucleotide encoding a variant peptide has an amino acid sequence forth in any one of SEQ ID NO:51-60. In preferred embodiments the polynucleotide encoding a variant peptide has an amino acid sequence forth in any one of SEQ ID NO:61-70. In preferred embodiments the polynucleotide encoding a variant peptide has an amino acid sequence forth in any one of SEQ ID NO:71-80.

The preferred method for producing the variants is using recombinant DNA technologies, well known to those skilled in the art. For example, the variant polynucleotide may be prepared by Polymerase Chain Reaction (PCR) using specific primers for each of the variant forms or the amino acid substitutions as disclosed herein below. The PCR fragments are purified on an agarose gel and the purified DNA fragment is cloned into an expression vector and transfected into host cells. The host cells are cultured and the protein harvested according to methods known in the art.

The term "expression vector" and "recombinant expression vector" as used herein refers to a recombinant DNA molecule containing a desired coding sequence, e.g., any one of SEQ ID NO:51-80, and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. It is contemplated that the present invention encompasses expression vectors that are integrated into host cell genomes, as well as vectors that remain unintegrated into the host genome.

Thus, in some embodiments of the teachings herein is provided the use of DNA encoding for a polypeptide as disclosed herein, as a medicament, for example for the treatment of cancer.

In some embodiments the teachings herein provide a method of treatment (in some embodiments, treatment of cancer) comprising administering to a subject in need thereof DNA encoding for a polypeptide as disclosed herein.

In some embodiments, the cancer is selected from the group consisting of breast cancer, pancreatic cancer, colon cancer, lung cancer, cervical cancer, ovarian cancer, and prostate cancer. In some embodiments, the cancer is breast cancer. In some embodiments, the cancer is pancreatic cancer. In some embodiments, the cancer is metastatic cancer.

The DNA may be a DNA for encoding any suitable polypeptide as disclosed herein, and may be made, isolated, purified, and provided in any suitable fashion known to one skilled in the art, for example as described in PCT/JP1997/004585 (published, inter alia, in EP 0 945 506 B1). For example, as is well known to one skilled in the art, a preferred way of providing a protein-encoding DNA, such as DNA encoding a polypeptide as disclosed herein, is by inserting the DNA in a recombinant vector, especially a recombinant vector suitable for gene therapy.

In some embodiments, the DNA encoding for a polypeptide as disclosed herein is a DNA encoding for a polypeptide comprising an amino-acid residue sequence having a homology of not less than 80% (in some embodiments, not less than 90%, not less than 95% and even not less than 98% homology) with a polypeptide having an amino-acid residue sequence selected from the group consisting of the amino-acid residue sequences represented by:
  SEQ ID NO:1 (encoded by DNA having the sequence represented by SEQ ID NO:41, Accession nr. AR343616);
  residues 29-1012 of SEQ ID NO:1 (set-forth in SEQ ID NO:2);
  residues 1-980 of SEQ ID NO:1 (set-forth in SEQ ID NO:3);
  residues 29-980 of SEQ ID NO:1 (set-forth in SEQ ID NO:4);
  residues 1-568 of SEQ ID NO:1 (set-forth in SEQ ID NO:5);
  residues 29-568 of SEQ ID NO 1 (set-forth in SEQ ID NO:6);
  residues 34-549 of SEQ ID NO:1 (set-forth in SEQ ID NO:7);
  SEQ ID NO:8 (encoded by DNA having the sequence represented by SEQ ID NO:48, Accession nr. AR343617);
  residues 29-549 of SEQ ID NO:8 (set-forth in SEQ ID NO:9); and
  residues 34-549 of SEQ ID NO:8 (set-forth in SEQ ID NO:10),
wherein the L-Glu of residue 414 is substituted with an a-amino acid residue different from L-Glu having an amino acid sequence set forth in SEQ ID NO:11-20; the L-Asp of residue 238 is substituted with an α-amino acid different from L-Asp having an amino acid sequence set forth in SEQ ID NO:21-30; or the L-Glu of residue 414 is substituted with an α-amino acid residue different from L-Glu and the L-Asp of residue 238 is substituted with an α-amino acid different from L-Asp having an amino acid sequence set forth in SEQ ID NO:31-40, numbered with reference to SEQ ID NO:1.

In some embodiments, the DNA encoding a polypeptide according to the teachings herein is a DNA which hybridizes with a DNA described above under stringent conditions. By "DNA which hybridizes under stringent conditions" is meant DNA obtained by colony hybridization, plaque hybridization or Southern blot hybridization using DNA encoding the polypeptide, specifically including DNA identified after hybridization, using a filter on which colony- or plaque-derived DNA has been immobilized in the presence of 0.7 to 1.0 M NaCl at 65° C. and washing the resulting filter using 0.1 to 2×SSC solutions (the composition of 1×SSC solution comprises 150 mM sodium chloride and 15 mM sodium citrate) at 65° C. Hybridization can be carried out according to a method described, for example, in Molecular Cloning, A Laboratory Manual, the 2nd edition (Sambrook, Fritsch, & Maniatis eds., Cold Spring Harbor Laboratory Press, 1989). Specific examples of the DNA which hybridizes include DNA having a homology of 60% or more with a nucleotide sequence of the DNA encoding the polypeptide of an amino acid sequence selected from amino acid sequences represented by SEQ ID NO:1;
  residues 29-1012 of SEQ ID NO:1 (set-forth in SEQ ID NO:2);
  residues 1-980 of SEQ ID NO:1 (set-forth in SEQ ID NO:3);
  residues 29-980 of SEQ ID NO:1 (set-forth in SEQ ID NO:4);
  residues 1-568 of SEQ ID NO:1 (set-forth in SEQ ID NO:5);
  residues 29-568 of SEQ ID NO 1 (set-forth in SEQ ID NO:6);
  residues 34-549 of SEQ ID NO:1 (set-forth in SEQ ID NO:7);
  SEQ ID NO:8 (encoded by DNA having the sequence represented by SEQ ID NO:18, Accession nr. AR343617);
  residues 29-549 of SEQ ID NO:8 (set-forth in SEQ ID NO:9); and
  residues 34-549 of SEQ ID NO:8 (set-forth in SEQ ID NO:10), preferably DNA having a homology of 80% or more, and more preferably DNA having a homology of 95% or more.

The DNA encoding for a polypeptide as described herein may be administered by any suitable route, for example as described in PCT/JP1997/004585. For example, in some embodiments the DNA is provided inserted in a recombinant vector (e.g., a bacteria), and the vector administered by parenteral routes. According to some embodiments, the DNA encoding for a polypeptide as disclosed herein is administered in combination with one or more chemotherapeutic agents, as discussed above for administration of Klotho protein as a polypeptide As noted above, in some embodiments, the teachings herein (e.g., administration of a polypeptide or of DNA encoding therefor) are directed to treating cancer for example, to reduce or eliminate cancerous tumors and metastatic cells and tumors.

In some embodiments, the teachings herein (e.g., administration of a polypeptide or of DNA encoding therefor) are implemented to treat cancer as an adjuvant treatment, that is to say together with another modality of cancer treatment, such as a known modality of cancer treatment, for example, together with radiotherapy, brachytherapy, surgery and the like.

In some embodiments, the teachings herein (e.g., administration of a polypeptide or of DNA encoding therefor) are implemented to treat cancer as a neo-adjuvant treatment, for example to reduce the size of a tumor prior to surgical excision thereof.

In some embodiments, the teachings herein are implemented prophylactically (e.g., administration of a polypeptide or of DNA encoding therefor). For example, in some embodiments, the teachings herein are implemented on a person who has not yet been diagnosed with cancer but is a member of a group at high risk of being diagnosed with cancer, for example has a genetic inclination to cancer (family history), a pathological indication of pre-cancer (e.g., pre breast cancer), DCIS (ductal carcinoma in situ), clinically significant alcohol use, age or use of HRT (hormone replacement therapy). For example, in some embodiments, the teachings herein are implemented on a person whose cancer is in remission (complete or partial) but may be susceptible to a return of the disease.

Exemplary embodiments of the teachings herein are discussed hereinbelow with reference to specific materials, methods and examples. The material, methods and examples discussed herein are illustrative and not intended to be limiting. In some embodiments, methods and materials similar or equivalent to those described herein are used in the practice or testing of embodiments of the invention. It is to be understood that the invention is not necessarily limited in its application to the details of construction and the arrangement of the components and/or methods set forth in the following description and/or illustrated in the drawings. The invention is capable of other embodiments or of being practiced or carried out in various ways.

EXAMPLES

Materials and Methods
Chemicals, Antibodies and Constructs:

bFGF was obtained from Biological Industries (Kibbutz Beit Haemek, Israel). IGF-1 was obtained from PeproTech Inc (Rocky Hill, N.J.), G418 from Invitrogen (Carlsbad, Calif.). Antibodies used in this study: anti-IGF-1β receptor (Santa Cruz Biotechnology, Santa Cruz, Calif.), anti-phospho-AKT1 (S473), phospho-IGF-1R (Y1131), total pan-AKT (Cell Signaling Technology, Danvers, Mass.), anti-diphosphorylated and -total ERK 1/2 (Sigma), total IRS1 from Upstate Chemicon (Temecula, Calif., USA), phospho-IRS1 (Invitrogen), anti-HA (Covance, Princeton, N.J., USA). The Klotho protein (for murine Klotho having SEQ ID NO. 81) expression vector was a generous gift of Y. Nabeshima (Kyoto University, Japan). Soluble human Klotho protein (hKL) was obtained from R&D Systems (Minneapolis, Minn. USA). Human KL1 (hKL1, SEQ ID NO: 8) and human KL1 (residues 34-549 of SEQ ID NO: 10) were obtained from PeproTech Inc. (Rocky Hill, N.J., USA). Klotho variant construction:

Point mutations were inserted to the DNA (using full length mouse klotho or ssKL1 (KL1 domain with 1-28 amino acid signal sequence) in pcDNA3) to generate amino acid substitutions in positions 416 and 238 of the polypeptide (corresponding to residues 414 and 238 of human Klotho of SEQ ID NO:1 and SEQ ID NO:5) using QuikChange® Site-Directed Mutagenesis Kit (Stratagene, La Jolla, Calif., USA). Accuracy of plasmid sequences was verified by sequencing following mutagenesis. All examples hereinbelow utilized mouse Klotho protein, in which the amino acid sequence is shifted by 2 amino acids from the human Klotho protein (SEQ ID NO:1). For example, Glu at position 416 (E416) in mouse Klotho protein is the equivalent of Glu 414 (E414) in human Klotho protein and variants (i.e., Glu 414 substituted in SEQ ID NO:11-20), and likewise Asp at position 240 in mouse Klotho protein is the equivalent of Asp 238 in human Klotho protein and variants (i.e., Asp238 substituted in SEQ ID NO:21-30).

Cells and transfections: Breast cancer cell lines and HEK293 cells were obtained from the American Type Culture Collection (Manassas, Va.). All transfections used Lipofectamine® 2000 (Invitrogen). Stable clones were generated by selection in complete culture medium containing 750 g/ml G418.

Western blot analysis: For breast cancer cell lines, cells were harvested and lysed for total protein extraction in RIPA buffer (50 mM Tris-Cl pH 7.4, 150 mM NaCl, 1% NP-40, 0.25% Na-deoxycholate, 1 mM EDTA, 1 mM NaF) together with a protease inhibitor cocktail (Sigma). 50 μg protein extracts were loaded on 10% polyacrylamide gels, separated electrophoretically and blotted from the gel onto nitrocellulose membrane (Schleicher & Schuell Bioscience GmbH, Dassel, Del.). The membranes were then immunoblotted with the indicated antibodies.

Colony Assays:

Breast cancer cells: Two days following transfection with the indicated plasmids, G418 (750 μg/ml) was added to the culture media; and at day 14, the cells were stained using gentian violet. Untransfected cells were treated similarly, and all died within the 2 weeks of culture in the selection media. Quantification of the results was performed using AlphaImager 2000 (Alpha Innotech, CA).

3-(4,5-dimethylthiazol-2-yl)-2,5-diphenyltetrazolium bromide (MTT) Viability Assay Breast cancer cells: $7.5 \times 10^3$ cells/well were plated in 96-well plates, cultured in the appropriate culture media, and transfected with either control plasmid or plasmid expressing Klotho protein; and at indicated times, cells were cultured for two hours with 500 g/ml MTT reagent (Sigma-Aldrich, St. Louis, Mo.). The medium was aspirated, and the cells were resuspended in dimethyl sulfoxide (DMSO). Absorbance of the formazan product was measured by an enzyme-linked immunosorbent assay reader. Optical density is directly correlated with cell quantity.

Statistical Analysis:

Results are presented as mean±standard deviation (SD). Categorized variables were compared between the study groups using Fisher's exact test and continuous variables were compared using t-test. All significance tests were two-tailed and a P-value of <0.05 was considered as statistically significant. The nature of interaction between Klotho protein and 5-FU or Gemcitabine was analyzed using the additive model (Jonsson et al., 1998). A ratio between the observed and the predicted viability was calculated for all combinations and a ratio <0.8 for the interaction was considered to be synergistic.

Superimposition of KLrP on KL1 and KL2 to Identify Active Site

Figure 1B:
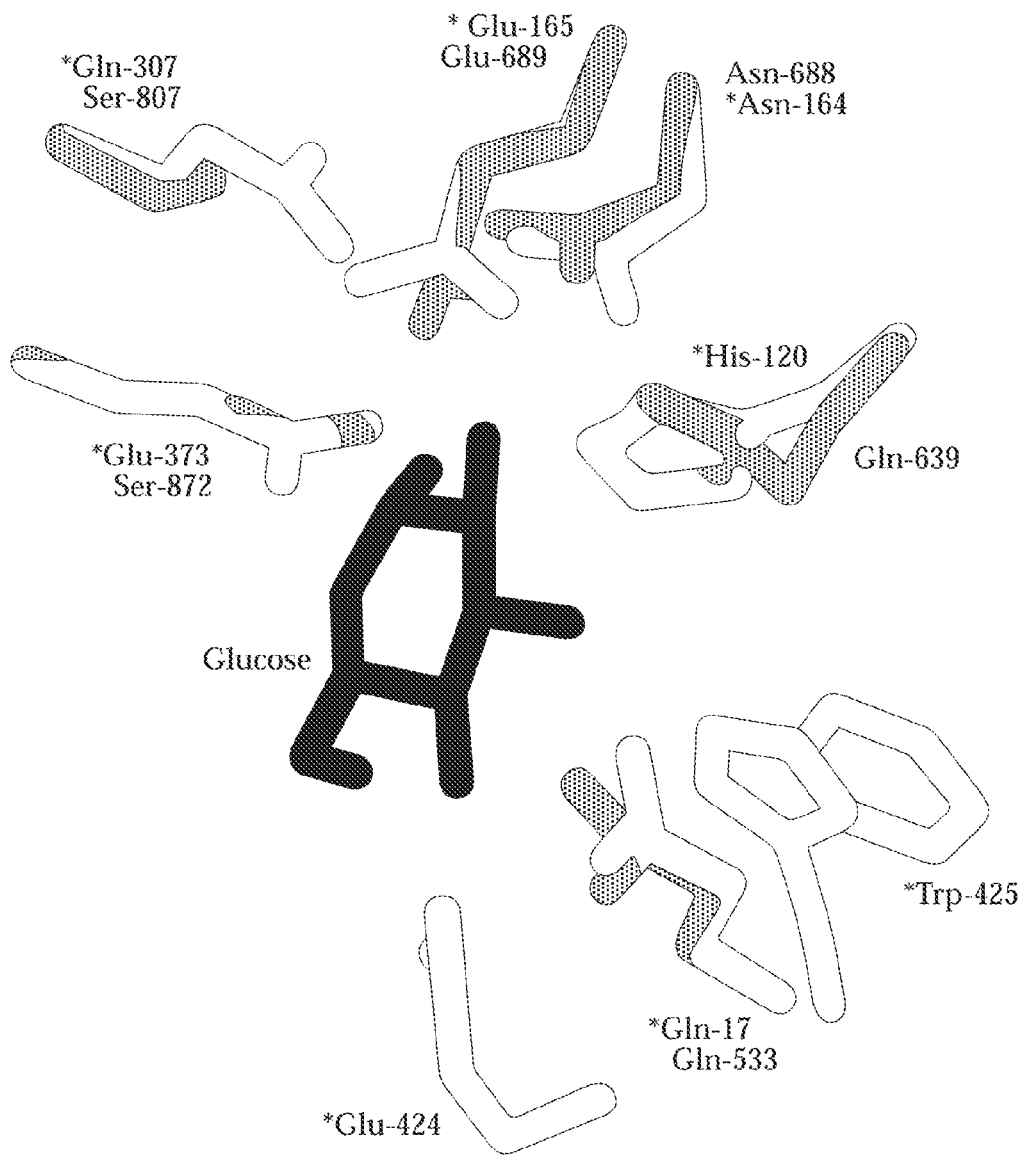
FIG. 1B schematically depicts portions of KLrP surrounding a glucose molecule, on which portions of native Klotho protein KL2 domain is superimposed, demonstrating the dissimilarity of the respective active sites.

The classic family-1 glycosidase (glycoside hydrolase) KLrP ((klotho-related protein, Hyashi 2007 JBC 282(42): 30889) was crystallized using methods known in the art, with part of its product, glucose and the three-dimensional structure determined. In FIGS. 1A and 1B, the side chains of the active-site amino-acid residues of KLrP are presented in white (outline, identity marked with an asterisk) surrounding the glucose molecule in black.

In FIG. 1A, superimposed on the KLrP side chains are the side chains of amino-acid residues of a portion of native Klotho protein KL1 domain that constitutes an active site of the KL1 domain, where the side-chains are depicted filled and identity designated without an asterisk.

In FIG. 1B, superimposed on the KLrP side chains are the side chains of amino-acid residues of a portion of native Klotho protein KL2 domain that constitutes an active site of the KL2 domain, where the side-chains are depicted filled and identity designated without an asterisk.

KLrP displays the Koshland retaining mechanism. In similar manner to other family 1 glycoside hydrolases, two glutamic acid residues are identified as the catalytic residues. The KL1 Glu-373 is found to be the nucleophile and Glu-165 is found to be the acid/base catalyst.

As seen in FIG. 1A, the active site of the Klotho protein KL1 domain has an arrangement of amino-acid residue side-chains similar to that of KLrP including the Klotho protein Glu-414 superimposed on the KLrP nucleophilic residue Glu-373. The residue corresponding to the KLrP acid/base catalyst Glu-165 is the Klotho protein Asn-239. Asn-239 does not serve as an acid/base catalyst. The Inventors believe that the KL1 domain of Klotho protein may function as a glycoside hydrolase with Asp-238 as the acid/base catalyst, since it is positioned at the "correct" distance from Glu-414 and therefore might replace Asn-239.

In contrast, the active site of the Klotho protein KL2 domain does not share homology with the active site of KLrP, as shown in FIG. 1B. Almost all the residues are different except for Klotho protein Glu-689 corresponding to the KLrP Glu-165 (the acid/base catalyst in KLrP) and the Klotho protein Asn-688 corresponding to the KLrP Asn-688. In Klotho protein KL2 domain Ser-872 replaces the nucleophilic KLrP Glu-373.

Anti-Tumorigenic Activity of Klotho Variant Polypeptides

MCF-7 and MDA-MB-231 cells were transfected with:
   a. an empty vector (pDNA3);
   b. wild-type full length Klotho (FL-KL) equivalent to SEQ ID NO:1;
   c. a Klotho protein variant according to an embodiment of the teachings herein (FL-KL (E416Q), that is mouse full length Klotho where native L-Glu at 416 is substituted with L-Gln, equivalent to E414Q in the respective human Klotho protein variant) equivalent to SEQ ID NO:11;
   d. wild-type KL1 domain (KL1) equivalent to SEQ ID NO:8;
   e. a KL1 domain variant protein according to an embodiment of the teachings herein (KL1 (E416Q), that is mouse KL1 where native L-Glu at 416 is substituted with L-Gln, equivalent to E414Q in the respective human KL1 variant) equivalent to SEQ ID NO:18; and
   f. wild-type KL2 (KL2) equivalent to SEQ ID NO:85.

The transfected cells were cultured in media containing G418 for two weeks. Colonies were stained with crystal violet and photographed.

Figure 2:
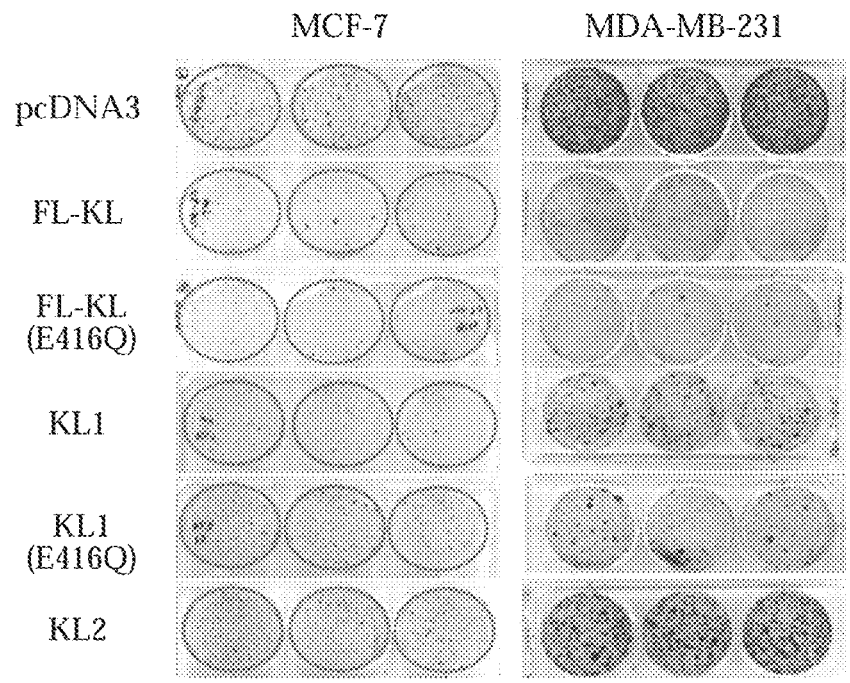
FIG. 2 is a reproduction of a photograph of a colony formation assay, in which MCF-7 and MDA-MB-231 cells were transfected with one of the following expression vectors: an empty vector (pDNA3); wild-type full length Klotho (FL-KL); a Klotho protein variant (FL-KL (E416Q), which is a mouse full length Klotho where native L-Glu at 416 is substituted with L-Gln, equivalent to E414Q in the respective human Klotho protein variant); wild-type KL1 (KL1); KL1 variant according to an embodiment of the teachings (KL1 (E416Q), that is mouse KL1 where native L-Glu at 416 is substituted with L-Gln, equivalent to E414Q in the respective human KL1 variant); and wild-type KL2 (KL2). Transfected cells were cultured in media containing G418 for two weeks, and colonies were stained with crystal violet.

As seen in FIG. 2, the Klotho protein variants were shown to retain at least some of the anti-tumorigenic activity of the comparable native Klotho protein.

Effect of a Klotho Variant Polypeptide on the IGF-1 Pathway

MCF-7 cells were transfected with:
   a. a wild type full length Klotho (FL-mKLOTHO/WT) equivalent to SEQ ID NO:1;
   b. a first Klotho variant polypeptide according to an embodiment of the teachings herein (FL-mKLOTHO/E416Q: mouse FL-KL E416Q, equivalent to E414Q in the respective human Klotho protein variant) equivalent to SEQ ID NO:11;
   c. wild type KL1 domain (ssKL1/WT; KL1 domain with 1-28 signal sequence) equivalent to SEQ ID NO:8;
   d. KL1 domain variant polypeptide according to an embodiment of the teachings herein (ssKL1/WT: E416Q: mouse KL1 E416Q, equivalent to E414Q in the respective human KL1 variant) or
   e. an empty vector (pcDNA3).

After 24 hours, cells were serum starved for 48 hours and treated with IGF-1. Following treatment, cells were harvested and proteins were resolved and immunoblotted using antibodies as indicated.

Figure 3:
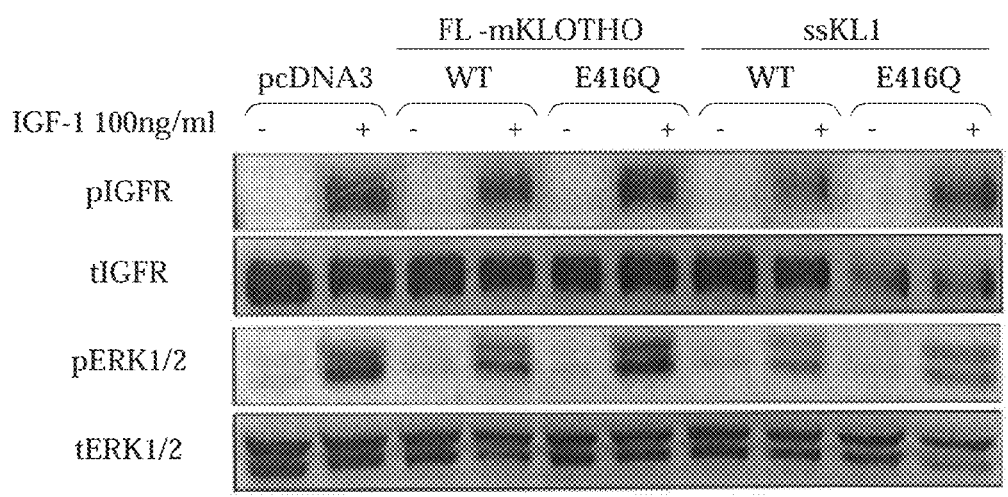
FIG. 3 is an immunoblot of MCF-7 cells transfected with an empty vector (pcDNA3); a wild type full length Klotho (FL-mKLOTHO/WT); a first Klotho variant polypeptide (FL-mKLOTHO/E416Q: mouse FL-KL E416Q, equivalent to E414Q in the respective human Klotho protein variant), wild type KL1 (ssKL1/WT; including amino acids 1-28 signal sequence); a Klotho variant polypeptide (ssKL1/WT: E416Q: mouse KL1 E416Q, equivalent to E414Q in the respective human KL1 variant) treated or untreated with IGF, and exposed to the antibodies indicated.

Results are presented in FIG. 3. FIG. 3 shows that while wild type full length Klotho protein inhibits IGF-1 signaling, as evidenced by inhibition of IGF-1R and ERK1/2 phosphorylation (pIGFR and pERK1/2), E416Q-variant Klotho and KL1 according to the teachings herein do not retain this activity. This suggests that mechanisms other than IGF-1 inhibition may be responsible to the reported anti-cancer activity. Total ERK (tERK) and total IGF-1 (tIGF1) refer to phosphorylated and non-phosphorylated ERK1/2 and phosphorylated and non-phosphorylated IGF-1, respectively.

Effect of Klotho Variant Polypeptides on FGF23 Activity

Figure 4:
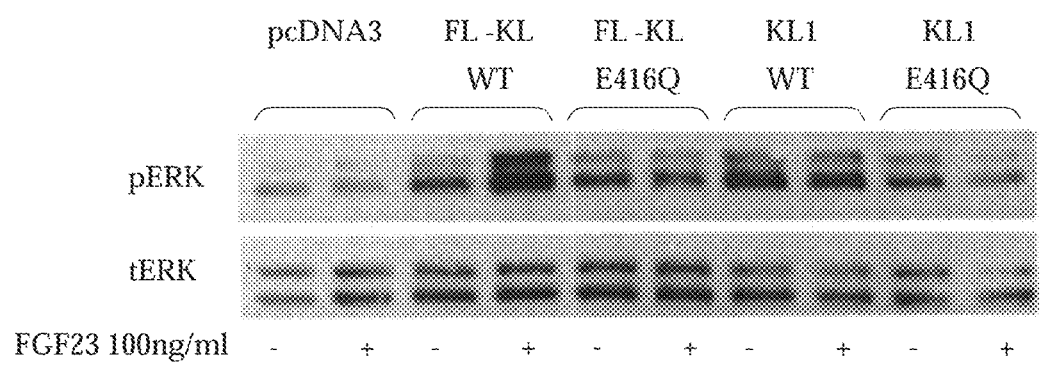
FIG. 4 is an immunoblot of HEK293 cells transfected with wild type full length Klotho (FL-KL/WT); a Klotho variant polypeptide (FL-KL/E416Q) according to an embodiment of the teachings herein; wild type KL1 (KL1/WT); or a KL1 variant polypeptide (KL1/E416Q) according to an embodiment of the teachings herein, and treated with FGF23, exposed to the antibodies indicated.

HEK293 cells were treated as for the previous example, with the addition of FGF23. The two Klotho variant polypeptides (FL-KL/E416Q and KL1/E416Q, equivalent to E414Q in the respective human Klotho protein variants) were found not to function as a cofactor for FGF23. Results are presented in FIG. 4. The variant polypeptides exhibit less FGFR co-activation with FGF23 than the native polypeptides, as determined by phosphorylation of ERK (pERK) compared to total ERK (tERK).

Results and Discussion

The present Inventors have established previously that Klotho protein expression is reduced in breast and pancreatic cancers, and that treatment with soluble Klotho protein inhibits growth of breast and pancreatic cancer cell in vitro and in vivo.

The Inventors have now demonstrated that anti-cancer activities of Klotho are mediated by the KL1 domain. KL1 appears to be a more potent inhibitor of the IGF-1 pathway than full-length Klotho protein. Yet, unlike full length Klotho protein, KL1 does not control phosphate homeostasis and does not interfere with serum phosphate levels. As KL1 is 560 amino acids long (compared to 1012 amino acids of full length Klotho protein), production of KL1 is expected to be easier than that of full length Klotho protein. Even at this size, which is similar to that of antibodies, the KL1 is expected to be stable. Therefore, KL1 may serve as a better candidate than full length Klotho protein for therapeutic use.

Interestingly, variation of a putative enzymatically active site of Klotho protein (as demonstrated with mouse FL-KL E416Q and KL1 E416Q (equivalent to human FL-KL E414Q and KL1 E414Q, respectively) yields a protein that exhibits better anti-cancer properties. These variants do not mediate FGF23 signaling and seem to be more stable than the native protein. Interestingly, the variants do not inhibit IGF-1 signaling, as opposed to the wild type proteins, suggesting IGF-1 plays a modest role, if any, in mediating Klotho protein anti-cancer activities. Therefore, the Klotho variant polypeptides in accordance with the teachings herein may serve as better candidates for therapeutic use than either full length native Klotho or KL1.

SEQUENCE LISTING

This application incorporates-by-reference nucleotide and/or amino acid sequences which are present in the file named "Klotho_SEQ_listing_15APR2013.ST25.txt", which is 392 kilobytes in size, and which was created on Apr. 15, 2013 in the IBM-PC machine format, having an operating system compatibility with MS-Windows, and is submitted herewith.

Key to SEQ ID NO:

| Poly-peptide SEQ ID NO: | encoded by poly-nucleotide SEQ ID NO: | L-Glu pos 414 poly-peptide SEQ ID NO: | encoded by poly-nucleotide SEQ ID NO: | L-Asp pos 238 poly-peptide SEQ ID NO: | encoded by poly-nucleotide SEQ ID NO: | L-Glu pos 414 + L-Asp pos 238 poly-peptide SEQ ID NO: | encoded by poly-nucleotide SEQ ID NO: |
|---|---|---|---|---|---|---|---|
| AAQ41828 aa 1-1012 | 1 | 41 | 11 | 51 | 21 | 61 | 31 | 71 |
| AAQ41828 aa 29-1012 | 2 | 42 | 12 | 52 | 22 | 62 | 32 | 72 |
| AAQ41828 aa 1-980 | 3 | 43 | 13 | 53 | 23 | 63 | 33 | 73 |
| AAQ41828 aa 29-980 | 4 | 44 | 14 | 54 | 24 | 64 | 34 | 74 |
| AAQ41828 aa 1-568 | 5 | 45 | 15 | 55 | 25 | 65 | 35 | 75 |
| AAQ41828 aa 29-568 | 6 | 46 | 16 | 56 | 26 | 66 | 36 | 76 |
| AAQ41828 aa 34-549 | 7 | 47 | 17 | 57 | 27 | 67 | 37 | 77 |
| AAQ41829 aa 1-549 | 8 | 48 | 18 | 58 | 28 | 68 | 38 | 78 |
| AAQ41829 aa 29-549 | 9 | 49 | 19 | 59 | 29 | 69 | 39 | 79 |
| AAQ41829 aa 34-549 | 10 | 50 | 20 | 60 | 30 | 70 | 40 | 80 |

(pos = position)
SEQ ID NO: 81 mouse kidney AAQ41830 FL mouse Klotho polypeptide
SEQ ID NO: 82 mouse kidney AAQ41831 mouse KL1 polypeptide
SEQ ID NO: 83 AR343618 polynucleotide encoding SEQ ID NO: 81
SEQ ID NO: 84 AR343619 polynucleotide encoding SEQ ID NO: 82
SEQ ID NO: 85: amino acid sequence of Human KL2 domain (amino acids 569-980 of klotho)

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention.

To the extent that section headings are used, they should not be construed as necessarily limiting.

REFERENCES

Arking D E, Becker D M, Yanek L R, Fallin D, Judge D P, Moy T F, et al. (2003). Klotho allele status and the risk of early-onset occult coronary artery disease. *Am J Hum Genet* 72: 1154-1161.

Arking D E, Krebsova A, Macek M Sr., Macek M Jr, Arking A, Mian I S, et al. (2002). Association of human aging with a functional variant of klotho. *Proc Natl Acad Sci USA* 99: 856-861.

Bartucci M, Morelli C, Mauro L, Ando' S, Surmacz E. (2001). Differential Insulin-like Growth Factor I Receptor Signaling and Function in Estrogen Receptor (ER)-positive MCF-7 and ER-negative MDA-MB-231 Breast Cancer Cells. *Cancer Res* 61: 6747-6754.

Bergmann U et al. (1995). Insulin-like growth factor I overexpression in human pancreatic cancer: evidence for autocrine and paracrine roles. *Cancer Res.* 15: 55(10): 2007-11.

Brownstein C A, Adler F, Nelson-Williams C, Iijima J, Li P, Imura A, et al. (2008). A translocation causing increased alpha-klotho level results in hypophosphatemic rickets and hyperparathyroidism. *Proc Natl Acad Sci USA*. 105: 3455-60.

Chen C-D, Podvin S, Gillespie E. Leeman S E, Abraham C R. (2007). Insulin stimulates the cleavage and release of the extracellular domain of Klotho by ADAM10 and ADAM17. *Proc Natl Acad Sci USA* 104: 19796-19801.

Chihara Y, Rakugi H, Ishikawa K, Ikushima M, Maekawa Y, Ohta J, et al. (2006). Klotho protein promotes adipocyte differentiation. *Endocrinology* 147: 3835-3842.

de Oliveira R M (2006). Klotho RNAi induces premature senescence of human cells via a p53/p21 dependent pathway. *FEBS Lett* 580: 5753-5758.

Edderkaoui M et al. Insulin-like growth factor-I receptor mediates the prosurvival effect of fibronectin.

El-Shewy H M, Lee M-H, Obeid L M, Jaffa A A, Luttrell L M. (2007). The Insulin-like growth factor type 1 and insulin-like growth factor type 2/mannose-6-phosphate receptors independently regulate ERK1/2 activity in HEK293 cells. *J Biol Chem* 282: 26150-26157.

Geier A, Beery R, Haimsohn M, Karasik A. (1995). Insulin-like growth factor-1 inhibits cell death induced by anti-cancer drugs in the MCF-7 cells: involvement of growth factors in drug resistance. *Cancer Invest* 13: 480-486.

Gery S, Tanosaki S, Bose S, Bose N, Vadgama J, Koeffler H P. (2005). Down-regulation and growth inhibitory role of C/EBP {alpha} in breast cancer. *Clin Cancer Res* 11: 3184-3190.

Gomis R R, Alarcon C, Nadal C, Van Poznak C, Massague J. (2006). C/EBP[beta] at the core of the TGF[beta] cytostatic response and its evasion in metastatic breast cancer cells. *Cancer Cell* 10: 203-214.

Haimsohn M, Beery R, Karasik A, Kanety H, Geier A. (2002). Aurintricarboxylic acid induces a distinct activation of the IGF-I receptor signaling within MDA-231 Cells. *Endocrinology* 143: 837-845.

Haluska P, Carboni J M, Loegering D A, Lee F Y, Wittman M, Saulnier M G, et al. (2006). In vitro and in vivo antitumor effects of the dual insulin-like growth factor-I/insulin receptor inhibitor, BMS-554417. *Cancer Res* 66: 362-371.

Ikushima M, Rakugi H, Ishikawa K, Maekawa Y, Yamamoto K, Ohta J. (2006). Anti-apoptotic and anti-senescence effects of Klotho on vascular endothelial cells. *Biochem Biophys Res Commun* 339: 827-832.

Imura A, Iwano A, Tohyama O, Tsuji Y, Nozaki K, Hashimoto N, et al. (2004). Secreted Klotho protein in sera and CSF: implication for post-translational cleavage in release of Klotho protein from cell membrane. *FEBS Lett* 565: 143-147.

Imura A, Tsuji Y, Murata M, Maeda R, Kubota K, Iwano A, et al. (2007). {alpha}-Klotho as a Regulator of Calcium Homeostasis. *Science* 316: 1615-1618.

Ito S, Kinoshita S, Shiraishi N, Nakagawa S, Sekine S, Fujimori T, et al. (2000). Molecular cloning and expression analyses of mouse [beta]klotho, which encodes a novel Klotho family protein. *Mech Dev* 98: 115-119.

Jonsson E, Fridborg H, Nygren P, Larsson R. (1998). Synergistic interactions of combinations of toptecan with standard drugs in primary cultures of human tumor cells from patients. *Eur J Clin Pharmacol* 54: 509-14.

Kama E et al., Serum and tissue level of insulin-like growth factor-I (IGF-I) and IGF-I binding proteins as an index of pancreatitis and pancreatic cancer. Int J Exp Pathol. 2002 October; 83(5):239-45.

Kato Y, Arakawa E, Kinoshita S, Shirai A, Furuya A, Yamano K, et al. (2000). Establishment of the anti-klotho monoclonal antibodies and detection of klotho protein in kidneys. *Biochem Biophys Res Commun* 267: 597-602.

Kim Y, Kim J-H, Nam Y J, Kong M, Kim Y J, Yu K H, et al. (2006). Klotho is a genetic risk factor for ischemic stroke caused by cardioembolism in Korean females. *Neurosci Lett* 407: 189-194.

Kuro-o M, Matsumura Y, Aizawa H, Kawaguchi H, Suga T, Utsugi T, et al. (1997). Mutation of the mouse klotho gene leads to a syndrome resembling ageing. *Nature* 390: 45-51.

Kurosu H, Ogawa Y, Miyoshi M, Yamamoto M, Nandi A, Rosenblatt K P, et al. (2006). Regulation of fibroblast growth factor-23 signaling by klotho. *J Biol Chem* 281: 6120-6123.

Kurosu H et al. Suppression of aging in mice by the hormone Klotho. Science. 2005 Sep. 16; 309(5742):1829-33. J Biol Chem. 2007 Sep. 14; 282(37):26646-55.

Kurosu H, Yamamoto M, Clark J D, Pastor J V, Nandi A, Gurnani P, et al. (2005). Suppression of aging in mice by the hormone klotho. *Science* 309: 1829-1833.

Lacroix M, Leclercq G. (2004). Relevance of breast cancer cell lines as models for breast tumours: an update. *Breast Cancer Res Treat* 83: 249-289.

Li X, Kim J W, Gronborg M, Urlaub H, Lane M D, Tang Q-Q. (2007). Role of cdk2 in the sequential phosphorylation/activation of C/EBPbeta during adipocyte differentiation. *Proc Natl Acad Sci USA* 104: 11597-11602.

Matsumura Y, Aizawa H, Shiraki-Iida T, Nagai R, Kuro-o M, Nabeshima Y-i. (1998). Identification of the human klotho gene and its two transcripts encoding membrane and secreted klotho protein. *Biochem Biophys Res Commun* 242: 626-630.

Mitsiades C S, Mitsiades N S, McMullan C J, Poulaki V, Shringarpure R, Akiyama M, et al. (2004). Inhibition of the insulin-like growth factor receptor-1 tyrosine kinase activity as a therapeutic strategy for multiple myeloma, other hematologic malignancies, and solid tumors. *Cancer Cell* 5: 221-230.

Ohyama Y, Kurabayashi M, Masuda H, Nakamura T, Aihara Y, Kaname T, et al. (1998). Molecular cloning of rat klotho cDNA: markedly decreased expression of klotho by acute inflammatory stress. *Biochem Biophys Res Commun* 251: 920-925.

Shiraki-Iida T, Aizawa H, Matsumura Y, Sekine S, Iida A, Anazawa H, et al. (1998). Structure of the mouse klotho gene and its two transcripts encoding membrane and secreted protein. *FEBS Lett* 424: 6-10.

Spector N L, Yarden Y, Smith B, Lyass L, Trusk P, Pry K, et al. (2007). Activation of AMP-activated protein kinase by human EGF receptor 2/EGF receptor tyrosine kinase inhibitor protects cardiac cells. *Proc Natl Acad Sci USA* 104: 10607-10612.

Urakawa I, Yamazaki Y, Shimada T, Iijima K, Hasegawa H, Okawa K, et al. (2006). Klotho converts canonical FGF receptor into a specific receptor for FGF23. *Nature* 444: 770-774.

Utsugi T, Ohno T, Ohyama Y, Uchiyama T, Saito Y, Matsumura Y, et al. (2000). Decreased insulin production and increased insulin sensitivity in the klotho mutant mouse, a novel animal model for human aging. *Metabolism* 49: 1118-1123.

Wolf I, Bose S, Williamson E A, Miller C W, Karlan B Y, Koeffler HP. (2007). FOXA1: Growth inhibitor and a favorable prognostic factor in human breast cancer. *Int J Cancer* 120: 1013-1022.

Wolf I, Levanon-Cohen S, Bose S, Ligumsky H, Sredni B, Kanety H, et al. (2008). Klotho: a tumor suppressor and a modulator of the IGF-1 and FGF pathways in human breast cancer. *Oncogene* 27: 7094-105.

Wolf I, O'Kelly J, Rubinek T, Tong M, Nguyen A, Lin B T, et al. (2006a). 15-Hydroxyprostaglandin dehydrogenase is a tumor suppressor of human breast cancer. *Cancer Res* 66: 7818-7823.

Wolf I, Sadetzki S, Gluck I, Oberman B, Ben-David M, Papa M Z, et al. (2006b). Association between diabetes mellitus and adverse characteristics of breast cancer at presentation. *Eur J Cancer* 42: 1077-1082.

Wu X, Lemon B, Li X, Gupte J, Weiszmann J, Stevens J, et al. (2008). C-terminal tail of FGF19 determines its specificity towards Klotho co-receptors. *J Biol Chem* 283: 33304-9.

Yamamoto M, Clark J D, Pastor J V, Gurnani P, Nandi A, Kurosu H, et al. (2005). Regulation of oxidative stress by the anti-aging hormone klotho. *J Biol Chem* 280: 38029-38034.

Yee D. (2006). Targeting insulin-like growth factor pathways. *Br J Cancer* 94: 465-468.

Zarrabeitia M, Hernandez J, Valero C, Zarrabeitia A, Ortiz F, Gonzalez-Macias J, et al. (2007). Klotho gene polymorphism and male bone mass. *Calcif Tissue Int* 80: 10-14.

What is claimed is:

1. An isolated polypeptide comprising an amino-acid residue sequence selected from the group consisting of:
   SEQ ID NO: 1 or a sequence at least 95% identical thereto;
   residues 29-1012 of SEQ ID NO:1 or a sequence at least 95% identical thereto;
   residues 1-980 of SEQ ID NO:1 or a sequence at least 95% identical thereto;
   residues 29-980 of SEQ ID NO:1 or a sequence at least 95% identical thereto;
   residues 1-568 of SEQ ID NO:1 or a sequence at least 95% identical thereto;
   residues 29-568 of SEQ ID NO:1 or a sequence at least 95% identical thereto;
   residues 34-549 of SEQ ID NO:1 or a sequence at least 95% identical thereto;
   SEQ ID NO:8 or a sequence at least 95% identical thereto;
   residues 29-549 of SEQ ID NO:8 or a sequence at least 95% identical thereto; and
   residues 34-549 of SEQ ID NO:8 or a sequence at least 95% identical thereto,
   wherein:
      the L-Glu of residue 414 is substituted with L-α-Gln.

2. An isolated polypeptide comprising a Klotho amino acid sequence selected from the group consisting of:
   SEQ ID NO:1 or a sequence at least 95% identical thereto;
   residues 29-1012 of SEQ ID NO:1 or a sequence at least 95% identical thereto;
   residues 1-980 of SEQ ID NO:1 or a sequence at least 95% identical thereto;
   residues 29-980 of SEQ ID NO:1 or a sequence at least 95% identical thereto;
   residues 1-568 of SEQ ID NO:1 or a sequence at least 95% identical thereto;
   residues 29-568 of SEQ ID NO:1 or a sequence at least 95% identical thereto;
   residues 34-549 of SEQ ID NO:1 or a sequence at least 95% identical thereto;
   SEQ ID NO:8 or a sequence at least 95% identical thereto;
   residues 29-549 of SEQ ID NO:8 or a sequence at least 95% identical thereto; and
   residues 34-549 of SEQ ID NO:8 or a sequence at least 95% identical thereto,
   and having at least one amino acid mutation in the catalytic domain of Klotho, wherein the isolated polypeptide inhibits IGF-1 signaling when expressed in MCF-7 cells in vitro, wherein said amino acid mutation is an amino acid substitution selected from the group consisting of Glu414Gln and Asp238Asn.

* * * * *

SEQUENCE LISTING

<160> NUMBER OF SEQ ID NOS: 85

<210> SEQ ID NO 1
<211> LENGTH: 1012
<212> TYPE: PRT
<213> ORGANISM: Homo_sapiens
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 1

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335
```

-continued

```
Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
```

```
                755                 760                 765
Asp Tyr Pro Trp Val Met Arg Asp Trp Leu Asn Gln Arg Asn Phe
770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Gly Val Gln Glu
                820                 825                 830
Met Thr Asp Ile Thr Trp Leu Asn Ser Pro Ser Gln Val Ala Val Val
                835                 840                 845
Pro Trp Gly Leu Arg Lys Val Leu Asn Trp Leu Lys Phe Lys Tyr Gly
850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
                900                 905                 910
Phe Ala Tyr Ser Phe Asn Asp Arg Thr Ala Pro Arg Phe Gly Leu Tyr
                915                 920                 925
Arg Tyr Ala Ala Asp Gln Phe Glu Pro Lys Ala Ser Met Lys His Tyr
                930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
His Thr Arg Lys Ser Leu Leu Ala Phe Ile Ala Phe Leu Phe Phe Ala
                980                 985                 990
Ser Ile Ile Ser Leu Ser Leu Ile Phe Tyr Tyr Ser Lys Lys Gly Arg
                995                 1000                1005
Arg Ser Tyr Lys
    1010

<210> SEQ ID NO 2
<211> LENGTH: 984
<212> TYPE: PRT
<213> ORGANISM: Artificial
<220> FEATURE:
<223> OTHER INFORMATION: residues 29-102 of SEQ ID NO:1

<400> SEQUENCE: 2

Arg Arg Leu Arg Ala Glu Pro Gly Asp Gly Ala Gln Thr Trp Ala Arg
1               5                   10                  15
Phe Ser Arg Pro Pro Ala Pro Glu Ala Ala Gly Leu Phe Gln Gly Thr
                20                  25                  30
Phe Pro Asp Gly Phe Leu Trp Ala Val Gly Ser Ala Ala Tyr Gln Thr
                35                  40                  45
Glu Gly Gly Trp Gln Gln His Gly Lys Gly Ala Ser Ile Trp Asp Thr
                50                  55                  60
Phe Thr His His Pro Leu Ala Pro Pro Gly Asp Ser Arg Asn Ala Ser
65                  70                  75                  80
Leu Pro Leu Gly Ala Pro Ser Pro Leu Gln Pro Ala Thr Gly Asp Val
                85                  90                  95
Ala Ser Asp Ser Tyr Asn Asn Val Phe Arg Asp Thr Glu Ala Leu Arg
```

```
            100                 105                 110
Glu Leu Gly Val Thr His Tyr Arg Phe Ser Ile Ser Trp Ala Arg Val
            115                 120                 125

Leu Pro Asn Gly Ser Ala Gly Val Pro Asn Arg Glu Gly Leu Arg Tyr
            130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
            195                 200                 205

Ile Asp Asn Pro Tyr Val Val Ala Trp His Gly Tyr Ala Thr Gly Arg
210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
            275                 280                 285

Gln Lys Ser Leu Asp Phe Val Leu Gly Trp Phe Ala Lys Pro Val Phe
            290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
            355                 360                 365

Leu Leu Ser Trp Ile Asp Leu Glu Phe Asn His Pro Gln Ile Phe Ile
            370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
            435                 440                 445

Phe Tyr Val Asp Phe Leu Ser Gln Asp Lys Met Leu Leu Pro Lys Ser
            450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
            500                 505                 510

Phe Thr Asp Leu Asn Val Tyr Leu Trp Asp Val His His Ser Lys Arg
            515                 520                 525
```

```
Leu Ile Lys Val Asp Gly Val Thr Lys Arg Lys Ser Tyr Cys
    530             535             540

Val Asp Phe Ala Ala Ile Gln Pro Gln Ile Ala Leu Leu Gln Glu Met
545             550             555             560

His Val Thr His Phe Arg Phe Ser Leu Asp Trp Ala Leu Ile Leu Pro
                565             570             575

Leu Gly Asn Gln Ser Gln Val Asn His Thr Ile Leu Gln Tyr Tyr Arg
            580             585             590

Cys Met Ala Ser Glu Leu Val Arg Val Asn Ile Thr Pro Val Val Ala
        595             600             605

Leu Trp Gln Pro Met Ala Pro Asn Gln Gly Leu Pro Arg Leu Leu Ala
    610             615             620

Arg Gln Gly Ala Trp Glu Asn Pro Tyr Thr Ala Leu Ala Phe Ala Glu
625             630             635             640

Tyr Ala Arg Leu Cys Phe Gln Glu Leu Gly His His Val Lys Leu Trp
                645             650             655

Ile Thr Met Asn Glu Pro Tyr Thr Arg Asn Met Thr Tyr Ser Ala Gly
            660             665             670

His Asn Leu Leu Lys Ala His Ala Leu Ala Trp His Val Tyr Asn Glu
        675             680             685

Lys Phe Arg His Ala Gln Asn Gly Lys Ile Ser Ile Ala Leu Gln Ala
    690             695             700

Asp Trp Ile Glu Pro Ala Cys Pro Phe Ser Gln Lys Asp Lys Glu Val
705             710             715             720

Ala Glu Arg Val Leu Glu Phe Asp Ile Gly Trp Leu Ala Glu Pro Ile
                725             730             735

Phe Gly Ser Gly Asp Tyr Pro Trp Val Met Arg Asp Trp Leu Asn Gln
            740             745             750

Arg Asn Asn Phe Leu Leu Pro Tyr Phe Thr Glu Asp Glu Lys Lys Leu
        755             760             765

Ile Gln Gly Thr Phe Asp Phe Leu Ala Leu Ser His Tyr Thr Thr Ile
    770             775             780

Leu Val Asp Ser Glu Lys Glu Asp Pro Ile Lys Tyr Asn Asp Tyr Leu
785             790             795             800

Glu Val Gln Glu Met Thr Asp Ile Thr Trp Leu Asn Ser Pro Ser Gln
                805             810             815

Val Ala Val Val Pro Trp Gly Leu Arg Lys Val Leu Asn Trp Leu Lys
            820             825             830

Phe Lys Tyr Gly Asp Leu Pro Met Tyr Ile Ile Ser Asn Gly Ile Asp
        835             840             845

Asp Gly Leu His Ala Glu Asp Asp Gln Leu Arg Val Tyr Tyr Met Gln
    850             855             860

Asn Tyr Ile Asn Glu Ala Leu Lys Ala His Ile Leu Asp Gly Ile Asn
865             870             875             880

Leu Cys Gly Tyr Phe Ala Tyr Ser Phe Asn Asp Arg Thr Ala Pro Arg
                885             890             895

Phe Gly Leu Tyr Arg Tyr Ala Ala Asp Gln Phe Glu Pro Lys Ala Ser
            900             905             910

Met Lys His Tyr Arg Lys Ile Ile Asp Ser Asn Gly Phe Pro Gly Pro
        915             920             925

Glu Thr Leu Glu Arg Phe Cys Pro Glu Glu Phe Thr Val Cys Thr Glu
    930             935             940
```

```
Cys Ser Phe Phe His Thr Arg Lys Ser Leu Leu Ala Phe Ile Ala Phe
945                 950                 955                 960

Leu Phe Phe Ala Ser Ile Ile Ser Leu Ser Leu Ile Phe Tyr Tyr Ser
                965                 970                 975

Lys Lys Gly Arg Arg Ser Tyr Lys
            980

<210> SEQ ID NO 3
<211> LENGTH: 980
<212> TYPE: PRT
<213> ORGANISM: Artificial
<220> FEATURE:
<223> OTHER INFORMATION: residues 1-980 of SEQ ID NO:1

<400> SEQUENCE: 3

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320
```

```
Asp Phe Val Leu Gly Trp Phe Ala Lys Pro Val Phe Ile Asp Gly Asp
            325                 330                 335

Tyr Pro Glu Ser Met Lys Asn Asn Leu Ser Ser Ile Leu Pro Asp Phe
        340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
```

```
                     740                 745                 750
Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
        850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
945                 950                 955                 960

Arg Phe Cys Pro Glu Gly Phe Thr Val Cys Thr Glu Cys Ser Phe Phe
                965                 970                 975

His Thr Arg Lys
            980

<210> SEQ ID NO 4
<211> LENGTH: 952
<212> TYPE: PRT
<213> ORGANISM: Artificial
<220> FEATURE:
<223> OTHER INFORMATION: residues 29-980 of SEQ ID NO:1

<400> SEQUENCE: 4

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
```

-continued

```
            115                 120                 125
Leu Pro Asn Gly Ser Ala Gly Val Pro Asn Arg Glu Gly Leu Arg Tyr
        130                 135                 140
Tyr Arg Arg Leu Leu Glu Arg Leu Arg Glu Leu Gly Val Gln Pro Val
145                 150                 155                 160
Val Thr Leu Tyr His Trp Asp Leu Pro Gln Arg Leu Gln Asp Ala Tyr
                165                 170                 175
Gly Gly Trp Ala Asn Arg Ala Leu Ala Asp His Phe Arg Asp Tyr Ala
            180                 185                 190
Glu Leu Cys Phe Arg His Phe Gly Gly Gln Val Lys Tyr Trp Ile Thr
        195                 200                 205
Ile Asp Asn Pro Tyr Val Val Ala Trp His Gly Tyr Ala Thr Gly Arg
    210                 215                 220
Leu Ala Pro Gly Ile Arg Gly Ser Pro Arg Leu Gly Tyr Leu Val Ala
225                 230                 235                 240
His Asn Leu Leu Leu Ala His Ala Lys Val Trp His Leu Tyr Asn Thr
                245                 250                 255
Ser Phe Arg Pro Thr Gln Gly Gly Gln Val Ser Ile Ala Leu Ser Ser
            260                 265                 270
His Trp Ile Asn Pro Arg Arg Met Thr Asp His Ser Ile Lys Glu Cys
        275                 280                 285
Gln Lys Ser Leu Asp Phe Val Leu Gly Trp Phe Ala Lys Pro Val Phe
    290                 295                 300
Ile Asp Gly Asp Tyr Pro Glu Ser Met Lys Asn Asn Leu Ser Ser Ile
305                 310                 315                 320
Leu Pro Asp Phe Thr Glu Ser Glu Lys Lys Phe Ile Lys Gly Thr Ala
                325                 330                 335
Asp Phe Phe Ala Leu Cys Phe Gly Pro Thr Leu Ser Phe Gln Leu Leu
            340                 345                 350
Asp Pro His Met Lys Phe Arg Gln Leu Glu Ser Pro Asn Leu Arg Gln
        355                 360                 365
Leu Leu Ser Trp Ile Asp Leu Glu Phe Asn His Pro Gln Ile Phe Ile
    370                 375                 380
Val Glu Asn Gly Trp Phe Val Ser Gly Thr Thr Lys Arg Asp Asp Ala
385                 390                 395                 400
Lys Tyr Met Tyr Tyr Leu Lys Lys Phe Ile Met Glu Thr Leu Lys Ala
                405                 410                 415
Ile Lys Leu Asp Gly Val Asp Val Ile Gly Tyr Thr Ala Trp Ser Leu
            420                 425                 430
Met Asp Gly Phe Glu Trp His Arg Gly Tyr Ser Ile Arg Arg Gly Leu
        435                 440                 445
Phe Tyr Val Asp Phe Leu Ser Gln Asp Lys Met Leu Leu Pro Lys Ser
    450                 455                 460
Ser Ala Leu Phe Tyr Gln Lys Leu Ile Glu Lys Asn Gly Phe Pro Pro
465                 470                 475                 480
Leu Pro Glu Asn Gln Pro Leu Glu Gly Thr Phe Pro Cys Asp Phe Ala
                485                 490                 495
Trp Gly Val Val Asp Asn Tyr Ile Gln Val Asp Thr Thr Leu Ser Gln
            500                 505                 510
Phe Thr Asp Leu Asn Val Tyr Leu Trp Asp Val His His Ser Lys Arg
        515                 520                 525
Leu Ile Lys Val Asp Gly Val Val Thr Lys Lys Arg Lys Ser Tyr Cys
    530                 535                 540
```

```
Val Asp Phe Ala Ala Ile Gln Pro Gln Ile Ala Leu Leu Gln Glu Met
545                 550                 555                 560

His Val Thr His Phe Arg Phe Ser Leu Asp Trp Ala Leu Ile Leu Pro
                565                 570                 575

Leu Gly Asn Gln Ser Gln Val Asn His Thr Ile Leu Gln Tyr Tyr Arg
            580                 585                 590

Cys Met Ala Ser Glu Leu Val Arg Val Asn Ile Thr Pro Val Val Ala
        595                 600                 605

Leu Trp Gln Pro Met Ala Pro Asn Gln Gly Leu Pro Arg Leu Leu Ala
    610                 615                 620

Arg Gln Gly Ala Trp Glu Asn Pro Tyr Thr Ala Leu Ala Phe Ala Glu
625                 630                 635                 640

Tyr Ala Arg Leu Cys Phe Gln Glu Leu Gly His His Val Lys Leu Trp
                645                 650                 655

Ile Thr Met Asn Glu Pro Tyr Thr Arg Asn Met Thr Tyr Ser Ala Gly
                660                 665                 670

His Asn Leu Leu Lys Ala His Ala Leu Ala Trp His Val Tyr Asn Glu
            675                 680                 685

Lys Phe Arg His Ala Gln Asn Gly Lys Ile Ser Ile Ala Leu Gln Ala
690                 695                 700

Asp Trp Ile Glu Pro Ala Cys Pro Phe Ser Gln Lys Asp Lys Glu Val
705                 710                 715                 720

Ala Glu Arg Val Leu Glu Phe Asp Ile Gly Trp Leu Ala Glu Pro Ile
                725                 730                 735

Phe Gly Ser Gly Asp Tyr Pro Trp Val Met Arg Asp Trp Leu Asn Gln
            740                 745                 750

Arg Asn Asn Phe Leu Leu Pro Tyr Phe Thr Glu Asp Glu Lys Lys Leu
            755                 760                 765

Ile Gln Gly Thr Phe Asp Phe Leu Ala Leu Ser His Tyr Thr Thr Ile
    770                 775                 780

Leu Val Asp Ser Glu Lys Glu Asp Pro Ile Lys Tyr Asn Asp Tyr Leu
785                 790                 795                 800

Glu Val Gln Glu Met Thr Asp Ile Thr Trp Leu Asn Ser Pro Ser Gln
                805                 810                 815

Val Ala Val Pro Trp Gly Leu Arg Lys Val Leu Asn Trp Leu Lys
            820                 825                 830

Phe Lys Tyr Gly Asp Leu Pro Met Tyr Ile Ile Ser Asn Gly Ile Asp
        835                 840                 845

Asp Gly Leu His Ala Glu Asp Gln Leu Arg Val Tyr Tyr Met Gln
    850                 855                 860

Asn Tyr Ile Asn Glu Ala Leu Lys Ala His Ile Leu Asp Gly Ile Asn
865                 870                 875                 880

Leu Cys Gly Tyr Phe Ala Tyr Ser Phe Asn Asp Arg Thr Ala Pro Arg
            885                 890                 895

Phe Gly Leu Tyr Arg Tyr Ala Ala Asp Gln Phe Glu Pro Lys Ala Ser
        900                 905                 910

Met Lys His Tyr Arg Lys Ile Ile Asp Ser Asn Gly Phe Pro Gly Pro
    915                 920                 925

Glu Thr Leu Glu Arg Phe Cys Pro Glu Glu Phe Thr Val Cys Thr Glu
    930                 935                 940

Cys Ser Phe Phe His Thr Arg Lys
945                 950
```

<210> SEQ ID NO 5
<211> LENGTH: 568
<212> TYPE: PRT
<213> ORGANISM: Artificial
<220> FEATURE:
<223> OTHER INFORMATION: residues 1-568 of SEQ ID NO:1

<400> SEQUENCE: 5

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365
```

```
Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg
                565

<210> SEQ ID NO 6
<211> LENGTH: 540
<212> TYPE: PRT
<213> ORGANISM: Artificial
<220> FEATURE:
<223> OTHER INFORMATION: residues 29-568 of SEQ ID NO:1

<400> SEQUENCE: 6

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
                20                  25                  30

Phe Pro Asp Gly Phe Leu Trp Ala Val Gly Ser Ala Ala Tyr Gln Thr
                35                  40                  45

Glu Gly Gly Trp Gln Gln His Gly Lys Gly Ala Ser Ile Trp Asp Thr
50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
                100                 105                 110

Glu Leu Gly Val Thr His Tyr Arg Phe Ser Ile Ser Trp Ala Arg Val
                115                 120                 125

Leu Pro Asn Gly Ser Ala Gly Val Pro Asn Arg Glu Gly Leu Arg Tyr
                130                 135                 140

Tyr Arg Arg Leu Leu Glu Arg Leu Arg Glu Leu Gly Val Gln Pro Val
145                 150                 155                 160
```

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Asp Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
    370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
    450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
            500                 505                 510

Phe Thr Asp Leu Asn Val Tyr Leu Trp Asp Val His Ser Lys Arg
        515                 520                 525

Leu Ile Lys Val Asp Gly Val Val Thr Lys Lys Arg
    530                 535                 540

<210> SEQ ID NO 7
<211> LENGTH: 516
<212> TYPE: PRT
<213> ORGANISM: Artificial
<220> FEATURE:
<223> OTHER INFORMATION: residues 34-549 of SEQ ID NO:1

<400> SEQUENCE: 7

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
```

```
            405                 410                 415
Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
            450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp
            515

<210> SEQ ID NO 8
<211> LENGTH: 549
<212> TYPE: PRT
<213> ORGANISM: Homo sapiens
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 8

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
```

```
                225                 230                 235                 240
        Tyr Val Val Ala Trp His Gly Tyr Ala Thr Gly Arg Leu Ala Pro Gly
                        245                 250                 255

Ile Arg Gly Ser Pro Arg Leu Gly Tyr Leu Val Ala His Asn Leu Leu
                        260                 265                 270

Leu Ala His Ala Lys Val Trp His Leu Tyr Asn Thr Ser Phe Arg Pro
                        275                 280                 285

Thr Gln Gly Gly Gln Val Ser Ile Ala Leu Ser Ser His Trp Ile Asn
                        290                 295                 300

Pro Arg Arg Met Thr Asp His Ser Ile Lys Glu Cys Gln Lys Ser Leu
        305                 310                 315                 320

Asp Phe Val Leu Gly Trp Phe Ala Lys Pro Val Phe Ile Asp Gly Asp
                        325                 330                 335

Tyr Pro Glu Ser Met Lys Asn Asn Leu Ser Ser Ile Leu Pro Asp Phe
                        340                 345                 350

Thr Glu Ser Glu Lys Lys Phe Ile Lys Gly Thr Ala Asp Phe Phe Ala
                        355                 360                 365

Leu Cys Phe Gly Pro Thr Leu Ser Phe Gln Leu Leu Asp Pro His Met
                        370                 375                 380

Lys Phe Arg Gln Leu Glu Ser Pro Asn Leu Arg Gln Leu Leu Ser Trp
        385                 390                 395                 400

Ile Asp Leu Glu Phe Asn His Pro Gln Ile Phe Ile Val Glu Asn Gly
                        405                 410                 415

Trp Phe Val Ser Gly Thr Thr Lys Arg Asp Asp Ala Lys Tyr Met Tyr
                        420                 425                 430

Tyr Leu Lys Lys Phe Ile Met Glu Thr Leu Lys Ala Ile Lys Leu Asp
                        435                 440                 445

Gly Val Asp Val Ile Gly Tyr Thr Ala Trp Ser Leu Met Asp Gly Phe
                        450                 455                 460

Glu Trp His Arg Gly Tyr Ser Ile Arg Arg Gly Leu Phe Tyr Val Asp
        465                 470                 475                 480

Phe Leu Ser Gln Asp Lys Met Leu Leu Pro Lys Ser Ser Ala Leu Phe
                        485                 490                 495

Tyr Gln Lys Leu Ile Glu Lys Asn Gly Phe Pro Leu Pro Glu Asn
                        500                 505                 510

Gln Pro Leu Glu Gly Thr Phe Pro Cys Asp Phe Ala Trp Gly Val Val
                        515                 520                 525

Asp Asn Tyr Ile Gln Val Ser Gln Leu Thr Lys Pro Ile Ser Ser Leu
                        530                 535                 540

Thr Lys Pro Tyr His
        545

<210> SEQ ID NO 9
<211> LENGTH: 521
<212> TYPE: PRT
<213> ORGANISM: Artificial
<220> FEATURE:
<223> OTHER INFORMATION: residues 29-549 of SEQ ID NO:8

<400> SEQUENCE: 9

Arg Arg Leu Arg Ala Glu Pro Gly Asp Gly Ala Gln Thr Trp Ala Arg
        1               5                   10                  15

Phe Ser Arg Pro Pro Ala Pro Glu Ala Ala Gly Leu Phe Gln Gly Thr
                        20                  25                  30

Phe Pro Asp Gly Phe Leu Trp Ala Val Gly Ser Ala Ala Tyr Gln Thr
```

```
            35                  40                  45
Glu Gly Gly Trp Gln Gln His Gly Lys Gly Ala Ser Ile Trp Asp Thr
 50                  55                  60

Phe Thr His His Pro Leu Ala Pro Pro Gly Asp Ser Arg Asn Ala Ser
 65                  70                  75                  80

Leu Pro Leu Gly Ala Pro Ser Pro Leu Gln Pro Ala Thr Gly Asp Val
                 85                  90                  95

Ala Ser Asp Ser Tyr Asn Asn Val Phe Arg Asp Thr Glu Ala Leu Arg
                100                 105                 110

Glu Leu Gly Val Thr His Tyr Arg Phe Ser Ile Ser Trp Ala Arg Val
            115                 120                 125

Leu Pro Asn Gly Ser Ala Gly Val Pro Asn Arg Glu Gly Leu Arg Tyr
        130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Asp Asn Pro Tyr Val Val Ala Trp His Gly Tyr Ala Thr Gly Arg
210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
450                 455                 460
```

```
Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
            485                 490                 495

Trp Gly Val Val Asp Asn Tyr Ile Gln Val Ser Gln Leu Thr Lys Pro
                500                 505                 510

Ile Ser Ser Leu Thr Lys Pro Tyr His
        515                 520

<210> SEQ ID NO 10
<211> LENGTH: 516
<212> TYPE: PRT
<213> ORGANISM: Artificial
<220> FEATURE:
<223> OTHER INFORMATION: residues 34-549 of SEQ ID NO:8

<400> SEQUENCE: 10

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300
```

```
Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
            325                 330                 335

Cys Phe Gly Pro Thr Leu Ser Phe Gln Leu Leu Asp Pro His Met Lys
        340                 345                 350

Phe Arg Gln Leu Glu Ser Pro Asn Leu Arg Gln Leu Leu Ser Trp Ile
    355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Ser Gln Leu Thr Lys Pro Ile Ser Ser Leu Thr
            500                 505                 510

Lys Pro Tyr His
        515

<210> SEQ ID NO 11
<211> LENGTH: 1012
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (414)..(414)
<223> OTHER INFORMATION: Xaa can be any naturally occurring amino acid

<400> SEQUENCE: 11

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
```

```
                115                 120                 125
Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
530                 535                 540
```

-continued

```
Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960
```

```
Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 12
<211> LENGTH: 942
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (344)..(344)
<223> OTHER INFORMATION: Xaa can be any naturally occurring amino acid

<400> SEQUENCE: 12

Ser Ala Ala Tyr Gln Thr Glu Gly Gly Trp Gln Gln His Gly Lys Gly
1               5                   10                  15

Ala Ser Ile Trp Asp Thr Phe Thr His Pro Leu Ala Pro Pro Gly
            20                  25                  30

Asp Ser Arg Asn Ala Ser Leu Pro Leu Gly Ala Pro Ser Pro Leu Gln
        35                  40                  45

Pro Ala Thr Gly Asp Val Ala Ser Asp Ser Tyr Asn Asn Val Phe Arg
    50                  55                  60

Asp Thr Glu Ala Leu Arg Glu Leu Gly Val Thr His Tyr Arg Phe Ser
65                  70                  75                  80

Ile Ser Trp Ala Arg Val Leu Pro Asn Gly Ser Ala Gly Val Pro Asn
                85                  90                  95

Arg Glu Gly Leu Arg Tyr Tyr Arg Arg Leu Leu Glu Arg Leu Arg Glu
            100                 105                 110

Leu Gly Val Gln Pro Val Val Thr Leu Tyr His Trp Asp Leu Pro Gln
        115                 120                 125

Arg Leu Gln Asp Ala Tyr Gly Gly Trp Ala Asn Arg Ala Leu Ala Asp
    130                 135                 140

His Phe Arg Asp Tyr Ala Glu Leu Cys Phe Arg His Phe Gly Gly Gln
145                 150                 155                 160

Val Lys Tyr Trp Ile Thr Ile Asp Asn Pro Tyr Val Val Ala Trp His
                165                 170                 175

Gly Tyr Ala Thr Gly Arg Leu Ala Pro Gly Ile Arg Gly Ser Pro Arg
            180                 185                 190

Leu Gly Tyr Leu Val Ala His Asn Leu Leu Leu Ala His Ala Lys Val
        195                 200                 205

Trp His Leu Tyr Asn Thr Ser Phe Arg Pro Thr Gln Gly Gly Gln Val
    210                 215                 220

Ser Ile Ala Leu Ser Ser His Trp Ile Asn Pro Arg Arg Met Thr Asp
225                 230                 235                 240

His Ser Ile Lys Glu Cys Gln Lys Ser Leu Asp Phe Val Leu Gly Trp
                245                 250                 255

Phe Ala Lys Pro Val Phe Ile Asp Gly Asp Tyr Pro Glu Ser Met Lys
            260                 265                 270

Asn Asn Leu Ser Ser Ile Leu Pro Asp Phe Thr Glu Ser Glu Lys Lys
        275                 280                 285
```

```
Phe Ile Lys Gly Thr Ala Asp Phe Ala Leu Cys Phe Gly Pro Thr
    290                 295                 300

Leu Ser Phe Gln Leu Leu Asp Pro His Met Lys Phe Arg Gln Leu Glu
305                 310                 315                 320

Ser Pro Asn Leu Arg Gln Leu Leu Ser Trp Ile Asp Leu Glu Phe Asn
                325                 330                 335

His Pro Gln Ile Phe Ile Val Xaa Asn Gly Trp Phe Val Ser Gly Thr
            340                 345                 350

Thr Lys Arg Asp Asp Ala Lys Tyr Met Tyr Tyr Leu Lys Lys Phe Ile
        355                 360                 365

Met Glu Thr Leu Lys Ala Ile Lys Leu Asp Gly Val Asp Val Ile Gly
370                 375                 380

Tyr Thr Ala Trp Ser Leu Met Asp Gly Phe Glu Trp His Arg Gly Tyr
385                 390                 395                 400

Ser Ile Arg Arg Gly Leu Phe Tyr Val Asp Phe Leu Ser Gln Asp Lys
                405                 410                 415

Met Leu Leu Pro Lys Ser Ser Ala Leu Phe Tyr Gln Lys Leu Ile Glu
            420                 425                 430

Lys Asn Gly Phe Pro Pro Leu Pro Glu Asn Gln Pro Leu Glu Gly Thr
        435                 440                 445

Phe Pro Cys Asp Phe Ala Trp Gly Val Val Asp Asn Tyr Ile Gln Val
450                 455                 460

Asp Thr Thr Leu Ser Gln Phe Thr Asp Leu Asn Val Tyr Leu Trp Asp
465                 470                 475                 480

Val His His Ser Lys Arg Leu Ile Lys Val Asp Gly Val Val Thr Lys
                485                 490                 495

Lys Arg Lys Ser Tyr Cys Val Asp Phe Ala Ala Ile Gln Pro Gln Ile
            500                 505                 510

Ala Leu Leu Gln Glu Met His Val Thr His Phe Arg Phe Ser Leu Asp
        515                 520                 525

Trp Ala Leu Ile Leu Pro Leu Gly Asn Gln Ser Gln Val Asn His Thr
530                 535                 540

Ile Leu Gln Tyr Tyr Arg Cys Met Ala Ser Glu Leu Val Arg Val Asn
545                 550                 555                 560

Ile Thr Pro Val Val Ala Leu Trp Gln Pro Met Ala Pro Asn Gln Gly
                565                 570                 575

Leu Pro Arg Leu Leu Ala Arg Gln Gly Ala Trp Glu Asn Pro Tyr Thr
            580                 585                 590

Ala Leu Ala Phe Ala Glu Tyr Ala Arg Leu Cys Phe Gln Glu Leu Gly
        595                 600                 605

His His Val Lys Leu Trp Ile Thr Met Asn Glu Pro Tyr Thr Arg Asn
610                 615                 620

Met Thr Tyr Ser Ala Gly His Asn Leu Leu Lys Ala His Ala Leu Ala
625                 630                 635                 640

Trp His Val Tyr Asn Glu Lys Phe Arg His Ala Gln Asn Gly Lys Ile
                645                 650                 655

Ser Ile Ala Leu Gln Ala Asp Trp Ile Glu Pro Ala Cys Pro Phe Ser
            660                 665                 670

Gln Lys Asp Lys Glu Val Ala Glu Arg Val Leu Glu Phe Asp Ile Gly
        675                 680                 685

Trp Leu Ala Glu Pro Ile Phe Gly Ser Gly Asp Tyr Pro Trp Val Met
690                 695                 700
```

-continued

```
Arg Asp Trp Leu Asn Gln Arg Asn Asn Phe Leu Leu Pro Tyr Phe Thr
705                 710                 715                 720

Glu Asp Glu Lys Lys Leu Ile Gln Gly Thr Phe Asp Phe Leu Ala Leu
            725                 730                 735

Ser His Tyr Thr Thr Ile Leu Val Asp Ser Glu Lys Glu Asp Pro Ile
        740                 745                 750

Lys Tyr Asn Asp Tyr Leu Glu Val Gln Glu Met Thr Asp Ile Thr Trp
    755                 760                 765

Leu Asn Ser Pro Ser Gln Val Ala Val Pro Trp Gly Leu Arg Lys
770                 775                 780

Val Leu Asn Trp Leu Lys Phe Lys Tyr Gly Asp Leu Pro Met Tyr Ile
785                 790                 795                 800

Ile Ser Asn Gly Ile Asp Asp Gly Leu His Ala Glu Asp Asp Gln Leu
                805                 810                 815

Arg Val Tyr Tyr Met Gln Asn Tyr Ile Asn Glu Ala Leu Lys Ala His
            820                 825                 830

Ile Leu Asp Gly Ile Asn Leu Cys Gly Tyr Phe Ala Tyr Ser Phe Asn
        835                 840                 845

Asp Arg Thr Ala Pro Arg Phe Gly Leu Tyr Arg Tyr Ala Ala Asp Gln
    850                 855                 860

Phe Glu Pro Lys Ala Ser Met Lys His Tyr Arg Lys Ile Ile Asp Ser
865                 870                 875                 880

Asn Gly Phe Pro Gly Pro Glu Thr Leu Glu Arg Phe Cys Pro Glu Glu
                885                 890                 895

Phe Thr Val Cys Thr Glu Cys Ser Phe Phe His Thr Arg Lys Ser Leu
            900                 905                 910

Leu Ala Phe Ile Ala Phe Leu Phe Ala Ser Ile Ile Ser Leu Ser
        915                 920                 925

Leu Ile Phe Tyr Tyr Ser Lys Lys Gly Arg Arg Ser Tyr Lys
    930                 935                 940

<210> SEQ ID NO 13
<211> LENGTH: 980
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (414)..(414)
<223> OTHER INFORMATION: Xaa can be any naturally occurring amino acid

<400> SEQUENCE: 13

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
            85                  90                  95

Pro Leu Ala Pro Pro Gly Asp Ser Arg Asn Ala Ser Leu Pro Leu Gly
        100                 105                 110
```

```
Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525
```

-continued

```
Asp Asn Tyr Ile Gln Val Asp Thr Thr Leu Ser Gln Phe Thr Asp Leu
    530                 535                 540
Asn Val Tyr Leu Trp Asp Val His His Ser Lys Arg Leu Ile Lys Val
545                 550                 555                 560
Asp Gly Val Val Thr Lys Arg Lys Ser Tyr Cys Val Asp Phe Ala
                565                 570                 575
Ala Ile Gln Pro Gln Ile Ala Leu Leu Gln Glu Met His Val Thr His
                580                 585                 590
Phe Arg Phe Ser Leu Asp Trp Ala Leu Ile Leu Pro Leu Gly Asn Gln
    595                 600                 605
Ser Gln Val Asn His Thr Ile Leu Gln Tyr Tyr Arg Cys Met Ala Ser
    610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
                660                 665                 670
Cys Phe Gln Glu Leu Gly His His Val Lys Leu Trp Ile Thr Met Asn
    675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
                740                 745                 750
Leu Glu Phe Asp Ile Gly Trp Leu Ala Glu Pro Ile Phe Gly Ser Gly
    755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
                820                 825                 830
Met Thr Asp Ile Thr Trp Leu Asn Ser Pro Ser Gln Val Ala Val Val
    835                 840                 845
Pro Trp Gly Leu Arg Lys Val Leu Asn Trp Leu Lys Phe Lys Tyr Gly
850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
                900                 905                 910
Phe Ala Tyr Ser Phe Asn Asp Arg Thr Ala Pro Arg Phe Gly Leu Tyr
    915                 920                 925
Arg Tyr Ala Ala Asp Gln Phe Glu Pro Lys Ala Ser Met Lys His Tyr
    930                 935                 940
Arg Lys Ile Ile Asp Ser Asn Gly Phe Pro Gly Pro Glu Thr Leu Glu
```

```
                945                 950                 955                 960
Arg Phe Cys Pro Glu Glu Phe Thr Val Cys Thr Glu Cys Ser Phe Phe
                    965                 970                 975

His Thr Arg Lys
            980

<210> SEQ ID NO 14
<211> LENGTH: 952
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (386)..(386)
<223> OTHER INFORMATION: Xaa can be any naturally occurring amino acid

<400> SEQUENCE: 14

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
                20                  25                  30

Phe Pro Asp Gly Phe Leu Trp Ala Val Gly Ser Ala Ala Tyr Gln Thr
            35                  40                  45

Glu Gly Gly Trp Gln Gln His Gly Lys Gly Ala Ser Ile Trp Asp Thr
        50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Asp Asn Pro Tyr Val Val Ala Trp His Gly Tyr Ala Thr Gly Arg
210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
290                 295                 300
```

```
Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
                340                 345                 350

Asp Pro His Met Lys Phe Arg Gln Leu Glu Ser Pro Asn Leu Arg Gln
                355                 360                 365

Leu Leu Ser Trp Ile Asp Leu Glu Phe Asn His Pro Gln Ile Phe Ile
        370                 375                 380

Val Xaa Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
                420                 425                 430

Met Asp Gly Phe Glu Trp His Arg Gly Tyr Ser Ile Arg Arg Gly Leu
                435                 440                 445

Phe Tyr Val Asp Phe Leu Ser Gln Asp Lys Met Leu Leu Pro Lys Ser
        450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
                500                 505                 510

Phe Thr Asp Leu Asn Val Tyr Leu Trp Asp Val His His Ser Lys Arg
        515                 520                 525

Leu Ile Lys Val Asp Gly Val Val Thr Lys Arg Lys Ser Tyr Cys
530                 535                 540

Val Asp Phe Ala Ala Ile Gln Pro Gln Ile Ala Leu Leu Gln Glu Met
545                 550                 555                 560

His Val Thr His Phe Arg Phe Ser Leu Asp Trp Ala Leu Ile Leu Pro
                565                 570                 575

Leu Gly Asn Gln Ser Gln Val Asn His Thr Ile Leu Gln Tyr Tyr Arg
                580                 585                 590

Cys Met Ala Ser Glu Leu Val Arg Val Asn Ile Thr Pro Val Val Ala
                595                 600                 605

Leu Trp Gln Pro Met Ala Pro Asn Gln Gly Leu Pro Arg Leu Leu Ala
        610                 615                 620

Arg Gln Gly Ala Trp Glu Asn Pro Tyr Thr Ala Leu Ala Phe Ala Glu
625                 630                 635                 640

Tyr Ala Arg Leu Cys Phe Gln Glu Leu Gly His His Val Lys Leu Trp
                645                 650                 655

Ile Thr Met Asn Glu Pro Tyr Thr Arg Asn Met Thr Tyr Ser Ala Gly
                660                 665                 670

His Asn Leu Leu Lys Ala His Ala Leu Ala Trp His Val Tyr Asn Glu
                675                 680                 685

Lys Phe Arg His Ala Gln Asn Gly Lys Ile Ser Ile Ala Leu Gln Ala
                690                 695                 700

Asp Trp Ile Glu Pro Ala Cys Pro Phe Ser Gln Lys Asp Lys Glu Val
705                 710                 715                 720

Ala Glu Arg Val Leu Glu Phe Asp Ile Gly Trp Leu Ala Glu Pro Ile
```

```
                725                 730                 735
Phe Gly Ser Gly Asp Tyr Pro Trp Val Met Arg Asp Trp Leu Asn Gln
            740                 745                 750
Arg Asn Asn Phe Leu Leu Pro Tyr Phe Thr Glu Asp Glu Lys Lys Leu
        755                 760                 765
Ile Gln Gly Thr Phe Asp Phe Leu Ala Leu Ser His Tyr Thr Thr Ile
    770                 775                 780
Leu Val Asp Ser Glu Lys Glu Asp Pro Ile Lys Tyr Asn Asp Tyr Leu
785                 790                 795                 800
Glu Val Gln Glu Met Thr Asp Ile Thr Trp Leu Asn Ser Pro Ser Gln
            805                 810                 815
Val Ala Val Val Pro Trp Gly Leu Arg Lys Val Leu Asn Trp Leu Lys
        820                 825                 830
Phe Lys Tyr Gly Asp Leu Pro Met Tyr Ile Ile Ser Asn Gly Ile Asp
    835                 840                 845
Asp Gly Leu His Ala Glu Asp Asp Gln Leu Arg Val Tyr Tyr Met Gln
850                 855                 860
Asn Tyr Ile Asn Glu Ala Leu Lys Ala His Ile Leu Asp Gly Ile Asn
865                 870                 875                 880
Leu Cys Gly Tyr Phe Ala Tyr Ser Phe Asn Asp Arg Thr Ala Pro Arg
            885                 890                 895
Phe Gly Leu Tyr Arg Tyr Ala Ala Asp Gln Phe Glu Pro Lys Ala Ser
        900                 905                 910
Met Lys His Tyr Arg Lys Ile Ile Asp Ser Asn Gly Phe Pro Gly Pro
    915                 920                 925
Glu Thr Leu Glu Arg Phe Cys Pro Glu Glu Phe Thr Val Cys Thr Glu
    930                 935                 940
Cys Ser Phe Phe His Thr Arg Lys
945                 950
```

<210> SEQ ID NO 15
<211> LENGTH: 568
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (414)..(414)
<223> OTHER INFORMATION: Xaa can be any naturally occurring amino acid

<400> SEQUENCE: 15

```
Met Pro Ala Ser Ala Pro Pro Arg Arg Pro Arg Pro Pro Pro Pro Ser
1               5                   10                  15
Leu Ser Leu Leu Leu Val Leu Leu Gly Leu Gly Gly Arg Arg Leu Arg
            20                  25                  30
Ala Glu Pro Gly Asp Gly Ala Gln Thr Trp Ala Arg Phe Ser Arg Pro
        35                  40                  45
Pro Ala Pro Glu Ala Ala Gly Leu Phe Gln Gly Thr Phe Pro Asp Gly
    50                  55                  60
Phe Leu Trp Ala Val Gly Ser Ala Ala Tyr Gln Thr Glu Gly Gly Trp
65                  70                  75                  80
Gln Gln His Gly Lys Gly Ala Ser Ile Trp Asp Thr Phe Thr His His
            85                  90                  95
Pro Leu Ala Pro Pro Gly Asp Ser Arg Asn Ala Ser Leu Pro Leu Gly
        100                 105                 110
```

-continued

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu

```
                530               535               540
Asn Val Tyr Leu Trp Asp Val His His Ser Lys Arg Leu Ile Lys Val
545                 550               555               560

Asp Gly Val Val Thr Lys Lys Arg
                565

<210> SEQ ID NO 16
<211> LENGTH: 540
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (386)..(386)
<223> OTHER INFORMATION: Xaa can be any naturally occurring amino acid

<400> SEQUENCE: 16

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Asp Asn Pro Tyr Val Val Ala Trp His Gly Tyr Ala Thr Gly Arg
210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
290                 295                 300
```

```
Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
            325                 330                 335

Asp Phe Phe Ala Leu Cys Phe Gly Pro Thr Leu Ser Phe Gln Leu Leu
        340                 345                 350

Asp Pro His Met Lys Phe Arg Gln Leu Glu Ser Pro Asn Leu Arg Gln
    355                 360                 365

Leu Leu Ser Trp Ile Asp Leu Glu Phe Asn His Pro Gln Ile Phe Ile
370                 375                 380

Val Xaa Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
            405                 410                 415

Ile Lys Leu Asp Gly Val Asp Val Ile Gly Tyr Thr Ala Trp Ser Leu
        420                 425                 430

Met Asp Gly Phe Glu Trp His Arg Gly Tyr Ser Ile Arg Arg Gly Leu
    435                 440                 445

Phe Tyr Val Asp Phe Leu Ser Gln Asp Lys Met Leu Leu Pro Lys Ser
450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
            485                 490                 495

Trp Gly Val Val Asp Asn Tyr Ile Gln Val Asp Thr Thr Leu Ser Gln
        500                 505                 510

Phe Thr Asp Leu Asn Val Tyr Leu Trp Asp Val His Ser Lys Arg
    515                 520                 525

Leu Ile Lys Val Asp Gly Val Val Thr Lys Lys Arg
530                 535                 540

<210> SEQ ID NO 17
<211> LENGTH: 516
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (381)..(381)
<223> OTHER INFORMATION: Xaa can be any naturally occurring amino acid

<400> SEQUENCE: 17

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
            85                  90                  95

Asn Asn Val Phe Arg Asp Thr Glu Ala Leu Arg Glu Leu Gly Val Thr
        100                 105                 110
```

```
His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
            195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
            275                 280                 285

Phe Val Leu Gly Trp Phe Ala Lys Pro Val Phe Ile Asp Gly Asp Tyr
            290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Xaa Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp
            515
```

<210> SEQ ID NO 18
<211> LENGTH: 549
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (414)..(414)
<223> OTHER INFORMATION: Xaa can be any naturally occurring amino acid

<400> SEQUENCE: 18

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350
```

```
Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Ser Gln Leu Thr Lys Pro Ile Ser Ser Leu
            530                 535                 540

Thr Lys Pro Tyr His
545

<210> SEQ ID NO 19
<211> LENGTH: 521
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (386)..(386)
<223> OTHER INFORMATION: Xaa can be any naturally occurring amino acid

<400> SEQUENCE: 19

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
            35                  40                  45

Glu Gly Gly Trp Gln Gln His Gly Lys Gly Ala Ser Ile Trp Asp Thr
50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
            85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
            115                 120                 125

Leu Pro Asn Gly Ser Ala Gly Val Pro Asn Arg Glu Gly Leu Arg Tyr
```

130                 135                 140
Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Asp Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
                260                 265                 270

His Trp Ile Asn Pro Arg Arg Met Thr Asp His Ser Ile Lys Glu Cys
            275                 280                 285

Gln Lys Ser Leu Asp Phe Val Leu Gly Trp Phe Ala Lys Pro Val Phe
        290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
    370                 375                 380

Val Xaa Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Ser Gln Leu Thr Lys Pro
            500                 505                 510

Ile Ser Ser Leu Thr Lys Pro Tyr His
        515                 520

<210> SEQ ID NO 20
<211> LENGTH: 516
<212> TYPE: PRT
<213> ORGANISM: Artificial

```
<220> FEATURE:
<223> OTHER INFORMATION: variant polypeptide
<220> FEATURE:
<221> NAME/KEY: misc_feature
<222> LOCATION: (381)..(381)
<223> OTHER INFORMATION: Xaa can be any naturally occurring amino acid

<400> SEQUENCE: 20

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Xaa Asn Gly Trp
```

-continued

```
            370                 375                 380
Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
            450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Ser Gln Leu Thr Lys Pro Ile Ser Ser Leu Thr
            500                 505                 510

Lys Pro Tyr His
        515

<210> SEQ ID NO 21
<211> LENGTH: 1012
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (238)..(238)
<223> OTHER INFORMATION: Xaa can be any naturally occurring amino acid

<400> SEQUENCE: 21

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Arg
            20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190
```

-continued

```
His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
            245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
            325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
            370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
```

```
              610                 615                 620
Glu Leu Val Arg Val Asn Ile Thr Pro Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
            690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
            850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
            995                 1000                1005

Arg Ser Tyr Lys
    1010

<210> SEQ ID NO 22
```

-continued

```
<211> LENGTH: 984
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (210)..(210)
<223> OTHER INFORMATION: Xaa can be any naturally occurring amino acid

<400> SEQUENCE: 22

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
```

-continued

```
            355                 360                 365
Leu Leu Ser Trp Ile Asp Leu Glu Phe Asn His Pro Gln Ile Phe Ile
    370                 375                 380
Val Glu Asn Gly Trp Phe Val Ser Gly Thr Thr Lys Arg Asp Asp Ala
385                 390                 395                 400
Lys Tyr Met Tyr Tyr Leu Lys Lys Phe Ile Met Glu Thr Leu Lys Ala
                    405                 410                 415
Ile Lys Leu Asp Gly Val Asp Val Ile Gly Tyr Thr Ala Trp Ser Leu
                420                 425                 430
Met Asp Gly Phe Glu Trp His Arg Gly Tyr Ser Ile Arg Arg Gly Leu
            435                 440                 445
Phe Tyr Val Asp Phe Leu Ser Gln Asp Lys Met Leu Leu Pro Lys Ser
        450                 455                 460
Ser Ala Leu Phe Tyr Gln Lys Leu Ile Glu Lys Asn Gly Phe Pro Pro
465                 470                 475                 480
Leu Pro Glu Asn Gln Pro Leu Glu Gly Thr Phe Pro Cys Asp Phe Ala
                    485                 490                 495
Trp Gly Val Val Asp Asn Tyr Ile Gln Val Asp Thr Thr Leu Ser Gln
                500                 505                 510
Phe Thr Asp Leu Asn Val Tyr Leu Trp Asp Val His Ser Lys Arg
            515                 520                 525
Leu Ile Lys Val Asp Gly Val Val Thr Lys Arg Lys Ser Tyr Cys
        530                 535                 540
Val Asp Phe Ala Ala Ile Gln Pro Gln Ile Ala Leu Leu Gln Glu Met
545                 550                 555                 560
His Val Thr His Phe Arg Phe Ser Leu Asp Trp Ala Leu Ile Leu Pro
                    565                 570                 575
Leu Gly Asn Gln Ser Gln Val Asn His Thr Ile Leu Gln Tyr Tyr Arg
                580                 585                 590
Cys Met Ala Ser Glu Leu Val Arg Val Asn Ile Thr Pro Val Val Ala
            595                 600                 605
Leu Trp Gln Pro Met Ala Pro Asn Gln Gly Leu Pro Arg Leu Leu Ala
        610                 615                 620
Arg Gln Gly Ala Trp Glu Asn Pro Tyr Thr Ala Leu Ala Phe Ala Glu
625                 630                 635                 640
Tyr Ala Arg Leu Cys Phe Gln Glu Leu Gly His His Val Lys Leu Trp
                    645                 650                 655
Ile Thr Met Asn Glu Pro Tyr Thr Arg Asn Met Thr Tyr Ser Ala Gly
                660                 665                 670
His Asn Leu Leu Lys Ala His Ala Leu Ala Trp His Val Tyr Asn Glu
            675                 680                 685
Lys Phe Arg His Ala Gln Asn Gly Lys Ile Ser Ile Ala Leu Gln Ala
        690                 695                 700
Asp Trp Ile Glu Pro Ala Cys Pro Phe Ser Gln Lys Asp Lys Glu Val
705                 710                 715                 720
Ala Glu Arg Val Leu Glu Phe Asp Ile Gly Trp Leu Ala Glu Pro Ile
                    725                 730                 735
Phe Gly Ser Gly Asp Tyr Pro Trp Val Met Arg Asp Trp Leu Asn Gln
                740                 745                 750
Arg Asn Asn Phe Leu Leu Pro Tyr Phe Thr Glu Asp Glu Lys Lys Leu
            755                 760                 765
Ile Gln Gly Thr Phe Asp Phe Leu Ala Leu Ser His Tyr Thr Thr Ile
        770                 775                 780
```

```
Leu Val Asp Ser Glu Lys Glu Asp Pro Ile Lys Tyr Asn Asp Tyr Leu
785                 790                 795                 800

Glu Val Gln Glu Met Thr Asp Ile Thr Trp Leu Asn Ser Pro Ser Gln
                805                 810                 815

Val Ala Val Pro Trp Gly Leu Arg Lys Val Leu Asn Trp Leu Lys
            820                 825                 830

Phe Lys Tyr Gly Asp Leu Pro Met Tyr Ile Ile Ser Asn Gly Ile Asp
            835                 840                 845

Asp Gly Leu His Ala Glu Asp Gln Leu Arg Val Tyr Tyr Met Gln
            850                 855                 860

Asn Tyr Ile Asn Glu Ala Leu Lys Ala His Ile Leu Asp Gly Ile Asn
865                 870                 875                 880

Leu Cys Gly Tyr Phe Ala Tyr Ser Phe Asn Asp Arg Thr Ala Pro Arg
                885                 890                 895

Phe Gly Leu Tyr Arg Tyr Ala Ala Asp Gln Phe Glu Pro Lys Ala Ser
            900                 905                 910

Met Lys His Tyr Arg Lys Ile Ile Asp Ser Asn Gly Phe Pro Gly Pro
            915                 920                 925

Glu Thr Leu Glu Arg Phe Cys Pro Glu Glu Phe Thr Val Cys Thr Glu
            930                 935                 940

Cys Ser Phe Phe His Thr Arg Lys Ser Leu Leu Ala Phe Ile Ala Phe
945                 950                 955                 960

Leu Phe Phe Ala Ser Ile Ile Ser Leu Ser Leu Ile Phe Tyr Tyr Ser
                965                 970                 975

Lys Lys Gly Arg Arg Ser Tyr Lys
            980

<210> SEQ ID NO 23
<211> LENGTH: 980
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (238)..(238)
<223> OTHER INFORMATION: Xaa can be any naturally occurring amino acid

<400> SEQUENCE: 23

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
```

```
            130                 135                 140
Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
                450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560
```

```
Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975
```

```
His Thr Arg Lys
            980

<210> SEQ ID NO 24
<211> LENGTH: 952
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (210)..(210)
<223> OTHER INFORMATION: Xaa can be any naturally occurring amino acid

<400> SEQUENCE: 24

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
                20                  25                  30

Phe Pro Asp Gly Phe Leu Trp Ala Val Gly Ser Ala Ala Tyr Gln Thr
            35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335
```

```
Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
            355                 360                 365

Leu Leu Ser Trp Ile Asp Leu Glu Phe Asn His Pro Gln Ile Phe Ile
370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
            435                 440                 445

Phe Tyr Val Asp Phe Leu Ser Gln Asp Lys Met Leu Leu Pro Lys Ser
    450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
            500                 505                 510

Phe Thr Asp Leu Asn Val Tyr Leu Trp Asp Val His His Ser Lys Arg
            515                 520                 525

Leu Ile Lys Val Asp Gly Val Val Thr Lys Lys Arg Lys Ser Tyr Cys
    530                 535                 540

Val Asp Phe Ala Ala Ile Gln Pro Gln Ile Ala Leu Leu Gln Glu Met
545                 550                 555                 560

His Val Thr His Phe Arg Phe Ser Leu Asp Trp Ala Leu Ile Leu Pro
                565                 570                 575

Leu Gly Asn Gln Ser Gln Val Asn His Thr Ile Leu Gln Tyr Tyr Arg
            580                 585                 590

Cys Met Ala Ser Glu Leu Val Arg Val Asn Ile Thr Pro Val Val Ala
            595                 600                 605

Leu Trp Gln Pro Met Ala Pro Asn Gln Gly Leu Pro Arg Leu Leu Ala
    610                 615                 620

Arg Gln Gly Ala Trp Glu Asn Pro Tyr Thr Ala Leu Ala Phe Ala Glu
625                 630                 635                 640

Tyr Ala Arg Leu Cys Phe Gln Glu Leu Gly His His Val Lys Leu Trp
                645                 650                 655

Ile Thr Met Asn Glu Pro Tyr Thr Arg Asn Met Thr Tyr Ser Ala Gly
            660                 665                 670

His Asn Leu Leu Lys Ala His Ala Leu Ala Trp His Val Tyr Asn Glu
            675                 680                 685

Lys Phe Arg His Ala Gln Asn Gly Lys Ile Ser Ile Ala Leu Gln Ala
    690                 695                 700

Asp Trp Ile Glu Pro Ala Cys Pro Phe Ser Gln Lys Asp Lys Glu Val
705                 710                 715                 720

Ala Glu Arg Val Leu Glu Phe Asp Ile Gly Trp Leu Ala Glu Pro Ile
                725                 730                 735

Phe Gly Ser Gly Asp Tyr Pro Trp Val Met Arg Asp Trp Leu Asn Gln
            740                 745                 750
```

```
Arg Asn Asn Phe Leu Leu Pro Tyr Phe Thr Glu Asp Glu Lys Lys Leu
            755                 760                 765

Ile Gln Gly Thr Phe Asp Phe Leu Ala Leu Ser His Tyr Thr Thr Ile
    770                 775                 780

Leu Val Asp Ser Glu Lys Glu Asp Pro Ile Lys Tyr Asn Asp Tyr Leu
785                 790                 795                 800

Glu Val Gln Glu Met Thr Asp Ile Thr Trp Leu Asn Ser Pro Ser Gln
                805                 810                 815

Val Ala Val Val Pro Trp Gly Leu Arg Lys Val Leu Asn Trp Leu Lys
                820                 825                 830

Phe Lys Tyr Gly Asp Leu Pro Met Tyr Ile Ile Ser Asn Gly Ile Asp
        835                 840                 845

Asp Gly Leu His Ala Glu Asp Asp Gln Leu Arg Val Tyr Tyr Met Gln
        850                 855                 860

Asn Tyr Ile Asn Glu Ala Leu Lys Ala His Ile Leu Asp Gly Ile Asn
865                 870                 875                 880

Leu Cys Gly Tyr Phe Ala Tyr Ser Phe Asn Asp Arg Thr Ala Pro Arg
                885                 890                 895

Phe Gly Leu Tyr Arg Tyr Ala Ala Asp Gln Phe Glu Pro Lys Ala Ser
                900                 905                 910

Met Lys His Tyr Arg Lys Ile Ile Asp Ser Asn Gly Phe Pro Gly Pro
        915                 920                 925

Glu Thr Leu Glu Arg Phe Cys Pro Glu Glu Phe Thr Val Cys Thr Glu
        930                 935                 940

Cys Ser Phe Phe His Thr Arg Lys
945                 950

<210> SEQ ID NO 25
<211> LENGTH: 568
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (238)..(238)
<223> OTHER INFORMATION: Xaa can be any naturally occurring amino acid

<400> SEQUENCE: 25

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140
```

```
Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Arg Arg Leu
            165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His Ser Lys Arg Leu Ile Lys Val
545                 550                 555                 560
```

Asp Gly Val Val Thr Lys Lys Arg
            565

<210> SEQ ID NO 26
<211> LENGTH: 540
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (210)..(210)
<223> OTHER INFORMATION: Xaa can be any naturally occurring amino acid

<400> SEQUENCE: 26

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
                20                  25                  30

Phe Pro Asp Gly Phe Leu Trp Ala Val Gly Ser Ala Ala Tyr Gln Thr
            35                  40                  45

Glu Gly Gly Trp Gln Gln His Gly Lys Gly Ala Ser Ile Trp Asp Thr
        50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

```
Asp Phe Phe Ala Leu Cys Phe Gly Pro Thr Leu Ser Phe Gln Leu Leu
                340                 345                 350

Asp Pro His Met Lys Phe Arg Gln Leu Glu Ser Pro Asn Leu Arg Gln
            355                 360                 365

Leu Leu Ser Trp Ile Asp Leu Glu Phe Asn His Pro Gln Ile Phe Ile
        370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
            500                 505                 510

Phe Thr Asp Leu Asn Val Tyr Leu Trp Asp Val His His Ser Lys Arg
        515                 520                 525

Leu Ile Lys Val Asp Gly Val Val Thr Lys Lys Arg
        530                 535                 540

<210> SEQ ID NO 27
<211> LENGTH: 516
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (205)..(205)
<223> OTHER INFORMATION: Xaa can be any naturally occurring amino acid

<400> SEQUENCE: 27

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
```

```
                130                 135                 140
Glu Arg Leu Arg Glu Leu Gly Val Gln Pro Val Thr Leu Tyr His
145                 150                 155                 160

Trp Asp Leu Pro Gln Arg Leu Gln Asp Ala Tyr Gly Trp Ala Asn
                165                 170                 175

Arg Ala Leu Ala Asp His Phe Arg Asp Tyr Ala Glu Leu Cys Phe Arg
                180                 185                 190

His Phe Gly Gly Gln Val Lys Tyr Trp Ile Thr Ile Xaa Asn Pro Tyr
                195                 200                 205

Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
                260                 265                 270

Arg Arg Met Thr Asp His Ser Ile Lys Glu Cys Gln Lys Ser Leu Asp
                275                 280                 285

Phe Val Leu Gly Trp Phe Ala Lys Pro Val Phe Ile Asp Gly Asp Tyr
290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
                355                 360                 365

Asp Leu Glu Phe Asn His Pro Gln Ile Phe Ile Val Glu Asn Gly Trp
                370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp
            515

<210> SEQ ID NO 28
<211> LENGTH: 549
<212> TYPE: PRT
<213> ORGANISM: Artificial
```

<220> FEATURE:
<223> OTHER INFORMATION: variant polypeptide
<220> FEATURE:
<221> NAME/KEY: misc_feature
<222> LOCATION: (238)..(238)
<223> OTHER INFORMATION: Xaa can be any naturally occurring amino acid

<400> SEQUENCE: 28

Met Pro Ala Ser Ala Pro Pro Arg Arg Pro Arg Pro Pro Pro Ser
1               5                  10                  15

Leu Ser Leu Leu Leu Val Leu Leu Gly Leu Gly Arg Arg Leu Arg
            20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met

```
                    370                 375                 380
Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                    405                 410                 415

Trp Phe Val Ser Gly Thr Thr Lys Arg Asp Asp Ala Lys Tyr Met Tyr
                    420                 425                 430

Tyr Leu Lys Lys Phe Ile Met Glu Thr Leu Lys Ala Ile Lys Leu Asp
                    435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                    485                 490                 495

Tyr Gln Lys Leu Ile Glu Lys Asn Gly Phe Pro Pro Leu Pro Glu Asn
                    500                 505                 510

Gln Pro Leu Glu Gly Thr Phe Pro Cys Asp Phe Ala Trp Gly Val Val
                    515                 520                 525

Asp Asn Tyr Ile Gln Val Ser Gln Leu Thr Lys Pro Ile Ser Ser Leu
530                 535                 540

Thr Lys Pro Tyr His
545

<210> SEQ ID NO 29
<211> LENGTH: 521
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (210)..(210)
<223> OTHER INFORMATION: Xaa can be any naturally occurring amino acid

<400> SEQUENCE: 29

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
                20                  25                  30

Phe Pro Asp Gly Phe Leu Trp Ala Val Gly Ser Ala Ala Tyr Gln Thr
            35                  40                  45

Glu Gly Gly Trp Gln Gln His Gly Lys Gly Ala Ser Ile Trp Asp Thr
50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
                100                 105                 110

Glu Leu Gly Val Thr His Tyr Arg Phe Ser Ile Ser Trp Ala Arg Val
            115                 120                 125

Leu Pro Asn Gly Ser Ala Gly Val Pro Asn Arg Glu Gly Leu Arg Tyr
        130                 135                 140

Tyr Arg Arg Leu Leu Glu Arg Leu Arg Glu Leu Gly Val Gln Pro Val
145                 150                 155                 160
```

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
370                 375                 380

Val Glu Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Ser Gln Leu Thr Lys Pro
            500                 505                 510

Ile Ser Ser Leu Thr Lys Pro Tyr His
        515                 520

<210> SEQ ID NO 30
<211> LENGTH: 516
<212> TYPE: PRT
<213> ORGANISM: Artificial
<220> FEATURE:
<223> OTHER INFORMATION: variant polypeptide
<220> FEATURE:
<221> NAME/KEY: misc_feature
<222> LOCATION: (205)..(205)

<223> OTHER INFORMATION: Xaa can be any naturally occurring amino acid

<400> SEQUENCE: 30

```
Glu Pro Gly Asp Gly Ala Gln Thr Trp Ala Arg Phe Ser Arg Pro Pro
1               5                   10                  15
Ala Pro Glu Ala Ala Gly Leu Phe Gln Gly Thr Phe Pro Asp Gly Phe
            20                  25                  30
Leu Trp Ala Val Gly Ser Ala Ala Tyr Gln Thr Glu Gly Gly Trp Gln
        35                  40                  45
Gln His Gly Lys Gly Ala Ser Ile Trp Asp Thr Phe Thr His His Pro
    50                  55                  60
Leu Ala Pro Pro Gly Asp Ser Arg Asn Ala Ser Leu Pro Leu Gly Ala
65                  70                  75                  80
Pro Ser Pro Leu Gln Pro Ala Thr Gly Asp Val Ala Ser Asp Ser Tyr
                85                  90                  95
Asn Asn Val Phe Arg Asp Thr Glu Ala Leu Arg Glu Leu Gly Val Thr
            100                 105                 110
His Tyr Arg Phe Ser Ile Ser Trp Ala Arg Val Leu Pro Asn Gly Ser
        115                 120                 125
Ala Gly Val Pro Asn Arg Glu Gly Leu Arg Tyr Tyr Arg Arg Leu Leu
    130                 135                 140
Glu Arg Leu Arg Glu Leu Gly Val Gln Pro Val Val Thr Leu Tyr His
145                 150                 155                 160
Trp Asp Leu Pro Gln Arg Leu Gln Asp Ala Tyr Gly Gly Trp Ala Asn
                165                 170                 175
Arg Ala Leu Ala Asp His Phe Arg Asp Tyr Ala Glu Leu Cys Phe Arg
            180                 185                 190
His Phe Gly Gly Gln Val Lys Tyr Trp Ile Thr Ile Xaa Asn Pro Tyr
        195                 200                 205
Val Val Ala Trp His Gly Tyr Ala Thr Gly Arg Leu Ala Pro Gly Ile
    210                 215                 220
Arg Gly Ser Pro Arg Leu Gly Tyr Leu Val Ala His Asn Leu Leu Leu
225                 230                 235                 240
Ala His Ala Lys Val Trp His Leu Tyr Asn Thr Ser Phe Arg Pro Thr
                245                 250                 255
Gln Gly Gly Gln Val Ser Ile Ala Leu Ser Ser His Trp Ile Asn Pro
            260                 265                 270
Arg Arg Met Thr Asp His Ser Ile Lys Glu Cys Gln Lys Ser Leu Asp
        275                 280                 285
Phe Val Leu Gly Trp Phe Ala Lys Pro Val Phe Ile Asp Gly Asp Tyr
    290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                325                 330                 335
Cys Phe Gly Pro Thr Leu Ser Phe Gln Leu Leu Asp Pro His Met Lys
            340                 345                 350
Phe Arg Gln Leu Glu Ser Pro Asn Leu Arg Gln Leu Leu Ser Trp Ile
        355                 360                 365
Asp Leu Glu Phe Asn His Pro Gln Ile Phe Ile Val Glu Asn Gly Trp
    370                 375                 380
Phe Val Ser Gly Thr Thr Lys Arg Asp Asp Ala Lys Tyr Met Tyr Tyr
385                 390                 395                 400
```

-continued

```
Leu Lys Lys Phe Ile Met Glu Thr Leu Lys Ala Ile Lys Leu Asp Gly
            405                 410                 415

Val Asp Val Ile Gly Tyr Thr Ala Trp Ser Leu Met Asp Gly Phe Glu
        420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Ser Gln Leu Thr Lys Pro Ile Ser Ser Leu Thr
            500                 505                 510

Lys Pro Tyr His
        515

<210> SEQ ID NO 31
<211> LENGTH: 1012
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (238)..(238)
<223> OTHER INFORMATION: L-Asp of residue 238 is substituted with
      an alpha-amino acid different from L-Asp.
<220> FEATURE:
<221> NAME/KEY: MOD_RES
<222> LOCATION: (414)..(414)
<223> OTHER INFORMATION: L-Glu of residue 414 is substituted with
      an alpha-amino acid residue different from L-Glu

<400> SEQUENCE: 31

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
            85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190
```

```
His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
        580                 585                 590

Phe Arg Phe Ser Leu Asp Trp Ala Leu Ile Leu Pro Leu Gly Asn Gln
        595                 600                 605
```

```
Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010
```

-continued

```
<210> SEQ ID NO 32
<211> LENGTH: 984
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (210)..(210)
<223> OTHER INFORMATION: L-Asp of residue 210 is substituted with an a
      pha-amino acid residue different from L-Glu
<220> FEATURE:
<221> NAME/KEY: MOD_RES
<222> LOCATION: (386)..(386)
<223> OTHER INFORMATION: L-Glu of residue 386 is substituted with an
      alpha-amino acid different from L-Glu.

<400> SEQUENCE: 32

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320
```

-continued

```
Leu Pro Asp Phe Thr Glu Ser Glu Lys Lys Phe Ile Lys Gly Thr Ala
                325                 330                 335
Asp Phe Phe Ala Leu Cys Phe Gly Pro Thr Leu Ser Phe Gln Leu Leu
            340                 345                 350
Asp Pro His Met Lys Phe Arg Gln Leu Glu Ser Pro Asn Leu Arg Gln
        355                 360                 365
Leu Leu Ser Trp Ile Asp Leu Glu Phe Asn His Pro Gln Ile Phe Ile
    370                 375                 380
Val Xaa Asn Gly Trp Phe Val Ser Gly Thr Thr Lys Arg Asp Asp Ala
385                 390                 395                 400
Lys Tyr Met Tyr Tyr Leu Lys Phe Ile Met Glu Thr Leu Lys Ala
                405                 410                 415
Ile Lys Leu Asp Gly Val Asp Val Ile Gly Tyr Thr Ala Trp Ser Leu
            420                 425                 430
Met Asp Gly Phe Glu Trp His Arg Gly Tyr Ser Ile Arg Arg Gly Leu
        435                 440                 445
Phe Tyr Val Asp Phe Leu Ser Gln Asp Lys Met Leu Leu Pro Lys Ser
    450                 455                 460
Ser Ala Leu Phe Tyr Gln Lys Leu Ile Glu Lys Asn Gly Phe Pro Pro
465                 470                 475                 480
Leu Pro Glu Asn Gln Pro Leu Glu Gly Thr Phe Pro Cys Asp Phe Ala
                485                 490                 495
Trp Gly Val Val Asp Asn Tyr Ile Gln Val Asp Thr Thr Leu Ser Gln
            500                 505                 510
Phe Thr Asp Leu Asn Val Tyr Leu Trp Asp Val His His Ser Lys Arg
        515                 520                 525
Leu Ile Lys Val Asp Gly Val Val Thr Lys Arg Lys Ser Tyr Cys
    530                 535                 540
Val Asp Phe Ala Ala Ile Gln Pro Gln Ile Ala Leu Leu Gln Glu Met
545                 550                 555                 560
His Val Thr His Phe Arg Phe Ser Leu Asp Trp Ala Leu Ile Leu Pro
                565                 570                 575
Leu Gly Asn Gln Ser Gln Val Asn His Thr Ile Leu Gln Tyr Tyr Arg
            580                 585                 590
Cys Met Ala Ser Glu Leu Val Arg Val Asn Ile Thr Pro Val Val Ala
        595                 600                 605
Leu Trp Gln Pro Met Ala Pro Asn Gln Gly Leu Pro Arg Leu Leu Ala
    610                 615                 620
Arg Gln Gly Ala Trp Glu Asn Pro Tyr Thr Ala Leu Ala Phe Ala Glu
625                 630                 635                 640
Tyr Ala Arg Leu Cys Phe Gln Glu Leu Gly His His Val Lys Leu Trp
                645                 650                 655
Ile Thr Met Asn Glu Pro Tyr Thr Arg Asn Met Thr Tyr Ser Ala Gly
            660                 665                 670
His Asn Leu Leu Lys Ala His Ala Leu Ala Trp His Val Tyr Asn Glu
        675                 680                 685
Lys Phe Arg His Ala Gln Asn Gly Lys Ile Ser Ile Ala Leu Gln Ala
    690                 695                 700
Asp Trp Ile Glu Pro Ala Cys Pro Phe Ser Gln Lys Asp Lys Glu Val
705                 710                 715                 720
Ala Glu Arg Val Leu Glu Phe Asp Ile Gly Trp Leu Ala Glu Pro Ile
                725                 730                 735
Phe Gly Ser Gly Asp Tyr Pro Trp Val Met Arg Asp Trp Leu Asn Gln
```

```
                   740                 745                 750
Arg Asn Asn Phe Leu Leu Pro Tyr Phe Thr Glu Asp Glu Lys Lys Leu
            755                 760                 765

Ile Gln Gly Thr Phe Asp Phe Leu Ala Leu Ser His Tyr Thr Thr Ile
        770                 775                 780

Leu Val Asp Ser Glu Lys Glu Asp Pro Ile Lys Tyr Asn Asp Tyr Leu
785                 790                 795                 800

Glu Val Gln Glu Met Thr Asp Ile Thr Trp Leu Asn Ser Pro Ser Gln
                805                 810                 815

Val Ala Val Val Pro Trp Gly Leu Arg Lys Val Leu Asn Trp Leu Lys
            820                 825                 830

Phe Lys Tyr Gly Asp Leu Pro Met Tyr Ile Ile Ser Asn Gly Ile Asp
        835                 840                 845

Asp Gly Leu His Ala Glu Asp Asp Gln Leu Arg Val Tyr Tyr Met Gln
850                 855                 860

Asn Tyr Ile Asn Glu Ala Leu Lys Ala His Ile Leu Asp Gly Ile Asn
865                 870                 875                 880

Leu Cys Gly Tyr Phe Ala Tyr Ser Phe Asn Asp Arg Thr Ala Pro Arg
                885                 890                 895

Phe Gly Leu Tyr Arg Tyr Ala Ala Asp Gln Phe Glu Pro Lys Ala Ser
            900                 905                 910

Met Lys His Tyr Arg Lys Ile Ile Asp Ser Asn Gly Phe Pro Gly Pro
        915                 920                 925

Glu Thr Leu Glu Arg Phe Cys Pro Glu Phe Thr Val Cys Thr Glu
    930                 935                 940

Cys Ser Phe Phe His Thr Arg Lys Ser Leu Leu Ala Phe Ile Ala Phe
945                 950                 955                 960

Leu Phe Phe Ala Ser Ile Ile Ser Leu Ser Leu Ile Phe Tyr Tyr Ser
                965                 970                 975

Lys Lys Gly Arg Arg Ser Tyr Lys
            980

<210> SEQ ID NO 33
<211> LENGTH: 980
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (238)..(238)
<223> OTHER INFORMATION: L-Asp of residue 238 is substituted with an
      alpha-amino acid different from L-Asp.
<220> FEATURE:
<221> NAME/KEY: MOD_RES
<222> LOCATION: (414)..(414)
<223> OTHER INFORMATION: L-Glu of residue 414 is substituted with an
      alpha-amino acid residue different from L-Glu

<400> SEQUENCE: 33

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60
```

```
Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glx Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
```

```
            485                 490                 495
Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
            850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910
```

-continued

```
Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys
            980

<210> SEQ ID NO 34
<211> LENGTH: 952
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (210)..(210)
<223> OTHER INFORMATION: L-Asp of residue 238 is substituted with an
      alpha-amino acid different from L-Asp.
<220> FEATURE:
<221> NAME/KEY: MOD_RES
<222> LOCATION: (210)..(210)
<223> OTHER INFORMATION: L-Asp of residue 210 is substituted with an
      alpha-amino acid different from L-Asp.
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: MOD_RES
<222> LOCATION: (414)..(414)
<223> OTHER INFORMATION: L-Glu of residue 414 is substituted with an
      alpha-amino acid residue different from L-Glu

<400> SEQUENCE: 34

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
```

```
                180             185             190
Glu Leu Cys Phe Arg His Phe Gly Gly Gln Val Lys Tyr Trp Ile Thr
            195             200             205
Ile Xaa Asn Pro Tyr Val Val Ala Trp His Gly Tyr Ala Thr Gly Arg
210             215             220
Leu Ala Pro Gly Ile Arg Gly Ser Pro Arg Leu Gly Tyr Leu Val Ala
225             230             235             240
His Asn Leu Leu Leu Ala His Ala Lys Val Trp His Leu Tyr Asn Thr
            245             250             255
Ser Phe Arg Pro Thr Gln Gly Gly Gln Val Ser Ile Ala Leu Ser Ser
            260             265             270
His Trp Ile Asn Pro Arg Arg Met Thr Asp His Ser Ile Lys Glu Cys
            275             280             285
Gln Lys Ser Leu Asp Phe Val Leu Gly Trp Phe Ala Lys Pro Val Phe
            290             295             300
Ile Asp Gly Asp Tyr Pro Glu Ser Met Lys Asn Asn Leu Ser Ser Ile
305             310             315             320
Leu Pro Asp Phe Thr Glu Ser Glu Lys Lys Phe Ile Lys Gly Thr Ala
                325             330             335
Asp Phe Phe Ala Leu Cys Phe Gly Pro Thr Leu Ser Phe Gln Leu Leu
            340             345             350
Asp Pro His Met Lys Phe Arg Gln Leu Glu Ser Pro Asn Leu Arg Gln
            355             360             365
Leu Leu Ser Trp Ile Asp Leu Glu Phe Asn His Pro Gln Ile Phe Ile
            370             375             380
Val Xaa Asn Gly Trp Phe Val Ser Gly Thr Thr Lys Arg Asp Asp Ala
385             390             395             400
Lys Tyr Met Tyr Tyr Leu Lys Lys Phe Ile Met Glu Thr Leu Lys Ala
                405             410             415
Ile Lys Leu Asp Gly Val Asp Val Ile Gly Tyr Thr Ala Trp Ser Leu
            420             425             430
Met Asp Gly Phe Glu Trp His Arg Gly Tyr Ser Ile Arg Arg Gly Leu
            435             440             445
Phe Tyr Val Asp Phe Leu Ser Gln Asp Lys Met Leu Leu Pro Lys Ser
            450             455             460
Ser Ala Leu Phe Tyr Gln Lys Leu Ile Glu Lys Asn Gly Phe Pro Pro
465             470             475             480
Leu Pro Glu Asn Gln Pro Leu Glu Gly Thr Phe Pro Cys Asp Phe Ala
                485             490             495
Trp Gly Val Val Asp Asn Tyr Ile Gln Val Asp Thr Thr Leu Ser Gln
            500             505             510
Phe Thr Asp Leu Asn Val Tyr Leu Trp Asp Val His His Ser Lys Arg
            515             520             525
Leu Ile Lys Val Asp Gly Val Val Thr Lys Arg Lys Ser Tyr Cys
            530             535             540
Val Asp Phe Ala Ala Ile Gln Pro Gln Ile Ala Leu Leu Gln Glu Met
545             550             555             560
His Val Thr His Phe Arg Phe Ser Leu Asp Trp Ala Leu Ile Leu Pro
                565             570             575
Leu Gly Asn Gln Ser Gln Val Asn His Thr Ile Leu Gln Tyr Tyr Arg
            580             585             590
Cys Met Ala Ser Glu Leu Val Arg Val Asn Ile Thr Pro Val Val Ala
            595             600             605
```

```
Leu Trp Gln Pro Met Ala Pro Asn Gln Gly Leu Pro Arg Leu Leu Ala
        610                 615                 620

Arg Gln Gly Ala Trp Glu Asn Pro Tyr Thr Ala Leu Ala Phe Ala Glu
625                 630                 635                 640

Tyr Ala Arg Leu Cys Phe Gln Glu Leu Gly His His Val Lys Leu Trp
                645                 650                 655

Ile Thr Met Asn Glu Pro Tyr Thr Arg Asn Met Thr Tyr Ser Ala Gly
            660                 665                 670

His Asn Leu Leu Lys Ala His Ala Leu Ala Trp His Val Tyr Asn Glu
        675                 680                 685

Lys Phe Arg His Ala Gln Asn Gly Lys Ile Ser Ile Ala Leu Gln Ala
690                 695                 700

Asp Trp Ile Glu Pro Ala Cys Pro Phe Ser Gln Lys Asp Lys Glu Val
705                 710                 715                 720

Ala Glu Arg Val Leu Glu Phe Asp Ile Gly Trp Leu Ala Glu Pro Ile
                725                 730                 735

Phe Gly Ser Gly Asp Tyr Pro Trp Val Met Arg Asp Trp Leu Asn Gln
            740                 745                 750

Arg Asn Asn Phe Leu Leu Pro Tyr Phe Thr Glu Asp Glu Lys Lys Leu
        755                 760                 765

Ile Gln Gly Thr Phe Asp Phe Leu Ala Leu Ser His Tyr Thr Thr Ile
770                 775                 780

Leu Val Asp Ser Glu Lys Glu Asp Pro Ile Lys Tyr Asn Asp Tyr Leu
785                 790                 795                 800

Glu Val Gln Glu Met Thr Asp Ile Thr Trp Leu Asn Ser Pro Ser Gln
                805                 810                 815

Val Ala Val Val Pro Trp Gly Leu Arg Lys Val Leu Asn Trp Leu Lys
            820                 825                 830

Phe Lys Tyr Gly Asp Leu Pro Met Tyr Ile Ile Ser Asn Gly Ile Asp
        835                 840                 845

Asp Gly Leu His Ala Glu Asp Asp Gln Leu Arg Val Tyr Tyr Met Gln
850                 855                 860

Asn Tyr Ile Asn Glu Ala Leu Lys Ala His Ile Leu Asp Gly Ile Asn
865                 870                 875                 880

Leu Cys Gly Tyr Phe Ala Tyr Ser Phe Asn Asp Arg Thr Ala Pro Arg
                885                 890                 895

Phe Gly Leu Tyr Arg Tyr Ala Ala Asp Gln Phe Glu Pro Lys Ala Ser
            900                 905                 910

Met Lys His Tyr Arg Lys Ile Ile Asp Ser Asn Gly Phe Pro Gly Pro
        915                 920                 925

Glu Thr Leu Glu Arg Phe Cys Pro Glu Glu Phe Thr Val Cys Thr Glu
930                 935                 940

Cys Ser Phe Phe His Thr Arg Lys
945                 950

<210> SEQ ID NO 35
<211> LENGTH: 568
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (238)..(238)
<223> OTHER INFORMATION: L-Asp of residue 238 is substituted with an
      alpha-amino acid different from L-Asp.
```

```
<220> FEATURE:
<221> NAME/KEY: MOD_RES
<222> LOCATION: (414)..(414)
<223> OTHER INFORMATION: L-Glu of residue 414 is substituted with an
      alpha-amino acid residue different from L-Glu

<400> SEQUENCE: 35

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65              70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380
```

-continued

```
Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
            405                 410                 415

Trp Phe Val Ser Gly Thr Thr Lys Arg Asp Asp Ala Lys Tyr Met Tyr
        420                 425                 430

Tyr Leu Lys Lys Phe Ile Met Glu Thr Leu Lys Ala Ile Lys Leu Asp
    435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495

Tyr Gln Lys Leu Ile Glu Lys Asn Gly Phe Pro Pro Leu Pro Glu Asn
        500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg
                565

<210> SEQ ID NO 36
<211> LENGTH: 540
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (210)..(210)
<223> OTHER INFORMATION: L-Asp of residue 210 is substituted with an
      alpha-amino acid different from L-Asp.
<220> FEATURE:
<221> NAME/KEY: MOD_RES
<222> LOCATION: (386)..(386)
<223> OTHER INFORMATION: L-Glu of residue 386 is substituted with an
      alpha-amino acid residue different from L-Glu

<400> SEQUENCE: 36

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
    50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
            85                  90                  95

Ala Ser Asp Ser Tyr Asn Asn Val Phe Arg Asp Thr Glu Ala Leu Arg
        100                 105                 110

Glu Leu Gly Val Thr His Tyr Arg Phe Ser Ile Ser Trp Ala Arg Val
```

```
            115                 120                 125
Leu Pro Asn Gly Ser Ala Gly Val Pro Asn Arg Glu Gly Leu Arg Tyr
        130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270

His Trp Ile Asn Pro Arg Arg Met Thr Asp His Ser Ile Lys Glu Cys
        275                 280                 285

Gln Lys Ser Leu Asp Phe Val Leu Gly Trp Phe Ala Lys Pro Val Phe
    290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
    370                 375                 380

Val Xaa Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
    450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Asp Thr Thr Leu Ser Gln
            500                 505                 510

Phe Thr Asp Leu Asn Val Tyr Leu Trp Asp Val His His Ser Lys Arg
        515                 520                 525

Leu Ile Lys Val Asp Gly Val Val Thr Lys Lys Arg
    530                 535                 540
```

<210> SEQ ID NO 37
<211> LENGTH: 516
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (205)..(205)
<223> OTHER INFORMATION: L-Asp of residue 205 is substituted with an alpha-amino acid different from L-Asp.
<220> FEATURE:
<221> NAME/KEY: MOD_RES
<222> LOCATION: (381)..(381)
<223> OTHER INFORMATION: L-Glu of residue 381 is substituted with an alpha-amino acid residue different from L-Glu

<400> SEQUENCE: 37

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Xaa Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
```

```
            305                 310                 315                 320
    Glu Ser Glu Lys Lys Phe Ile Lys Gly Thr Ala Asp Phe Phe Ala Leu
                    325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
                355                 360                 365

Asp Leu Glu Phe Asn His Pro Gln Ile Phe Ile Val Xaa Asn Gly Trp
        370                 375                 380

Phe Val Ser Gly Thr Thr Lys Arg Asp Asp Ala Lys Tyr Met Tyr Tyr
    385                 390                 395                 400

Leu Lys Lys Phe Ile Met Glu Thr Leu Lys Ala Ile Lys Leu Asp Gly
                    405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
        450                 455                 460

Gln Lys Leu Ile Glu Lys Asn Gly Phe Pro Pro Leu Pro Glu Asn Gln
    465                 470                 475                 480

Pro Leu Glu Gly Thr Phe Pro Cys Asp Phe Ala Trp Gly Val Val Asp
                    485                 490                 495

Asn Tyr Ile Gln Val Asp Thr Thr Leu Ser Gln Phe Thr Asp Leu Asn
                500                 505                 510

Val Tyr Leu Trp
            515

<210> SEQ ID NO 38
<211> LENGTH: 549
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (238)..(238)
<223> OTHER INFORMATION: L-Asp of residue 238 is substituted with an
      alpha-amino acid different from L-Asp.
<220> FEATURE:
<221> NAME/KEY: MOD_RES
<222> LOCATION: (414)..(414)
<223> OTHER INFORMATION: L-Glu of residue 414 is substituted with an
      alpha-amino acid residue different from L-Glu

<400> SEQUENCE: 38

Met Pro Ala Ser Ala Pro Pro Arg Arg Pro Arg Pro Pro Pro Pro Ser
    1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
    65                  70                  75                  80

Gln Gln His Gly Lys Gly Ala Ser Ile Trp Asp Thr Phe Thr His His
                    85                  90                  95
```

```
Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Xaa Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Xaa Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
```

```
                515                 520                 525
Asp Asn Tyr Ile Gln Val Ser Gln Leu Thr Lys Pro Ile Ser Ser Leu
    530                 535                 540

Thr Lys Pro Tyr His
545

<210> SEQ ID NO 39
<211> LENGTH: 521
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (210)..(210)
<223> OTHER INFORMATION: L-Asp of residue 210 is substituted with an
      alpha-amino acid different from L-Asp.
<220> FEATURE:
<221> NAME/KEY: MOD_RES
<222> LOCATION: (386)..(386)
<223> OTHER INFORMATION: L-Glu of residue 414 is substituted with an
      alpha-amino acid residue different from L-Glu

<400> SEQUENCE: 39

Arg Arg Leu Arg Ala Glu Pro Gly Asp Gly Ala Gln Thr Trp Ala Arg
1               5                   10                  15

Phe Ser Arg Pro Pro Ala Pro Glu Ala Ala Gly Leu Phe Gln Gly Thr
            20                  25                  30

Phe Pro Asp Gly Phe Leu Trp Ala Val Gly Ser Ala Ala Tyr Gln Thr
        35                  40                  45

Glu Gly Gly Trp Gln Gln His Gly Lys Gly Ala Ser Ile Trp Asp Thr
50                  55                  60

Phe Thr His His Pro Leu Ala Pro Pro Gly Asp Ser Arg Asn Ala Ser
65                  70                  75                  80

Leu Pro Leu Gly Ala Pro Ser Pro Leu Gln Pro Ala Thr Gly Asp Val
                85                  90                  95

Ala Ser Asp Ser Tyr Asn Asn Val Phe Arg Asp Thr Glu Ala Leu Arg
            100                 105                 110

Glu Leu Gly Val Thr His Tyr Arg Phe Ser Ile Ser Trp Ala Arg Val
        115                 120                 125

Leu Pro Asn Gly Ser Ala Gly Val Pro Asn Arg Glu Gly Leu Arg Tyr
    130                 135                 140

Tyr Arg Arg Leu Leu Glu Arg Leu Arg Glu Leu Gly Val Gln Pro Val
145                 150                 155                 160

Val Thr Leu Tyr His Trp Asp Leu Pro Gln Arg Leu Gln Asp Ala Tyr
                165                 170                 175

Gly Gly Trp Ala Asn Arg Ala Leu Ala Asp His Phe Arg Asp Tyr Ala
            180                 185                 190

Glu Leu Cys Phe Arg His Phe Gly Gly Gln Val Lys Tyr Trp Ile Thr
        195                 200                 205

Ile Xaa Asn Pro Tyr Val Val Ala Trp His Gly Tyr Ala Thr Gly Arg
    210                 215                 220

Leu Ala Pro Gly Ile Arg Gly Ser Pro Arg Leu Gly Tyr Leu Val Ala
225                 230                 235                 240

His Asn Leu Leu Leu Ala His Ala Lys Val Trp His Leu Tyr Asn Thr
                245                 250                 255

Ser Phe Arg Pro Thr Gln Gly Gly Gln Val Ser Ile Ala Leu Ser Ser
            260                 265                 270
```

```
His Trp Ile Asn Pro Arg Arg Met Thr Asp His Ser Ile Lys Glu Cys
            275                 280                 285

Gln Lys Ser Leu Asp Phe Val Leu Gly Trp Phe Ala Lys Pro Val Phe
        290                 295                 300

Ile Asp Gly Asp Tyr Pro Glu Ser Met Lys Asn Asn Leu Ser Ser Ile
305                 310                 315                 320

Leu Pro Asp Phe Thr Glu Ser Glu Lys Lys Phe Ile Lys Gly Thr Ala
                325                 330                 335

Asp Phe Phe Ala Leu Cys Phe Gly Pro Thr Leu Ser Phe Gln Leu Leu
            340                 345                 350

Asp Pro His Met Lys Phe Arg Gln Leu Glu Ser Pro Asn Leu Arg Gln
        355                 360                 365

Leu Leu Ser Trp Ile Asp Leu Glu Phe Asn His Pro Gln Ile Phe Ile
    370                 375                 380

Val Glx Asn Gly Trp Phe Val Ser Gly Thr Thr Lys Arg Asp Asp Ala
385                 390                 395                 400

Lys Tyr Met Tyr Tyr Leu Lys Lys Phe Ile Met Glu Thr Leu Lys Ala
                405                 410                 415

Ile Lys Leu Asp Gly Val Asp Val Ile Gly Tyr Thr Ala Trp Ser Leu
            420                 425                 430

Met Asp Gly Phe Glu Trp His Arg Gly Tyr Ser Ile Arg Arg Gly Leu
        435                 440                 445

Phe Tyr Val Asp Phe Leu Ser Gln Asp Lys Met Leu Leu Pro Lys Ser
    450                 455                 460

Ser Ala Leu Phe Tyr Gln Lys Leu Ile Glu Lys Asn Gly Phe Pro Pro
465                 470                 475                 480

Leu Pro Glu Asn Gln Pro Leu Glu Gly Thr Phe Pro Cys Asp Phe Ala
                485                 490                 495

Trp Gly Val Val Asp Asn Tyr Ile Gln Val Ser Gln Leu Thr Lys Pro
            500                 505                 510

Ile Ser Ser Leu Thr Lys Pro Tyr His
        515                 520

<210> SEQ ID NO 40
<211> LENGTH: 516
<212> TYPE: PRT
<213> ORGANISM: Artificial
<220> FEATURE:
<223> OTHER INFORMATION: variant polypeptide
<220> FEATURE:
<221> NAME/KEY: MOD_RES
<222> LOCATION: (205)..(205)
<223> OTHER INFORMATION: L-Asp of residue 205 is substituted with an
      alpha-amino acid different from L-Asp.
<220> FEATURE:
<221> NAME/KEY: MOD_RES
<222> LOCATION: (381)..(381)
<223> OTHER INFORMATION: L-Glu of residue 381 is substituted with an
      alpha-amino acid residue different from L-Glu

<400> SEQUENCE: 40

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60
```

-continued

```
Leu Ala Pro Pro Gly Asp Ser Arg Asn Ala Ser Leu Pro Leu Gly Ala
 65                  70                  75                  80

Pro Ser Pro Leu Gln Pro Ala Thr Gly Asp Val Ala Ser Asp Ser Tyr
                 85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Xaa Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glx Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480
```

```
Pro Leu Glu Gly Thr Phe Pro Cys Asp Phe Ala Trp Gly Val Val Asp
            485                 490                 495

Asn Tyr Ile Gln Val Ser Gln Leu Thr Lys Pro Ile Ser Ser Leu Thr
        500                 505                 510

Lys Pro Tyr His
        515

<210> SEQ ID NO 41
<211> LENGTH: 3036
<212> TYPE: DNA
<213> ORGANISM: Artificial
<220> FEATURE:
<223> OTHER INFORMATION: DNA encoding recombinant polypeptide
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 41
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtgtctcgcg gcctcctgcc cccgaggccc cgggcctctt ccagggcacc    180
ttccccgacg gcttcctctg ggccgtgggc agcgccgcct accagaccga gggcggctgg    240
cagcagcacg gcaagggtgc gtccatctgg gacacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acggcggctg gccaaccgcg ccctggccg accacttcag ggattacgcg    660
gagctctgct ccgccactt cggcggtcag gtcaagtact ggatcaccat cgacaacccc    720
tacgtggtgg cctggcacgg ctacgccacc gggcgcctgg ccccggcat ccggggcagc    780 ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaaatctctg    960 gactttgtac taggttggtt tgccaaaccc gtatttattg atggtgacta tcccgagagc   1020
atgaagaata ccctttcatc tattctgcct gattttactg aatctgagaa aagttcatc   1080 aaaggaactg ctgactttt tgctcttttgc tttggaccca ccttgagttt caacttttg   1140 gaccctcaca tgaagttccg ccaattggaa tctcccaacc tgaggcaact gctttcctgg   1200
attgaccttg aatttaacca tcctcaaata tttattgtgg aaaatggctg gtttgtctca   1260
gggaccacca agagagatga tgccaaatat atgtattacc tcaaaagtt catcatggaa   1320 accttaaaag ccatcaagct ggatgggtg gatgtcatcg gtataccgc atggtccctc   1380 atggatggtt tcgagtggca cagaggttac agcatcaggc gtggactctt ctatgttgac   1440
tttctaagcc aggacaagat gttgttgcca agtcttcag ccttgttcta ccaaaagctg   1500
atagagaaaa atggcttccc tcctttacct gaaaatcagc ccctagaagg gacatttccc   1560
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
```

```
gatggggttg tgaccaagaa gaggaaatcc tactgtgttg actttgctgc catccagccc    1740
cagatcgctt tactccagga aatgcacgtt acacattttc gcttctccct ggactgggcc    1800
ctgattctcc ctctgggtaa ccagtcccag gtgaaccaca ccatcctgca gtactatcgc    1860
tgcatggcca gcgagcttgt ccgtgtcaac atcaccccag tggtggccct gtggcagcct    1920
atggccccga accaaggact gccgcgcctc ctggccaggc agggcgcctg ggagaacccc    1980
tacactgccc tggcctttgc agagtatgcc cgactgtgct ttcaagagct cggccatcac    2040
gtcaagcttt ggataacgat gaatgagccg tatacaagga atatgacata cagtgctggc    2100
cacaaccttc tgaaggccca tgccctggct tggcatgtgt acaatgaaaa gtttaggcat    2160
gctcagaatg gaaaatatc catagccttg caggctgatt ggatagaacc tgcctgccct    2220
ttctcccaaa aggacaaaga ggtggccgag agagttttgg aatttgacat ggctggctg    2280 gctgagccca ttttcggctc tggagattat ccatgggtga tgagggactg gctgaaccaa    2340
agaaacaatt tcttcttcc ttatttcact gaagatgaaa aaaagctaat ccagggtacc    2400
tttgactttt tggctttaag ccattatacc accatccttg tagactcaga aaagaagat    2460 ccaataaaat acaatgatta cctagaagtg caagaaatga ccgacatcac gtggctcaac    2520 tccccccagtc aggtggcggt agtgccctgg gggttgcgca aagtgctgaa ctggctgaag    2580
ttcaagtacg agacctccc catgtacata atatccaacg gaatcgatga cgggctgcat    2640
gctgaggacg accagctgag ggtgtattat atgcagaatt acataaacga agctctcaaa    2700
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttca caccccgaaag    2940 tctttactgg ctttcatagc ttttctattt tttgcttcta ttatttctct ctcccttata    3000
ttttactact cgaagaaagg cagaagaagt tacaaa                              3036
```

<210> SEQ ID NO 42  
<211> LENGTH: 2949  
<212> TYPE: DNA  
<213> ORGANISM: Artificial  
<220> FEATURE:  
<223> OTHER INFORMATION: DNA encoding recombinant polypeptide

<400> SEQUENCE: 42

```
cgcctgcgtg cggagccggg cgacggcgcg cagacctggg cccgtgtctc gcggcctcct     60
gcccccgagg ccgcgggcct cttccagggc accttccccg acggcttcct ctgggccgtg    120
ggcagcgccg cctaccagac cgagggcggc tggcagcagc acggcaaggg tgcgtccatc    180
tgggacacgt tcacccacca ccccctggca cccccgggag actcccggaa cgccagtctg    240
ccgttgggcg ccccgtcgcc gctgcagccc gccaccgggg acgtagccag cgacagctac    300
aacaacgtct tccgcgacac ggaggcgctg cgcgagctcg gggtcactca ctaccgcttc    360
tccatctcgt gggcgcgagt gctccccaat ggcagcgcgg gcgtcccaa ccgcgagggg    420 ctgcgctact accggcgcct gctggagcgg ctgcgggagc tgggcgtgca gcccgtggtc    480
accctgtacc actgggacct gccccagcgc ctgcaggacg cctacggcgg ctgggccaac    540
cgcgccctgg ccgaccactt cagggattac gcggagctct gcttccgcca cttcggcggt    600
caggtcaagt actggatcac catcgacaac ccctacgtgg tggcctggca cggctacgcc    660
```

```
accgggcgcc tggccccegg catccggggc agcccgcggc tcgggtacct ggtggcgcac    720
aacctcctcc tggctcatgc caaagtctgg catctctaca atacttcttt ccgtcccact    780
cagggaggtc aggtgtccat tgccctaagc tctcactgga tcaatcctcg aagaatgacc    840
gaccacagca tcaaagaatg tcaaaaatct ctggactttg tactaggttg gtttgccaaa    900
cccgtattta ttgatggtga ctatcccgag agcatgaaga ataacctttc atctattctg    960
cctgatttta ctgaatctga gaaaagttc atcaaaggaa ctgctgactt ttttgctctt    1020
tgctttggac ccaccttgag ttttcaactt ttggaccctc acatgaagtt ccgccaattg    1080
gaatctccca acctgaggca actgctttcc tggattgacc ttgaatttaa ccatcctcaa    1140
atatttattg tggaaaatgg ctggtttgtc tcagggacca ccaagagaga tgatgccaaa    1200
tatatgtatt acctcaaaaa gttcatcatg gaaaccttaa aagccatcaa gctggatggg    1260
gtggatgtca tcgggtatac cgcatggtcc ctcatggatg gtttcgagtg gcacagaggt    1320
tacagcatca ggcgtggact cttctatgtt gactttctaa gccaggacaa gatgttgttg    1380
ccaaagtctt cagccttgtt ctaccaaaag ctgatagaga aaaatggctt ccctcctta    1440
cctgaaaatc agcccctaga agggacattt ccctgtgact tgcttgggg agttgttgac    1500
aactacattc aagtagatac cactctgtct cagtttaccg acctgaatgt ttacctgtgg    1560
gatgtccacc acagtaaaag gcttattaaa gtggatgggg ttgtgaccaa gaagaggaaa    1620
tcctactgtg ttgactttgc tgccatccag ccccagatcg ctttactcca ggaaatgcac    1680
gttacacatt tcgcttctc cctggactgg gccctgattc tccctctggg taaccagtcc    1740
caggtgaaca caccatcct gcagtactat cgctgcatgg ccagcgagct tgtccgtgtc    1800
aacatcaccc cagtggtggc cctgtggcag cctatggccc cgaaccaagg actgccgcgc    1860
ctcctggcca ggcagggcgc ctgggagaac ccctacactg ccctggcctt tgcagagtat    1920
gcccgactgt gctttcaaga gctcggccat cacgtcaagc tttggataac gatgaatgag    1980
ccgtatacaa ggaatatgac atacagtgct ggccacaacc ttctgaaggc ccatgccctg    2040
gcttggcatg tgtacaatga aaagtttagg catgctcaga tgggaaaaat atccatagcc    2100
ttgcaggctg attggataga acctgcctgc ccttctccc aaaaggacaa agaggtggcc    2160
gagagagttt tggaatttga cattggctgg ctggctgagc ccatttcgg ctctggagat    2220
tatccatggg tgatgaggga ctggctgaac caaagaaaca ttttcttct tccttatttc    2280
actgaagatg aaaaaaagct aatccagggt acctttgact ttttggcttt aagccattat    2340
accaccatcc ttgtagactc agaaaaagaa gatccaataa aatacaatga ttacctagaa    2400
gtgcaagaaa tgaccgacat cacgtggctc aactccccca gtcaggtggc ggtagtgccc    2460
tgggggttgc gcaaagtgct gaactggctg aagttcaagt acggagacct ccccatgtac    2520
ataatatcca acggaatcga tgacgggctg catgctgagg acgaccagct gagggtgtat    2580
tatatgcaga attacataaa cgaagctctc aaagcccaca tactgatgg tatcaatctt    2640
tgcggatact ttgcttattc gtttaacgac cgcacagctc cgaggtttgg cctctatcgt    2700
tatgctgcag atcagtttga gcccaaggca tccatgaaac attacaggaa aattattgac    2760
agcaatggtt tcccgggccc agaaactctg gaaagatttt gtccagaaga attcaccgtg    2820
tgtactgagt gcagttttt tcacacccga aagtctttac tggctttcat gcttttcta    2880
ttttttgctt ctattatttc tctctcccctt atattttact actcgaagaa aggcagaaga    2940
agttacaaa                                                            2949
```

-continued

```
<210> SEQ ID NO 43
<211> LENGTH: 2940
<212> TYPE: DNA
<213> ORGANISM: Artificial
<220> FEATURE:
<223> OTHER INFORMATION: DNA encoding recombinant polypeptide

<400> SEQUENCE: 43
atgcccgcca gcgccccgcc gcgccgcccg cggccgccgc cgccgtcgct gtcgctgctg      60
ctggtgctgc tgggcctggg cggccgccgc ctgcgtgcgg agccgggcga cggcgcgcag     120
acctgggccc gtgtctcgcg gcctcctgcc cccgaggccg cgggcctctt ccagggcacc     180
ttccccgacg gcttcctctg ggccgtgggc agcgccgcct accagaccga gggcggctgg     240
cagcagcacg gcaagggtgc gtccatctgg gacacgttca cccaccaccc cctggcaccc     300
ccgggagact cccggaacgc cagtctgccg ttgggcgccc gtcgccgct gcagcccgcc      360 accggggacg tagccagcga cagctacaac aacgtcttcc gcgacacgga ggcgctgcgc     420
gagctcgggg tcactcacta ccgcttctcc atctcgtggg cgcgagtgct ccccaatggc     480
agcgcgggcg tccccaaccg gaggggctg cgctactacc ggcgcctgct ggagcggctg      540
cgggagctgg gcgtgcagcc cgtggtcacc ctgtaccact gggacctgcc ccagcgcctg     600
caggacgcct acggcggctg gccaaccgc gccctggccg accacttcag ggattacgcg      660
gagctctgct ccgccactt cggcggtcag gtcaagtact ggatcaccat cgacaacccc      720
tacgtggtgg cctggcacgg ctacgccacc gggcgcctgg ccccggcat ccggggcagc      780 ccgcggctcg gtacctggt ggcgcacaac ctcctcctgg ctcatgccaa agtctggcat      840
ctctacaata cttctttccg tcccactcag ggaggtcagg tgtccattgc cctaagctct     900
cactggatca atcctcgaag aatgaccgac cacagcatca agaatgtca aaaatctctg      960 gactttgtac taggttggtt tgccaaaccc gtatttattg atggtgacta tcccgagagc    1020
atgaagaata accttcatc tattctgcct gattttactg aatctgagaa aaagttcatc     1080
aaaggaactg ctgactttt tgctctttgc tttggaccca ccttgagttt tcaactttg      1140 gaccctcaca tgaagttccg ccaattggaa tctcccaacc tgaggcaact gctttcctgg    1200
attgaccttg aatttaacca tcctcaaata tttattgtgg aaaatggctg gtttgtctca    1260
gggaccacca agagagatga tgccaaatat atgtattacc tcaaaaagtt catcatggaa    1320
accttaaaag ccatcaagct ggatgggtg atgtcatcg gtataccgc atggtccctc      1380 atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tcctttacct gaaaatcagc cctagaagg acatttccc      1560 tgtgactttg cttggggagt tgttgacaac tacattcaag tagataccac tctgtctcag    1620
tttaccgacc tgaatgttta cctgtgggat gtccaccaca gtaaaaggct tattaaagtg    1680
gatggggttg tgaccaagaa gaggaaatcc tactgtgttg actttgctgc catccagccc    1740
cagatcgctt tactccagga aatgcacgtt acacattttc gcttctccct ggactgggcc    1800
ctgattctcc ctctgggtaa ccagtcccag gtgaaccaca ccatcctgca gtactatcgc    1860
tgcatggcca gcgagcttgt ccgtgtcaac atcaccccag tggtggccct gtggcagcct    1920
atggccccga accaaggact gccgcgcctc ctggccaggc agggcgcctg ggagaacccc    1980
tacactgccc tggcctttgc agagtatgcc cgactgtgct tcaagagct cggccatcac    2040 gtcaagcttt ggataacgat gaatgagccg tatacaagga atatgacata cagtgctggc    2100
```

| | |
|---|---|
| cacaaccttc tgaaggccca tgccctggct tggcatgtgt acaatgaaaa gtttaggcat | 2160 |
| gctcagaatg ggaaaatatc catagccttg caggctgatt ggatagaacc tgcctgccct | 2220 |
| ttctcccaaa aggacaaaga ggtggccgag agagttttgg aatttgacat tggctggctg | 2280 |
| gctgagccca ttttcggctc tggagattat ccatgggtga tgagggactg gctgaaccaa | 2340 |
| agaaacaatt ttcttcttcc ttatttcact gaagatgaaa aaaagctaat ccagggtacc | 2400 |
| tttgactttt tggctttaag ccattatacc accatccttg tagactcaga aaaagaagat | 2460 |
| ccaataaaat acaatgatta cctagaagtg caagaaatga ccgacatcac gtggctcaac | 2520 |
| tcccccagtc aggtggcggt agtgccctgg gggttgcgca aagtgctgaa ctggctgaag | 2580 |
| ttcaagtacg gagacctccc catgtacata atatccaacg gaatcgatga cgggctgcat | 2640 |
| gctgaggacg accagctgag ggtgtattat atgcagaatt acataaacga agctctcaaa | 2700 |
| gcccacatac tggatggtat caatctttgc ggatactttg cttattcgtt taacgaccgc | 2760 |
| acagctccga ggtttggcct ctatcgttat gctgcagatc agtttgagcc caaggcatcc | 2820 |
| atgaaacatt acaggaaaat tattgacagc aatggttttcc cgggcccaga aactctggaa | 2880 |
| agattttgtc cagaagaatt caccgtgtgt actgagtgca gttttttttca cacccgaaag | 2940 |

<210> SEQ ID NO 44
<211> LENGTH: 2857
<212> TYPE: DNA
<213> ORGANISM: Artificial
<220> FEATURE:
<223> OTHER INFORMATION: DNA encoding recombinant polypeptide

<400> SEQUENCE: 44

| | |
|---|---|
| ccgccgcctg cgtgcggagc cgggcgacgg cgcgcagacc tgggcccgtg tctcgcggcc | 60 |
| tcctgccccc gaggccgcgg gcctcttcca gggcaccttc cccgacggct tcctctgggc | 120 |
| cgtgggcagc gccgcctacc agaccgaggg cggctggcag cagcacggca agggtgcgtc | 180 |
| catctgggac acgttcaccc accacccct ggcaccccg ggagactccc ggaacgccag | 240 |
| tctgccgttg ggcgccccgt cgccgctgca gcccgccacc ggggacgtag ccagcgacag | 300 |
| ctacaacaac gtcttccgcg acacggaggc gctgcgcgag ctcggggtca ctcactaccg | 360 |
| cttctccatc tcgtgggcgc gagtgctccc caatggcagc gcgggcgtcc ccaaccgcga | 420 |
| ggggctgcgc tactaccggc gcctgctgga gcggctgcgg gagctgggcg tgcagcccgt | 480 |
| ggtcaccctg taccactggg acctgccca gcgcctgcag gacgcctacg gcggctgggc | 540 |
| caaccgcgcc ctggccgacc acttcaggga ttacgcggag ctctgcttcc gccacttcgg | 600 |
| cggtcaggtc aagtactgga tcaccatcga caaccctac gtggtggcct ggcacggcta | 660 |
| cgccaccggg cgcctggccc ccggcatccg gggcagcccg cggctcgggt acctggtggc | 720 |
| gcacaacctc ctcctggctc atgccaaagt ctggcatctc tacaatactt ctttccgtcc | 780 |
| cactcaggga ggtcaggtgt ccattgccct aagctctcac tggatcaatc ctcgaagaat | 840 |
| gaccgaccac agcatcaaag aatgtcaaaa atctctggac tttgtactag gttggtttgc | 900 |
| caaacccgta tttattgatg gtgactatcc cgagagcatg aagaataacc tttcatctat | 960 |
| tctgcctgat tttactgaat ctgagaaaaa gttcatcaaa ggaactgctg acttttttgc | 1020 |
| tctttgcttt ggaccccacct tgagttttca acttttggac cctcacatga gttccgcca | 1080 |
| attggaatct cccaacctga ggcaactgct ttcctggatt gaccttgaat ttaaccatcc | 1140 |
| tcaaatattt attgtggaaa atggctggtt tgtctcaggg accaccaaga gagatgatgc | 1200 |
| caaatatatg tattaccctc aaaaagttca catggaaacc ttaaaagcca tcaagctgga | 1260 |

```
tggggtggat gtcatcgggt ataccgcatg gtccctcatg gatggtttcg agtggcacag    1320
aggttacagc atcaggcgtg gactcttcta tgttgacttt ctaagccagg acaagatgtt    1380
gttgccaaag tcttcagcct tgttctacca aaagctgata gagaaaaatg cttccctcc    1440 tttacctgaa atcagcccc tagaagggac atttccctgt gactttgctt ggggagttgt    1500
tgacaactac attcaagtag ataccactct gtctcagttt accgacctga atgtttacct    1560
gtgggatgtc caccacagta aaaggcttat taaagtggat gggggttgtga ccaagaagag    1620 gaaatcctac tgtgttgact ttgctgccat ccagccccag atcgtttac tccaggaaat    1680 gcacgttaca cattttcgct tctccctgga ctgggccctg attctccctc tgggtaacca    1740
gtcccaggtg aaccacacca tcctgcagta ctatcgctgc atggccagcg agcttgtccg    1800
tgtcaacatc accccagtgg tggccctgtg gcagcctatg gccccgaacc aaggactgcc    1860
gcgcctcctg gccaggcagg gcgcctggga gaaccctac actgccctgg cctttgcaga    1920
gtatgcccga ctgtgctttc aagagctcgg ccatcacgtc aagctttgga taacgatgaa    1980
tgagccgtat acaaggaata tgacatacag tgctggccac aaccttctga aggcccatgc    2040
cctggcttgg catgtgtaca atgaaaagtt taggcatgct cagaatggga aaatatccat    2100
agccttgcag gctgattgga tagaacctgc ctgcccttc tcccaaaagg acaaagaggt    2160
ggccgagaga gttttggaat tgacattgg ctggctggct gagcccattt tcggctctgg    2220
agattatcca tgggtgatga gggactggct gaaccaaaga acaattttc ttcttcctta    2280 tttcactgaa gatgaaaaaa agctaatcca gggtaccttt gacttttggg ctttaagcca    2340
ttataccacc atccttgtag actcagaaaa agaagatcca ataaaataca atgattacct    2400
agaagtgcaa gaaatgaccg acatcacgtg gctcaactcc cccagtcagg tggcggtagt    2460
gccctggggg ttgcgcaaag tgctgaactg gctgaagttc aagtacggag acctccccat    2520
gtacataata tccaacggaa tcgatgacg gctgcatgct gaggacgacc agctgagggt    2580
gtattatatg cagaattaca taaacgaagc tctcaaagcc cacatactgg atggtatcaa    2640
tctttgcgga tactttgctt attcgtttaa cgaccgcaca gctccgaggt ttggcctcta    2700
tcgttatgct gcagatcagt ttgagcccaa ggcatccatg aaacattaca ggaaaattat    2760
tgacagcaat ggtttccccgg gcccagaaac tctggaaaga ttttgtccag aagaattcac    2820
cgtgtgtact gagtgcagtt tttttcacac ccgaaag                             2857

<210> SEQ ID NO 45
<211> LENGTH: 1704
<212> TYPE: DNA
<213> ORGANISM: Artificial
<220> FEATURE:
<223> OTHER INFORMATION: DNA encoding recombinant polypeptide

<400> SEQUENCE: 45
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag    120
acctgggccc gtgtctcgcg gcctcctgcc cccgaggccg cgggcctctt ccagggcacc    180
ttccccgacg gcttcctctg gccgtgggc agcgccgcct accagaccga gggcggctgg    240
cagcagcacg gcaagggtgc gtccatctgg gacacgttca cccaccaccc cctggcaccc    300
ccgggagact cccggaacgc cagtctgccg ttgggcgccc gtcgccgct gcagcccgcc    360 accggggacg tagccagcga cagctacaac aacgtcttcc gcgacacgga ggcgctgcgc    420
```

```
gagctcgggg tcactcacta ccgcttctcc atctcgtggg cgcgagtgct ccccaatggc      480
agcgcgggcg tccccaaccg cgaggggctg cgctactacc ggcgcctgct ggagcggctg      540
cgggagctgg gcgtgcagcc cgtggtcacc ctgtaccact gggacctgcc ccagcgcctg      600
caggacgcct acggcggctg ggccaaccgc gccctggccg accacttcag ggattacgcg      660
gagctctgct tccgccactt cggcggtcag gtcaagtact ggatcaccat cgacaacccc      720
tacgtggtgg cctggcacgg ctacgccacc gggcgcctgg cccccggcat ccggggcagc      780
ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca agaatgtca aaaatctctg      960 gactttgtac taggttggtt tgccaaaccc gtatttattg atggtgacta tcccgagagc     1020
atgaagaata acctttcatc tattctgcct gattttactg aatctgagaa aaagttcatc     1080
aaaggaactg ctgacttttt tgctctttgc tttggaccca ccttgagttt tcaacttttg     1140
gaccctcaca tgaagttccg ccaattggaa tctcccaacc tgaggcaact gctttcctgg     1200
attgaccttg aatttaacca tcctcaaata tttattgtgg aaaatggctg gtttgtctca     1260
gggaccacca agagagatga tgccaaatat atgtattacc tcaaaaagtt catcatggaa     1320
accttaaaag ccatcaagct ggatggggtg gatgtcatcg ggtataccgc atggtccctc     1380
atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tcctttacct gaaaatcagc ccctagaagg gacatttccc     1560
tgtgactttg cttggggagt tgttgacaac tacattcaag tagataccac tctgtctcag     1620
tttaccgacc tgaatgttta cctgtgggat gtccaccaca gtaaaaggct tattaaagtg     1680
gatggggttg tgaccaagaa gagg                                             1704

<210> SEQ ID NO 46
<211> LENGTH: 1621
<212> TYPE: DNA
<213> ORGANISM: Artificial
<220> FEATURE:
<223> OTHER INFORMATION: DNA encoding recombinant polypeptide

<400> SEQUENCE: 46
ccgccgcctg cgtgcggagc cgggcgacgg cgcgcagacc tgggcccgtg tctcgcggcc       60
tcctgccccc gaggccgcgg gcctcttcca gggcaccttc cccgacggct tcctctgggc      120
cgtgggcagc gccgcctacc agaccgaggg cggctggcag cagcacggca agggtgcgtc      180
catctgggac acgttcaccc accacccccct ggcaccccccg ggagactccc ggaacgccag      240
tctgccgttg ggcgccccgt cgccgctgca gcccgccacc ggggacgtag ccagcgacag      300
ctacaacaac gtcttccgcg cacggaggc gctgcgcgag ctcggggtca ctcactaccg      360
cttctccatc tcgtgggcgc gagtgctccc caatggcagc gcgggcgtcc ccaaccgcga      420
ggggctgcgc tactaccggc gcctgctgga gcggctgcgg agctgggcg tgcagcccgt      480 ggtcaccctg taccactggg acctgcccca gcgcctgcag gacgcctacg gcggctgggc      540
caaccgcgcc ctggccgacc acttcaggga ttacgcggag ctctgcttcc gccacttcgg      600
cggtcaggtc aagtactgga tcaccatcga caacccctac gtggtggcct ggcacggcta      660
cgccaccggg cgcctggccc ccggcatccg gggcagcccg cggctcgggt acctggtggc      720
gcacaacctc ctcctggctc atgccaaagt ctggcatctc tacaatactt ctttccgtcc      780
```

-continued

```
cactcaggga ggtcaggtgt ccattgccct aagctctcac tggatcaatc ctcgaagaat    840
gaccgaccac agcatcaaag aatgtcaaaa atctctggac tttgtactag gttggtttgc    900
caaacccgta tttattgatg gtgactatcc cgagagcatg aagaataacc tttcatctat    960
tctgcctgat tttactgaat ctgagaaaaa gttcatcaaa ggaactgctg acttttttgc   1020
tctttgcttt ggacccacct tgagttttca acttttggac cctcacatga agttccgcca   1080
attggaatct cccaacctga ggcaactgct ttcctggatt gaccttgaat ttaaccatcc   1140
tcaaatattt attgtggaaa atggctggtt tgtctcaggg accaccaaga gagatgatgc   1200
caaatatatg tattacctca aaagttcat catggaaacc ttaaaagcca tcaagctgga   1260
tggggtggat gtcatcgggt ataccgcatg gtccctcatg gatggtttcg agtggcacag   1320
aggttacagc atcaggcgtg gactcttcta tgttgacttt ctaagccagg acaagatgtt   1380
gttgccaaag tcttcagcct tgttctacca aaagctgata gagaaaaatg cttccctcc   1440
tttacctgaa aatcagcccc tagaagggac atttccctgt gactttgctt ggggagttgt   1500
tgacaactac attcaagtag ataccactct gtctcagttt accgacctga atgtttacct   1560
gtgggatgtc caccacagta aaaggcttat taaagtggat ggggttgtga ccaagaagag   1620
g                                                                   1621
```

<210> SEQ ID NO 47
<211> LENGTH: 1548
<212> TYPE: DNA
<213> ORGANISM: Artificial
<220> FEATURE:
<223> OTHER INFORMATION: DNA encoding recombinant polypeptide

<400> SEQUENCE: 47

```
gagccgggcg acggcgcgca gacctgggcc cgtgtctcgc ggcctcctgc ccccgaggcc     60
gcgggcctct tccagggcac cttccccgac ggcttcctct gggccgtggg cagcgccgcc    120
taccagaccg agggcggctg gcagcagcac ggcaagggtg cgtccatctg ggacacgttc    180
acccaccacc ccctggcacc cccgggagac tcccggaacg ccagtctgcc gttgggcgcc    240
ccgtcgccgc tgcagcccgc caccggggac gtagccagca cagctacaa caacgtcttc    300
cgcgacacgg aggcgctgcg cgagctcggg gtcactcact accgcttctc catctcgtgg    360
gcgcgagtgc tccccaatgg cagcgcgggc gtccccaacc gcgaggggct gcgctactac    420
cggcgcctgc tggagcggct gcgggagctg ggcgtgcagc cgtggtcac cctgtaccac    480
tgggacctgc cccagcgcct gcaggacgcc tacggcggct gggccaaccg cgccctggcc    540
gaccacttca gggattacgc ggagctctgc ttccgccact cggcggtca ggtcaagtac    600
tggatcacca tcgacaaccc ctacgtggtg gcctggcacg gctacgccac cgggcgcctg    660
gcccccggca tccggggcag cccgcggctc gggtacctgg tggcgcacaa cctcctcctg    720
gctcatgcca agtctggca tctctacaat acttctttcc gtcccactca gggaggtcag    780
gtgtccattg ccctaagctc tcactggatc aatcctcgaa gaatgaccga ccacagcatc    840
aaagaatgtc aaaatctct ggactttgta ctaggttggt ttgccaaacc cgtatttatt    900
gatggtgact atcccgagag catgaagaat aacctttcat ctattctgcc tgattttact    960
gaatctgaga aaaagttcat caaggaact gctgactttt ttgctctttg ctttggaccc   1020
accttgagtt ttcaactttt ggaccctcac atgaagttcc gccaattgga atctcccaac   1080
ctgaggcaac tgctttcctg gattgacctt gaatttaacc atcctcaaat atttattgtg   1140
```

| | | | |
|---|---|---|---|
| gaaaatggct | ggtttgtctc | agggaccacc | aagagagatg atgccaaata tatgtattac | 1200 |
| ctcaaaaagt | tcatcatgga | aaccttaaaa | gccatcaagc tggatggggt ggatgtcatc | 1260 |
| gggtataccg | catggtccct | catggatggt | ttcgagtggc acagaggtta cagcatcagg | 1320 |
| cgtggactct | tctatgttga | ctttctaagc | aggacaaga tgttgttgcc aaagtcttca | 1380 |
| gccttgttct | accaaaagct | gatagagaaa | aatggcttcc ctcctttacc tgaaaatcag | 1440 |
| cccctagaag | ggacatttcc | ctgtgacttt | gcttggggag ttgttgacaa ctacattcaa | 1500 |
| gtagatacca | ctctgtctca | gtttaccgac | ctgaatgttt acctgtgg | 1548 |

<210> SEQ ID NO 48
<211> LENGTH: 1647
<212> TYPE: DNA
<213> ORGANISM: Artificial
<220> FEATURE:
<223> OTHER INFORMATION: DNA encoding recombinant polypeptide
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 48

| | | | |
|---|---|---|---|
| atgcccgcca | gcgcccgcc | gcgccgcccg | cggccgccgc cgccgtcgct gtcgctgctg | 60 |
| ctggtgctgc | tgggcctggg | cggccgccgc | ctgcgtgcgg agccgggcga cggcgcgcag | 120 |
| acctgggccc | gtgtctcgcg | gcctcctgcc | cccgaggccg cgggcctctt ccagggcacc | 180 |
| ttccccgacg | gcttcctctg | ggccgtgggc | agcgccgcct accagaccga gggcggctgg | 240 |
| cagcagcacg | gcaagggtgc | gtccatctgg | gacacgttca cccaccaccc cctggcaccc | 300 |
| ccgggagact | cccggaacgc | cagtctgccg | ttgggcgccc cgtcgccgct gcagcccgcc | 360 |
| accggggacg | tagccagcga | cagctacaac | aacgtcttcc gcgacacgga ggcgctgcgc | 420 |
| gagctcgggg | tcactcacta | ccgcttctcc | atctcgtggg cgcgagtgct ccccaatggc | 480 |
| agcgcgggcg | tccccaaccg | cgaggggctg | cgctactacc ggcgcctgct ggagcggctg | 540 |
| cgggagctgg | gcgtgcagcc | cgtggtcacc | ctgtaccact gggaccttgcc ccagcgcctg | 600 |
| caggacgcct | acggcggctg | ggccaaccgc | gccctggccg accacttcag ggattacgcg | 660 |
| gagctctgct | tccgccactt | cggcggtcag | gtcaagtact ggatcaccat cgacaacccc | 720 |
| tacgtggtgg | cctggcacgg | ctacgccacc | gggcgcctgg cccccggcat ccggggcagc | 780 |
| ccgcggctcg | ggtacctggt | ggcgcacaac | ctcctcctgg ctcatgccaa agtctggcat | 840 |
| ctctacaata | cttctttccg | tcccactcag | ggaggtcagg tgtccattgc cctaagctct | 900 |
| cactggatca | atcctcgaag | aatgaccgac | cacagcatca agaatgtca aaaatctctg | 960 |
| gactttgtac | taggttggtt | tgccaaaccc | gtatttattg atggtgacta tcccgagagc | 1020 |
| atgaagaata | acctttcatc | tattctgcct | gattttactg aatctgagaa aagttcatc | 1080 |
| aaaggaactg | ctgactttt | tgctctttgc | tttggaccca ccttgagttt caacttttg | 1140 |
| gaccctcaca | tgaagttccg | ccaattggaa | tctcccaacc tgaggcaact gctttcctgg | 1200 |
| attgaccttg | aatttaacca | tcctcaaata | tttattgtgg aaaatggctg gtttgtctca | 1260 |
| gggaccacca | agagagatga | tgccaaatat | atgtattacc tcaaaaagtt catcatggaa | 1320 |
| accttaaaag | ccatcaagct | ggatggggtg | gatgtcatcg gtataccgc atggtccctc | 1380 |
| atggatggtt | tcgagtggca | cagaggttac | agcatcaggc gtggactctt ctatgttgac | 1440 |
| tttctaagcc | aggacaagat | gttgttgcca | aagtcttcag ccttgttcta ccaaaagctg | 1500 |

| | |
|---|---|
| atagagaaaa atggcttccc tcctttacct gaaaatcagc ccctagaagg gacatttccc | 1560 |
| tgtgactttg cttggggagt tgttgacaac tacattcaag taagtcagct gacaaaacca | 1620 |
| atcagcagtc tcaccaagcc ctatcac | 1647 |

<210> SEQ ID NO 49
<211> LENGTH: 1563
<212> TYPE: DNA
<213> ORGANISM: Artificial
<220> FEATURE:
<223> OTHER INFORMATION: DNA encoding recombinant polypeptide

<400> SEQUENCE: 49

| | |
|---|---|
| cgccgcctgc gtgcggagcc gggcgacggc gcgcagacct gggcccgtgt ctcgcggcct | 60 |
| cctgccccg aggccgcggg cctcttccag ggcaccttcc ccgacggctt cctctgggcc | 120 |
| gtgggcagcg ccgcctacca gaccgagggc ggctggcagc agcacggcaa gggtgcgtcc | 180 |
| atctgggaca cgttcaccca ccacccctg gcaccccgg gagactcccg gaacgccagt | 240 |
| ctgccgttgg gcgccccgtc gccgctgcag cccgccaccg ggacgtagc cagcgacagc | 300 |
| tacaacaacg tcttccgcga cacggaggcg ctgcgcgagc tcggggtcac tcactaccgc | 360 |
| ttctccatct cgtgggcgcg agtgctcccc aatggcagcg cgggcgtccc caaccgcgag | 420 |
| gggctgcgct actaccggcg cctgctggag cggctgcggg agctgggcgt gcagcccgtg | 480 |
| gtcaccctgt accactggga cctgcccag cgcctgcagg acgcctacgg cggctgggcc | 540 |
| aaccgcgccc tggccgacca cttcagggat tacgcggagc tctgcttccg ccacttcggc | 600 |
| ggtcaggtca agtactggat caccatcgac aaccccacg tggtggcctg gcacggctac | 660 |
| gccaccgggc gcctggcccc cggcatccgg ggcagcccgc ggctcgggta cctggtggcg | 720 |
| cacaacctcc tcctggctca tgccaaagtc tggcatctct acaatacttc tttccgtccc | 780 |
| actcagggag gtcaggtgtc cattgcccta agctctcact ggatcaatcc tcgaagaatg | 840 |
| accgaccaca gcatcaaaga atgtcaaaaa tctctggact ttgtactagg ttggtttgcc | 900 |
| aaaccgtat ttattgatgg tgactatccc gagagcatga agaataacct ttcatctatt | 960 |
| ctgcctgatt ttactgaatc tgagaaaaag ttcatcaaag gaactgctga ctttttttgct | 1020 |
| cttttgctttg gacccaccct gagttttcaa cttttggacc ctcacatgaa gttccgccaa | 1080 |
| ttggaatctc ccaacctgag gcaactgctt cctggattg accttgaatt taaccatcct | 1140 |
| caaatattta ttgtggaaaa tggctggttt gtctcaggga ccaccaagag agatgatgcc | 1200 |
| aaatatatgt attacctcaa aaagttcatc atggaaacct aaaagccat caagctggat | 1260 |
| ggggtggatg tcatcgggta taccgcatgg tccctcatgg atggtttcga gtggcacaga | 1320 |
| ggttacagca tcaggcgtgg actcttctat gttgactttc taagccagga caagatgttg | 1380 |
| ttgccaaagt cttcagcctt gttctaccaa aagctgatag agaaaaatgg cttccctcct | 1440 |
| ttacctgaaa atcagcccct agaagggaca tttccctgtg actttgcttg gggagttgtt | 1500 |
| gacaactaca ttcaagtaag tcagctgaca aaaccaatca gcagtctcac caagccctat | 1560 |
| cac | 1563 |

<210> SEQ ID NO 50
<211> LENGTH: 1548
<212> TYPE: DNA
<213> ORGANISM: Artificial
<220> FEATURE:
<223> OTHER INFORMATION: DNA encoding recombinant polypeptide

<400> SEQUENCE: 50

```
gagccgggcg acggcgcgca gacctgggcc cgtgtctcgc ggcctcctgc ccccgaggcc    60
gcgggcctct tccagggcac cttccccgac ggcttcctct gggccgtggg cagcgccgcc   120
taccagaccg agggcggctg gcagcagcac ggcaagggtg cgtccatctg ggacacgttc   180
acccaccacc ccctggcacc cccggggaga ctcccggaacg ccagtctgcc gttgggcgcc   240
ccgtcgccgc tgcagcccgc caccggggac gtagccagcg acagctacaa caacgtcttc   300
cgcgacacgg aggcgctgcg cgagctcggg gtcactcact accgcttctc catctcgtgg   360
gcgcgagtgc tccccaatgg cagcgcgggc gtccccaacc gcgagggggct gcgctactac   420 cggcgcctgc tggagcggct gcgggagctg gcgtgcagc ccgtggtcac cctgtaccac   480
tgggacctgc cccagcgcct gcaggacgcc tacgcggct gggccaaccg cgccctggcc   540
gaccacttca gggattacgc ggagctctgc ttccgccact cggcggtca ggtcaagtac   600 tggatcacca tcgacaaccc ctacgtggtg gcctggcacg gctacgccac cgggcgcctg   660
gcccccggca tccggggcag cccgcggctc gggtacctgg tggcgcacaa cctcctcctg   720
gctcatgcca agtctggca tctctacaat acttctttcc gtcccactca gggaggtcag   780
gtgtccattg ccctaagctc tcactggatc aatcctcgaa gaatgaccga ccacagcatc   840
aaagaatgtc aaaaatctct ggactttgta ctaggttggt ttgccaaacc cgtatttatt   900
gatggtgact atcccgagag catgaagaat aacctttcat ctattctgcc tgatttact   960 gaatctgaga aaagttcat caaggaact gctgactttt ttgctctttg ctttggaccc  1020
accttgagtt ttcaactttt ggaccctcac atgaagttcc gccaattgga atctcccaac  1080
ctgaggcaac tgctttcctg gattgacctt gaatttaacc atcctcaaat atttattgtg  1140
gaaaatggct ggtttgtctc agggaccacc aagagagatg atgccaaata tatgtattac  1200
ctcaaaaagt tcatcatgga aaccttaaaa gccatcaagc tggatggggt ggatgtcatc  1260
gggtataccg catggtccct catggatggt ttcgagtggc acagaggtta cagcatcagg  1320
cgtggactct tctatgttga cttttctaagc caggacaaga tgttgttgcc aaagtcttca  1380
gccttgttct accaaaagct gatagagaaa aatggcttcc ctcctttacc tgaaaatcag  1440
cccctagaag ggacatttcc ctgtgacttt gcttggggag ttgttgacaa ctacattcaa  1500
gtaagtcagc tgacaaaacc aatcagcagt ctcaccaagc cctatcac               1548
```

<210> SEQ ID NO 51
<211> LENGTH: 3036
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1240)..(1242)
<223> OTHER INFORMATION: n is a, c, g, or t

<400> SEQUENCE: 51

```
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag   120
acctgggccc gtgtctcgcg gcctcctgcc cccgaggccc gggcctctt ccagggcac    180 ttccccgacg gcttcctctg ggccgtgggc agcgccgcct accagaccga gggcggctgg   240
cagcagcacg gcaagggtgc gtccatctgg gacacgttca cccaccaccc cctggcaccc   300 ccggggagact cccggaacgc cagtctgccg ttgggcgccc gtcgccgct gcagcccgcc   360
```

-continued

```
accgggqacg tagccagcga cagctacaac aacgtcttcc gcgacacgga ggcgctgcgc      420
gagctcgggg tcactcacta ccgcttctcc atctcgtggg cgcgagtgct ccccaatggc      480
agcgcgggcg tccccaaccg cgaggggctg cgctactacc ggcgcctgct ggagcggctg      540
cgggagctgg gcgtgcagcc cgtggtcacc ctgtaccact gggacctgcc ccagcgcctg      600
caggacgcct acggcggctg ggccaaccgc gccctggccg accacttcag ggattacgcg      660
gagctctgct tccgccactt cggcggtcag gtcaagtact ggatcaccat cgacaacccc      720
tacgtggtgg cctggcacgg ctacgccacc gggcgcctgg ccccggcat ccggggcagc       780 ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca aagaatgtca aaaatctctg      960
gactttgtac taggttggtt tgccaaaccc gtatttattg atggtgacta tcccgagagc     1020
atgaagaata acctttcatc tattctgcct gattttactg aatctgagaa aaagttcatc     1080
aaaggaactg ctgactttt tgctcttttgc tttggaccca ccttgagttt tcaacttttg     1140
gaccctcaca tgaagttccg ccaattggaa tctcccaacc tgaggcaact gctttcctgg     1200
attgaccttg aatttaacca tcctcaaata tttattgtgn nnaatggctg gtttgtctca     1260
gggaccacca agagagatga tgccaaatat atgtattacc tcaaaaagtt catcatggaa     1320
accttaaaag ccatcaagct ggatggggtg gatgtcatcg ggtataccgc atggtccctc     1380
atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tcctttacct gaaaatcagc ccctagaagg gacatttccc     1560
tgtgactttg cttggggagt tgttgacaac tacattcaag tagataccac tctgtctcag     1620
tttaccgacc tgaatgttta cctgtgggat gtccaccaca gtaaaaggct tattaaagtg     1680 gatgggggttg tgaccaagaa gaggaaatcc tactgtgttg actttgctgc catccagccc     1740
cagatcgctt tactccagga aatgcacgtt acacattttc gcttctccct ggactgggcc     1800
ctgattctcc ctctgggtaa ccagtcccag gtgaaccaca ccatcctgca gtactatcgc     1860
tgcatggcca gcgagcttgt ccgtgtcaac atcacccag tggtggccct gtggcagcct      1920
atggccccga accaaggact gccgcgcctc ctggccaggc agggcgcctg ggagaacccc     1980
tacactgccc tggcctttgc agagtatgcc cgactgtgct ttcaagagct cggccatcac     2040
gtcaagcttt ggataacgat gaatgagccg tatacaagga atatgacata cagtgctggc     2100
cacaaccttc tgaaggccca tgccctggct tggcatgtgt acaatgaaaa gtttaggcat     2160
gctcagaatg ggaaaatatc catagccttg caggctgatt ggatagaacc tgcctgccct     2220
ttctcccaaa aggacaaaga ggtggccgag agagtttggg aatttgacat tggctggctg     2280
gctgagccca ttttcggctc tggagattat ccatgggtga tgagggactg gctgaaccaa     2340
agaaacaatt ttcttcttcc ttatttcact gaagatgaaa aaaagctaat ccagggtacc     2400
tttgactttt tggctttaag ccattatacc accatccttg tagactcaga aaaagaagat     2460
ccaataaaat acaatgatta cctagaagtg caagaaatga ccgacatcac gtggctcaac     2520
tcccccagtc aggtggcggt agtgccctgg gggttgcgca aagtgctgaa ctggctgaag     2580
ttcaagtacg gagacctccc catgtacata atatccaacg gaatcgatga cgggctgcat     2640
gctgaggacg accagctgag ggtgtattat atgcagaatt acataaacga agctctcaaa     2700
gcccacatac tggatggtat caatctttgc ggatactttg cttattcgtt taacgaccgc    2760
```

-continued

```
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttca cacccgaaag     2940 tctttactgg ctttcatagc ttttctattt tttgcttcta ttatttctct ctcccttata   3000
ttttactact cgaagaaagg cagaagaagt tacaaa                              3036
```

<210> SEQ ID NO 52
<211> LENGTH: 2949
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1153)..(1155)
<223> OTHER INFORMATION: n is a, c, g, or t

<400> SEQUENCE: 52

```
cgcctgcgtg cggagccggg cgacggcgcg cagacctggg cccgtgtctc gcggcctcct      60
gcccccgagg ccgcgggcct cttccagggc accttcccg acggcttcct ctgggccgtg     120
ggcagcgccg cctaccagac cgagggcggc tggcagcagc acggcaaggg tgcgtccatc     180
tgggacacgt tcacccacca cccctggca ccccgggag actcccggaa cgccagtctg      240
ccgttgggcg ccccgtcgcc gctgcagccc gccaccgggg acgtagccag cgacagctac    300
aacaacgtct tccgcgacac ggaggcgctg cgcgagctcg gggtcactca ctaccgcttc    360
tccatctcgt gggcgcgagt gctccccaat ggcagcgcgg gcgtccccaa ccgcgagggg    420
ctgcgctact accggcgcct gctggagcgg ctgcgggagc tgggcgtgca gcccgtggtc    480
accctgtacc actgggacct gccccagcgc ctgcaggacg cctacggcgg ctgggccaac    540
cgcgccctgg ccgaccactt cagggattac gcggagctct gcttccgcca cttcggcggt    600
caggtcaagt actggatcac catcgacaac ccctacgtgg tggcctggca cggctacgcc    660
accgggcgcc tggccccgg catccggggc agcccgcggc tcgggtacct ggtggcgcac    720
aacctcctcc tggctcatgc caaagtctgg catctctaca atacttcttt ccgtcccact    780
cagggaggtc aggtgtccat tgccctaagc tctcactgga tcaatcctcg aagaatgacc    840
gaccacagca tcaagaatg tcaaaaatct ctggactttg tactaggttg gtttgccaaa    900
cccgtattta ttgatggtga ctatcccgag agcatgaaga ataacctttc atctattctg    960
cctgatttta ctgaatctga gaaaagttc atcaaaggaa ctgctgactt ttttgctctt   1020
tgctttggac ccaccttgag ttttcaactt ttggaccctc acatgaagtt ccgccaattg   1080
gaatctccca acctgaggca actgctttcc tggattgacc ttgaatttaa ccatcctcaa   1140
atatttattg tgnnnaatgg ctggtttgtc tcagggacca ccaagagaga tgatgccaaa   1200
tatatgtatt acctcaaaaa gttcatcatg gaaaccttaa aagccatcaa gctgatgggg   1260
gtggatgtca tcgggtatac cgcatggtcc ctcatggatg gtttcgagtg gcacagaggt   1320
tacagcatca ggcgtggact cttctatgtt gactttctaa gccaggacaa gatgttgttg   1380
ccaaagtctt cagccttgtt ctaccaaaag ctgatagaga aaaatggctt ccctcctta   1440 cctgaaaatc agcccctaga agggacattt ccctgtgact tgcttgggg agttgttgac   1500 aactacattc aagtagatac cactctgtct cagtttaccg acctgaatgt ttacctgtgg   1560
gatgtccacc acagtaaaag gcttattaaa gtggatgggg ttgtgaccaa gaagaggaaa   1620
```

| | |
|---|---|
| tcctactgtg ttgactttgc tgccatccag ccccagatcg ctttactcca ggaaatgcac | 1680 |
| gttacacatt ttcgcttctc cctggactgg gccctgattc tccctctggg taaccagtcc | 1740 |
| caggtgaacc acaccatcct gcagtactat cgctgcatgg ccagcgagct tgtccgtgtc | 1800 |
| aacatcaccc cagtggtggc cctgtggcag cctatggccc cgaaccaagg actgccgcgc | 1860 |
| ctcctggcca ggcagggcgc ctgggagaac ccctacactg ccctggcctt tgcagagtat | 1920 |
| gcccgactgt gctttcaaga gctcggccat cacgtcaagc tttggataac gatgaatgag | 1980 |
| ccgtatacaa ggaatatgac atacagtgct ggccacaacc ttctgaaggc ccatgccctg | 2040 |
| gcttggcatg tgtacaatga aaagtttagg catgctcaga tgggaaaat atccatagcc | 2100 |
| ttgcaggctg attggataga acctgcctgc cctttctccc aaaaggacaa agaggtggcc | 2160 |
| gagagagttt tggaatttga cattggctgg ctggctgagc ccattttcgg ctctggagat | 2220 |
| tatccatggg tgatgaggga ctggctgaac caaagaaaca attttcttct tccttatttc | 2280 |
| actgaagatg aaaaaaagct aatccagggt acctttgact ttttggcttt aagccattat | 2340 |
| accaccatcc ttgtagactc agaaaaagaa gatccaataa aatacaatga ttacctagaa | 2400 |
| gtgcaagaaa tgaccgacat cacgtggctc aactccccca gtcaggtggc ggtagtgccc | 2460 |
| tgggggttgc gcaaagtgct gaactggctg aagttcaagt acgagacct ccccatgtac | 2520 |
| ataatatcca acggaatcga tgacgggctg catgctgagg acgaccagct gagggtgtat | 2580 |
| tatatgcaga attacataaa cgaagctctc aaagcccaca tactgatgg tatcaatctt | 2640 |
| tgcggatact ttgcttattc gtttaacgac cgcacagctc cgaggtttgg cctctatcgt | 2700 |
| tatgctgcag atcagtttga gcccaaggca tccatgaaac attacaggaa aattattgac | 2760 |
| agcaatggtt tcccgggccc agaaactctg gaaagatttt gtccagaaga attcaccgtg | 2820 |
| tgtactgagt gcagttttt tcacacccga aagtctttac tggctttcat agcttttcta | 2880 |
| ttttttgctt ctattatttc tctctccctt atattttact actcgaagaa aggcagaaga | 2940 |
| agttacaaa | 2949 |

<210> SEQ ID NO 53
<211> LENGTH: 2940
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1240)..(1242)
<223> OTHER INFORMATION: n is a, c, g, or t

<400> SEQUENCE: 53

| | |
|---|---|
| atgcccgcca cgcccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc cgtgtctcgcg gcctcctgcc cccgaggccg cgggcctctt ccagggcacc | 180 |
| ttccccgacg gcttcctctg gccgtgggc agcgccgcct accagaccga gggcggctgg | 240 |
| cagcagcacg gcaagggtgc gtccatctgg gacacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggcg tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |

```
caggacgcct acggcggctg ggccaaccgc gccctggccg accacttcag ggattacgcg      660
gagctctgct tccgccactt cggcggtcag gtcaagtact ggatcaccat cgacaacccc      720
tacgtggtgg cctggcacgg ctacgccacc gggcgcctgg cccccggcat ccggggcagc      780
ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca agaatgtca aaaatctctg      960
gactttgtac taggttggtt tgccaaaccc gtatttattg atggtgacta tcccgagagc     1020
atgaagaata acctttcatc tattctgcct gattttactg aatctgagaa aaagttcatc     1080
aaaggaactg ctgactttt tgctctttgc tttggaccca ccttgagttt tcaacttttg      1140
gaccctcaca tgaagttccg ccaattggaa tctcccaacc tgaggcaact gcttcctgg      1200
attgaccttg aatttaacca tcctcaaata tttattgtgn nnaatggctg gtttgtctca     1260
gggaccacca agagagatga tgccaaatat atgtattacc tcaaaaagtt catcatggaa     1320
acccttaaaag ccatcaagct ggatggggtg gatgtcatcg ggtataccgc atggtccctc     1380
atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tcctttacct gaaaatcagc ccctagaagg gacatttccc     1560
tgtgactttg cttggggagt tgttgacaac tacattcaag tagataccac tctgtctcag     1620
tttaccgacc tgaatgtta cctgtgggat gtccaccaca gtaaaaggct tattaaagtg     1680
gatggggttg tgaccaagaa gaggaaatcc tactgtgttg actttgctgc catccagccc     1740
cagatcgctt tactccagga aatgcacgtt acacattttc gcttctccct ggactgggcc     1800
ctgattctcc ctctgggtaa ccagtcccag gtgaaccaca ccatcctgca gtactatcgc     1860
tgcatggcca gcgagcttgt ccgtgtcaac atcaccccag tggtggccct gtggcagcct     1920
atggccccga accaaggact gccgcgcctc ctggccaggc agggcgcctg ggagaacccc     1980
tacactgccc tggcctttgc agagtatgcc cgactgtgct ttcaagagct cggccatcac     2040
gtcaagcttt ggataacgat gaatgagccg tatacaagga atatgacata cagtgctggc     2100
cacaaccttc tgaaggccca tgccctggct tggcatgtgt acaatgaaaa gtttaggcat     2160
gctcagaatg ggaaaatatc catagccttg caggctgatt ggatagaacc tgcctgccct     2220
ttctcccaaa aggacaaaga ggtggccgag agagttttgg aatttgacat tggctggctg     2280
gctgagccca ttttcggctc tggagattat ccatgggtga tgagggactg gctgaaccaa     2340
agaaacaatt ttcttcttcc ttatttcact gaagatgaaa aaaagctaat ccagggtacc     2400
tttgactttt tggctttaag ccattatacc accatccttg tagactcaga aaagaagat     2460
ccaataaaat acaatgatta cctagaagtg caagaaatga ccgacatcac gtggctcaac     2520
tcccccagtc aggtggcggt agtgcccctgg gggttgcgca aagtgctgaa ctggctgaag     2580
ttcaagtacg gagacctccc catgtacata atatccaacg gaatcgatga cgggctgcat     2640
gctgaggacg accagctgag ggtgtattat atgcagaatt acataaacga agctctcaaa     2700
gcccacatac tggatggtat caatcttgc ggatacttg cttattcgtt taacgaccgc      2760
acagctccga ggtttggcct ctatcgttat gctgcagatc agtttgagcc caaggcatcc     2820
atgaaacatt acaggaaaat tattgacagc aatggtttcc cgggcccaga aactctggaa     2880
agattttgtc cagaagaatt caccgtgtgt actgagtgca gttttttca cacccgaaag     2940
```

<210> SEQ ID NO 54
<211> LENGTH: 2857
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1157)..(1159)
<223> OTHER INFORMATION: n is a, c, g, or t

<400> SEQUENCE: 54

```
ccgccgcctg cgtgcggagc cgggcgacgg cgcgcagacc tgggcccgtg tctcgcggcc    60
tcctgccccc gaggccgcgg gcctcttcca gggcaccttc cccgacggct tcctctgggc   120
cgtgggcagc gccgcctacc agaccgaggg cggctggcag cagcacgggca agggtgcgtc   180
catctgggac acgttcaccc accaccccct ggcaccccg ggagactccc ggaacgccag   240
tctgccgttg ggcgcccgt cgccgctgca gcccgccacc ggggacgtag ccagcgacag   300
ctacaacaac gtcttccgcg acacggaggc gctgcgcgag ctcggggtca ctcactaccg   360
cttctccatc tcgtgggcgc gagtgctccc caatggcagc gcgggcgtcc ccaaccgcga   420
ggggctgcgc tactaccggc gcctgctgga gcggctgcgg gagctgggcg tgcagcccgt   480
ggtcaccctg taccactggg acctgccccg agcctgcag gacgcctacg gcgctgggc   540
caaccgcgcc ctggccgacc acttcaggga ttacgggga ctctgcttcc gccacttcgg   600
cggtcaggtc aagtactgga tcaccatcga caaccctac gtggtggcct ggcacggcta   660
cgccaccggg cgcctggcc ccggcatccg ggcagcccg cggctcggt acctggtggc   720
gcacaacctc ctcctggctc atgccaaagt ctggcatctc tacaatactt ctttccgtcc   780
cactcaggga ggtcaggtgt ccattgccct aagctctcac tggatcaatc ctcgaagaat   840
gaccgaccac agcatcaaag aatgtcaaaa atctctggac tttgtactag gttggtttgc   900
caaacccgta tttattgatg gtgactatcc cgagagcatg aagaataacc tttcatctat   960
tctgcctgat tttactgaat ctgagaaaaa gttcatcaaa ggaactgctg actttttgc   1020
tctttgcttt ggacccacct tgagttttca acttttggac cctcacatga agttccgcca   1080
attggaatct cccaacctga ggcaactgct ttcctggatt gaccttgaat taaccatcc   1140
tcaaatattt attgtgnnna atggctggtt tgtctcaggg accaccaaga gagatgatgc   1200
caaatatatg tattacctca aaaagttcat catggaaacc ttaaaagcca tcaagctgga   1260
tggggtggat gtcatcgggt ataccgcatg gtccctcatg gatggtttcg agtggcacag   1320
aggttacagc atcaggcgtg gactcttcta tgttgacttt ctaagccagg acaagatgtt   1380
gttgccaaag tcttcagcct tgttctacca aaagctgata gagaaaaatg gcttccctcc   1440
tttacctgaa aatcagcccc tagaagggac atttccctgt gactttgctt ggggagttgt   1500
tgacaactac attcaagtag ataccactct gtctcagttt accgacctga atgtttacct   1560
gtgggatgtc caccacagta aaaggcttat taaagtggat ggggttgtga ccaagaagag   1620
gaaatcctac tgtgttgact ttgctgccat ccagccccag atcgctttac tccaggaaat   1680
gcacgttaca cattttcgct tctccctgga ctgggcctg attctccctc tgggtaacca   1740
gtcccaggtg aaccacacca tcctgcagta ctatcgctgc atggccagcg agcttgtccg   1800
tgtcaacatc accccagtgg tggccctgtg gcagcctatg gccccgaacc aaggactgcc   1860
gcgcctcctg gccaggcagg cgcgctggga gaaccccac actgccctgg cctttgcaga   1920
gtatgcccga ctgtgctttc aagagctcgg ccatcacgtc aagctttgga taacgatgaa   1980
```

```
tgagccgtat acaaggaata tgacatacag tgctggccac aaccttctga aggcccatgc    2040
cctggcttgg catgtgtaca atgaaaagtt taggcatgct cagaatggga aaatatccat    2100
agccttgcag gctgattgga tagaacctgc ctgccctttc tcccaaaagg acaaagaggt    2160
ggccgagaga gttttggaat ttgacattgg ctggctggct gagcccattt tcggctctgg    2220
agattatcca tgggtgatga gggactggct gaaccaaaga aacaatttc ttcttcctta     2280 tttcactgaa gatgaaaaaa agctaatcca gggtaccttt gacttttgg ctttaagcca     2340 ttataccacc atccttgtag actcagaaaa agaagatcca ataaaataca atgattacct    2400
agaagtgcaa gaaatgaccg acatcacgtg gctcaactcc cccagtcagg tggcggtagt    2460
gccctggggg ttgcgcaaag tgctgaactg gctgaagttc aagtacggag acctccccat    2520
gtacataata tccaacggaa tcgatgacgg gctgcatgct gaggacgacc agctgagggt    2580
gtattatatg cagaattaca taaacgaagc tctcaaagcc cacatactgg atggtatcaa    2640
tctttgcgga tactttgctt attcgtttaa cgaccgcaca gctccgaggt ttggcctcta    2700
tcgttatgct gcagatcagt ttgagcccaa ggcatccatg aaacattaca ggaaaattat    2760
tgacagcaat ggtttcccgg gcccagaaac tctggaaaga ttttgtccag aagaattcac    2820
cgtgtgtact gagtgcagtt ttttcacac ccgaaag                              2857
```

<210> SEQ ID NO 55
<211> LENGTH: 1704
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1240)..(1242)
<223> OTHER INFORMATION: n is a, c, g, or t

<400> SEQUENCE: 55

```
atgcccgcca gcgccccgcc gcgccgcccg cggccgccgc cgccgtcgct gtcgctgctg      60
ctggtgctgc tgggcctggg cggccgccgc ctgcgtgcgg agccgggcga cggcgcgcag     120
acctgggccc gtgtctcgcg gcctcctgcc cccgaggccg cggcctcct ccagggcacc      180 ttccccgacg gcttcctctg ggccgtgggc agcgccgcct accagaccga gggcggctgg     240
cagcagcacg gcaagggtgc gtccatctgg gacacgttca cccaccaccc cctggcaccc     300
ccgggagact cccggaacgc cagtctgccg ttgggcgccc cgtcgccgct gcagcccgcc     360
accggggacg tagccagcga cagctacaac aacgtcttcc gcgacacgga ggcgctgcgc     420
gagctcgggg tcactcacta ccgcttctcc atctcgtggg cgcgagtgct ccccaatggc     480
agcgcgggcg tccccaaccg cgaggggctg cgctactacc ggcgcctgct ggagcggctg     540
cgggagctgg gcgtgcagcc cgtggtcacc ctgtaccact gggacctgcc ccagcgcctg     600
caggacgcct acgcggctg ggccaaccgc gccctggccg accacttcag ggattacgcg     660
gagctctgct tccgccactt cggcggtcag gtcaagtact ggatcaccat cgacaacccc     720
tacgtggtgg cctggcacgg ctacgccacc gggcgcctgg ccccggcat ccggggcagc      780 ccgcggctcg ggtacctggt ggcgcacaac ctcctcctgg ctcatgccaa gtctggcat      840 ctctacaata cttcttccg tcccactcag ggaggtcagg tgtccattgc cctaagctct      900
cactggatca atcctcgaag aatgaccgac cacagcatca aagaatgtca aaatctctg      960 gactttgtac taggttggtt tgccaaaccc gtatttattg atggtgacta tcccgagagc    1020
```

```
atgaagaata acctttcatc tattctgcct gattttactg aatctgagaa aaagttcatc    1080
aaaggaactg ctgactttt tgctctttgc tttggaccca ccttgagttt caacttttg      1140 gaccctcaca tgaagttccg ccaattggaa tctcccaacc tgaggcaact gctttcctgg    1200
attgaccttg aatttaacca tcctcaaata tttattgtgn nnaatggctg gtttgtctca    1260
gggaccacca agagagatga tgccaaatat atgtattacc tcaaaaagtt catcatggaa    1320
accttaaaag ccatcaagct ggatggggtg gatgtcatcg gtataccgc atggtccctc     1380 atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tccttttacct gaaaatcagc ccctagaagg gacatttccc   1560
tgtgactttg cttggggagt tgttgacaac tacattcaag tagataccac tctgtctcag    1620
tttaccgacc tgaatgttta cctgtgggat gtccaccaca gtaaaaggct tattaaagtg    1680
gatggggttg tgaccaagaa gagg                                           1704
```

<210> SEQ ID NO 56
<211> LENGTH: 1621
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1157)..(1159)
<223> OTHER INFORMATION: n is a, c, g, or t

<400> SEQUENCE: 56

```
ccgccgcctg cgtgcggagc cgggcgacgg cgcgcagacc tgggcccgtg tctcgcggcc    60 tcctgcccc gaggccgcgg gcctcttcca gggcaccttc cccgacggct tcctctgggc    120
cgtgggcagc gccgcctacc agaccgaggg cggctggcag cagcacggca agggtgcgtc    180
catctgggac acgttcaccc accaccccct ggcaccccg ggagactccc ggaacgccag     240
tctgccgttg ggcgccccgt cgccgctgca gcccgccacc ggggacgtag ccagcgacag    300
ctacaacaac gtcttccgcg acacggaggc gctgcgcgag ctcggggtca ctcactaccg    360
cttctccatc tcgtgggcgc gagtgctccc caatggcagc gcgggcgtcc ccaaccgcga    420
ggggctgcgc tactaccggc gcctgctgga gcggctgcgg gagctgggcg tgcagcccgt    480
ggtcaccctg taccactggg acctgccca gcgcctgcag gacgcctacg gcggctgggc     540
caaccgcgcc ctggccgacc acttcaggga ttacgcggag ctctgcttcc gccacttcgg    600
cggtcaggtc aagtactgga tcaccatcga caaccctac gtggtggcct ggcacggcta     660
cgccaccggg cgcctggccc ccggcatccg gggcagcccg cggctcgggt acctggtggc    720
gcacaacctc ctcctggctc atgccaaagt ctggcatctc tacaatactt ctttccgtcc    780
cactcaggga ggtcaggtgt ccattgccct aagctctcac tggatcaatc ctcgaagaat    840
gaccgaccac agcatcaaag aatgtcaaaa atctctggac tttgtactag gttggtttgc    900 caaaccgta tttattgatg gtgactatcc cgagagcatg aagaataacc tttcatctat     960
tctgcctgat tttactgaat ctgagaaaaa gttcatcaaa ggaactgctg acttttttgc    1020
tctttgcttt ggaccacct tgagttttca acttttggac cctcacatga agttccgcca     1080
attggaatct cccaacctga ggcaactgct tcctggatt gaccttgaat ttaaccatcc     1140
tcaaatattt attgtgnnna atggctggtt tgtctcaggg accaccaaga gagatgatgc    1200
caaatatatg tattaccttca aaaagttcat catggaaacc ttaaaagcca tcaagctgga    1260
```

```
tggggtggat gtcatcgggt ataccgcatg gtccctcatg gatggtttcg agtggcacag    1320
aggttacagc atcaggcgtg gactcttcta tgttgacttt ctaagccagg acaagatgtt    1380
gttgccaaag tcttcagcct tgttctacca aaagctgata gagaaaaatg cttccctcc     1440 tttacctgaa aatcagcccc tagaagggac atttccctgt gactttgctt ggggagttgt    1500
tgacaactac attcaagtag ataccactct gtctcagttt accgacctga atgtttacct    1560
gtgggatgtc caccacagta aaaggcttat taaagtggat ggggttgtga ccaagaagag    1620
g                                                                    1621
```

<210> SEQ ID NO 57
<211> LENGTH: 1548
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1141)..(1143)
<223> OTHER INFORMATION: n is a, c, g, or t

<400> SEQUENCE: 57

```
gagccgggcg acggcgcgca gacctgggcc cgtgtctcgc ggcctcctgc ccccgaggcc    60
gcgggcctct tccagggcac cttccccgac ggcttcctct gggccgtggg cagcgccgcc   120
taccagaccg agggcggctg gcagcagcac ggcaagggtg cgtccatctg ggacacgttc   180
acccaccacc ccctggcacc cccggggagac tcccggaacg ccagtctgcc gttgggcgcc   240
ccgtcgccgc tgcagcccgc caccggggac gtagccagcg acagctacaa caacgtcttc   300
cgcgacacgg aggcgctgcg cgagctcggg gtcactcact accgcttctc catctcgtgg   360
gcgcgagtgc tccccaatgg cagcgcgggc gtccccaacc gcgaggggct gcgctactac   420
cggcgcctgc tggagcggct gcgggagctg ggcgtgcagc ccgtggtcac cctgtaccac   480
tgggacctgc cccagcgcct gcaggacgcc tacgcggct gggccaaccg cgccctggcc    540
gaccacttca gggattacgc ggagctctgc ttccgccact cggcggtca ggtcaagtac    600 tggatcacca tcgacaaccc ctacgtggtg gcctggcacg gctacgccac cggcgcctg    660 gccccccggca tccgggggcag cccgcggctc gggtacctgg tggcgcacaa cctcctcctg   720
gctcatgcca aagtctggca tctctacaat acttcttttcc gtcccactca gggaggtcag    780
gtgtccattg ccctaagctc tcactggatc aatcctcgaa gaatgaccga ccacagcatc    840
aaagaatgtc aaaaatctct ggactttgta ctaggttgg ttgccaaacc cgtatttatt     900
gatggtgact atcccgagag catgaagaat aacctttcat ctattctgcc tgatttact     960 gaatctgaga aaagttcat caaaggaact gctgacttt ttgctctttg ctttggaccc      1020
accttgagtt ttcaactttt ggaccctcac atgaagttcc gccaattgga atctcccaac   1080
ctgaggcaac tgctttcctg gattgacctt gaatttaacc atcctcaaat atttattgtg   1140
nnnaatggct ggtttgtctc agggaccacc aagagagatg atgccaaata tatgtattac   1200
ctcaaaaagt tcatcatgga aaccttaaaa gccatcaagc tggatggggt ggatgtcatc   1260
gggtataccg catggtccct catggatggt ttcgagtgg acagaggtta cagcatcagg    1320
cgtggactct tctatgttga ctttctaagc caggacaaga tgttgttgcc aaagtcttca    1380
gccttgttct accaaaagct gatagagaaa aatggcttcc ctcctttacc tgaaaatcag    1440
cccctagaag ggacatttcc ctgtgacttt gcttggggag ttgttgacaa ctacattcaa    1500
```

```
gtagatacca ctctgtctca gtttaccgac ctgaatgttt acctgtgg        1548
```

<210> SEQ ID NO 58
<211> LENGTH: 1647
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1240)..(1242)
<223> OTHER INFORMATION: n is a, c, g, or t

<400> SEQUENCE: 58

```
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag   120
acctgggccc gtgtctcgcg gcctcctgcc cccgaggccg cgggcctctt ccagggcacc   180
ttccccgacg gcttcctctg ggccgtgggc agcgccgcct accagaccga gggcggctgg   240
cagcagcacg gcaagggtgc gtccatctgg gacacgttca cccaccaccc cctggcaccc   300
ccgggagact cccggaacgc cagtctgccg ttgggcgccc cgtcgccgct gcagcccgcc   360
accgggacg tagccagcga cagctacaac aacgtcttcc gcgacacgga ggcgctgcgc   420
gagctcgggg tcactcacta ccgcttctcc atctcgtggg cgcgagtgct ccccaatggc   480
agcgcgggcg tccccaaccg cgaggggctg cgctactacc ggcgcctgct ggagcggctg   540
cgggagctgg gcgtgcagcc cgtggtcacc ctgtaccact gggacctgcc ccagcgcctg   600
caggacgcct acggcggctg gccaaccgc gccctggccg accacttcag ggattacgcg   660
gagctctgct ccgccactt cggcggtcag gtcaagtact ggatcaccat cgacaacccc   720
tacgtggtgg cctggcacgg ctacgccacc gggcgcctgg ccccggcat ccggggcagc   780
ccgcggctcg ggtacctggt ggcgcacaac ctcctcctgg ctcatgccaa agtctggcat   840
ctctacaata cttcttttccg tcccactcag ggaggtcagg tgtccattgc cctaagctct   900
cactggatca atcctcgaag aatgaccgac cacagcatca agaatgtca aaaatctctg   960
gactttgtac taggttggtt tgccaaaccc gtatttattg atggtgacta tcccgagagc  1020
atgaagaata accttttcatc tattctgcct gattttactg aatctgagaa aaagttcatc  1080
aaaggaactg ctgacttttt tgctctttgc tttggaccca ccttgagttt tcaacttttg  1140
gaccctcaca tgaagttccg ccaattggaa tctcccaacc tgaggcaact gcttttcctgg  1200
attgaccttg aatttaacca tcctcaaata tttattgtgn nnaatggctg gtttgtctca  1260
gggaccacca agagagatga tgccaaatat atgtattacc tcaaaaagtt catcatggaa  1320
accttaaaag ccatcaagct ggatggggtg gatgtcatcg ggtataccgc atggtccctc  1380
atggatggtt tcgagtggca cagaggttac agcatcaggc gtggactctt ctatgttgac  1440
tttctaagcc aggacaagat gttgttgcca aagtcttcag ccttgttcta ccaaagctg  1500
atagagaaaa atggcttccc tccttttacct gaaaatcagc cctagaagg gacatttccc  1560
tgtgactttg cttggggagt tgttgacaac tacattcaag taagtcagct gacaaaacca  1620
atcagcagtc tcaccaagcc ctatcac                                      1647
```

<210> SEQ ID NO 59
<211> LENGTH: 1563
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1156)..(1158)
<223> OTHER INFORMATION: n is a, c, g, or t

<400> SEQUENCE: 59

| | | | | | |
|---|---|---|---|---|---|
| cgccgcctgc | gtgcggagcc | gggcgacggc | gcgcagacct | gggcccgtgt | ctcgcggcct | 60 |
| cctgccccg | aggccgcggg | cctcttccag | ggcaccttcc | ccgacggctt | cctctgggcc | 120 |
| gtgggcagcg | ccgcctacca | gaccgagggc | ggctggcagc | agcacggcaa | gggtgcgtcc | 180 |
| atctgggaca | cgttcaccca | ccacccctg | gcaccccgg | gagactcccg | gaacgccagt | 240 |
| ctgccgttgg | gcgccccgtc | gccgctgcag | cccgccaccg | gggacgtagc | cagcgacagc | 300 |
| tacaacaacg | tcttccgcga | cacggaggcg | ctgcgcgagc | tcgggtcac | tcactaccgc | 360 |
| ttctccatct | cgtgggcgcg | agtgctcccc | aatggcagcg | cgggcgtccc | caaccgcgag | 420 |
| gggctgcgct | actaccggcg | cctgctggag | cggctgcggg | agctgggcgt | gcagcccgtg | 480 |
| gtcaccctgt | accactggga | cctgcccag | cgcctgcagg | acgcctacgg | cggctgggcc | 540 |
| aaccgcgccc | tggccgacca | cttcagggat | tacgcggagc | tctgcttccg | ccacttcggc | 600 |
| ggtcaggtca | agtactggat | caccatcgac | aaccccacg | tggtggcctg | gcacggctac | 660 |
| gccaccgggc | gcctggcccc | cggcatccgg | ggcagcccgc | ggctcgggta | cctggtggcg | 720 |
| cacaacctcc | tcctggctca | tgccaaagtc | tggcatctct | acaatacttc | tttccgtccc | 780 |
| actcagggag | gtcaggtgtc | cattgcccta | agctctcact | ggatcaatcc | tcgaagaatg | 840 |
| accgaccaca | gcatcaaaga | atgtcaaaaa | tctctggact | ttgtactagg | ttggtttgcc | 900 |
| aaacccgtat | ttattgatgg | tgactatccc | gagagcatga | agaataacct | ttcatctatt | 960 |
| ctgcctgatt | ttactgaatc | tgagaaaaag | ttcatcaaag | gaactgctga | ctttttttgct | 1020 |
| cttttgctttg | gacccacctt | gagttttcaa | cttttggacc | ctcacatgaa | gttccgccaa | 1080 |
| ttggaatctc | ccaacctgag | gcaactgctt | tcctggattg | accttgaatt | taaccatcct | 1140 |
| caaatatttta | ttgtgnnnaa | tggctggttt | gtctcaggga | ccaccaagag | agatgatgcc | 1200 |
| aaatatatgt | attacctcaa | aaagttcatc | atggaaacct | aaaagccat | caagctggat | 1260 |
| ggggtggatg | tcatcgggta | taccgcatgg | tccctcatgg | atggtttcga | gtggcacaga | 1320 |
| ggttacagca | tcaggcgtgg | actcttctat | gttgactttc | taagccagga | caagatgttg | 1380 |
| ttgccaaagt | cttcagcctt | gttctaccaa | aagctgatag | agaaaaatgg | cttccctcct | 1440 |
| ttacctgaaa | atcagcccct | agaagggaca | tttccctgtg | actttgcttg | gggagttgtt | 1500 |
| gacaactaca | ttcaagtaag | tcagctgaca | aaaccaatca | gcagtctcac | caagccctat | 1560 |
| cac | | | | | | 1563 |

<210> SEQ ID NO 60
<211> LENGTH: 1548
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (1141)..(1143)
<223> OTHER INFORMATION: n is a, c, g, or t

<400> SEQUENCE: 60

| | | | | | |
|---|---|---|---|---|---|
| gagccgggcg | acggcgcgca | gacctgggcc | cgtgtctcgc | ggcctcctgc | cccgaggcc | 60 |
| gcgggcctct | tccagggcac | cttccccgac | ggcttcctct | gggccgtggg | cagcgccgcc | 120 |

```
taccagaccg agggcggctg gcagcagcac ggcaagggtg cgtccatctg ggacacgttc    180
acccaccacc ccctggcacc cccgggagac tcccggaacg ccagtctgcc gttgggcgcc    240
ccgtcgccgc tgcagcccgc caccggggac gtagccagcg acagctacaa caacgtcttc    300
cgcgacacgg aggcgctgcg cgagctcggg gtcactcact accgcttctc catctcgtgg    360
gcgcgagtgc tccccaatgg cagcgcgggc gtccccaacc gcgaggggct gcgctactac    420
cggcgcctgc tggagcggct gcgggagctg gcgtgcagc ccgtggtcac cctgtaccac    480
tgggacctgc cccagcgcct gcaggacgcc tacgcggct gggccaaccg cgccctggcc    540
gaccacttca gggattacgc ggagctctgc ttccgccact cggcggtca ggtcaagtac    600 tggatcacca tcgacaaccc ctacgtggtg gcctggcacg gctacgccac cgggcgcctg    660 gccccggca tcggggcag cccgcggctc gggtacctgg tggcgcacaa cctcctcctg    720
gctcatgcca agtctggca tctctacaat acttctttcc gtcccactca gggaggtcag    780
gtgtccattg ccctaagctc tcactggatc aatcctcgaa gaatgaccga ccacagcatc    840
aaagaatgtc aaaaatctct ggactttgta ctaggttggt ttgccaaacc cgtatttatt    900
gatggtgact atcccgagag catgaagaat aacctttcat ctattctgcc tgattttact    960
gaatctgaga aaaagttcat caaaggaact gctgactttt ttgctctttg ctttggaccc   1020
accttgagtt ttcaactttt ggaccctcac atgaagttcc gccaattgga atctcccaac   1080
ctgaggcaac tgctttcctg gattgacctt gaatttaacc atcctcaaat atttattgtg   1140
nnnaatggct ggtttgtctc agggaccacc aagagagatg atgccaaata tatgtattac   1200
ctcaaaaagt tcatcatgga aaccttaaaa gccatcaagc tggatggggt ggatgtcatc   1260
gggtataccg catggtccct catggatggt ttcgagtggc acagaggtta cagcatcagg   1320
cgtggactct tctatgttga cttcctaagc caggacaaga tgttgttgcc aaagtcttca   1380
gccttgttct accaaaagct gatagagaaa aatggcttcc ctcctttacc tgaaaatcag   1440
cccctagaag ggacatttcc ctgtgacttt gcttggggag ttgttgacaa ctacattcaa   1500
gtaagtcagc tgacaaaacc aatcagcagt ctcaccaagc cctatcac                1548
```

<210> SEQ ID NO 61  
<211> LENGTH: 3036  
<212> TYPE: DNA  
<213> ORGANISM: Artificial  
<220> FEATURE:  
<223> OTHER INFORMATION: DNA encoding recombinant variant polypeptide  
<220> FEATURE:  
<221> NAME/KEY: misc_feature  
<222> LOCATION: (712)..(714)  
<223> OTHER INFORMATION: n is a, c, g, or t

<400> SEQUENCE: 61

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtgtctcgcg gcctcctgcc cccgaggccg cgggcctctt ccagggcacc    180
ttccccgacg gcttcctctg ggccgtgggc agcgccgcct accagaccga gggcggctgg    240
cagcagcacg gcaagggtgc gtccatctgg gacacgttca cccaccaccc cctggcaccc    300
ccgggagact cccggaacgc cagtctgccg ttgggcgccc gtcgccgct gcagcccgcc    360 accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
```

```
cgggagctgg gcgtgcagcc cgtggtcacc ctgtaccact gggacctgcc ccagcgcctg   600
caggacgcct acggcggctg ggccaaccgc gccctggccg accacttcag ggattacgcg   660
gagctctgct tccgccactt cggcggtcag gtcaagtact ggatcaccat cnnnaacccc   720
tacgtggtgg cctggcacgg ctacgccacc gggcgcctgg cccccggcat ccggggcagc   780
ccgcggctcg ggtacctggt ggcgcacaac ctcctcctgg ctcatgccaa agtctggcat   840
ctctacaata cttctttccg tcccactcag ggaggtcagg tgtccattgc cctaagctct   900
cactggatca atcctcgaag aatgaccgac cacagcatca agaatgtca aaaatctctg    960
gactttgtac taggttggtt tgccaaaccc gtatttattg atggtgacta tcccgagagc  1020
atgaagaata accttcatc tattctgcct gattttactg aatctgagaa aaagttcatc   1080
aaaggaactg ctgactttt tgctctttgc tttggaccca ccttgagttt tcaacttttg   1140
gaccctcaca tgaagttccg ccaattggaa tctcccaacc tgaggcaact gctttcctgg  1200
attgaccttg aatttaacca tcctcaaata tttattgtgg aaaatggctg gtttgtctca  1260
gggaccacca agagagatga tgccaaatat atgtattacc tcaaaaagtt catcatggaa  1320
accttaaaag ccatcaagct ggatgggtg gatgtcatcg gtataccgc atggtccctc   1380
atggatggtt tcgagtggca cagaggttac agcatcaggc gtggactctt ctatgttgac  1440
tttctaagcc aggacaagat gttgttgcca aagtcttcag ccttgttcta ccaaaagctg  1500
atagagaaaa atggcttccc tcctttacct gaaaatcagc ccctagaagg gacatttccc  1560
tgtgactttg cttggggagt tgttgacaac tacattcaag tagataccac tctgtctcag  1620
tttaccgacc tgaatgttta cctgtgggat gtccaccaca gtaaaaggct tattaaagtg  1680
gatgggttg tgaccaagaa gaggaaatcc tactgtgttg actttgctgc catccagccc  1740
cagatcgctt tactccagga aatgcacgtt acacattttc gcttctccct ggactgggcc  1800
ctgattctcc ctctgggtaa ccagtcccag gtgaaccaca ccatcctgca gtactatcgc  1860
tgcatggcca gcgagcttgt ccgtgtcaac atcaccccag tggtggccct gtggcagcct  1920
atggccccga accaaggact gccgcgcctc ctggccaggc agggcgcctg ggagaacccc  1980
tacactgccc tggcctttgc agagtatgcc cgactgtgct ttcaagagct cggccatcac  2040
gtcaagcttt ggataacgat gaatgagccg tatacaagga atatgacata cagtgctggc  2100
cacaaccttc tgaaggccca tgccctggct tggcatgtgt acaatgaaaa gtttaggcat  2160
gctcagaatg ggaaaatatc catagccttg caggctgatt ggatagaacc tgcctgccct  2220
ttctcccaaa aggacaaaga ggtggccgag agagttttgg aatttgacat tggctggctg  2280
gctgagccca ttttcggctc tggagattat ccatgggtga tgagggactg gctgaaccaa  2340
agaaacaatt ttcttcttcc ttatttcact gaagatgaaa aaaagctaat ccagggtacc  2400
tttgactttt tggctttaag ccattatacc accatccttg tagactcaga aaagaagat   2460
ccaataaaat acaatgatta cctagaagtg caagaaatga ccgacatcac gtggctcaac  2520
tcccccagtc aggtggcggt agtgcctgg gggttgcgca agtgctgaa ctggctgaag   2580
ttcaagtacg gagacctccc catgtacata atatccaacg gaatcgatga cgggctgcat  2640
gctgaggacg accagctgag ggtgtattat atgcagaatt acataaacga agctctcaaa  2700
gcccacatac tggatggtat caatctttgc ggatactttg cttattcgtt taacgaccgc  2760
acagctccga ggtttggcct ctatcgttat gctgcagatc agtttgagcc caaggcatcc  2820
atgaaacatt acaggaaaat tattgacagc aatggtttcc cgggcccaga aactctggaa  2880
```

| | |
|---|---|
| agattttgtc cagaagaatt caccgtgtgt actgagtgca gttttttttca cacccgaaag | 2940 |
| tctttactgg ctttcatagc ttttctattt tttgcttcta ttatttctct ctcccttata | 3000 |
| ttttactact cgaagaaagg cagaagaagt tacaaa | 3036 |

<210> SEQ ID NO 62
<211> LENGTH: 2949
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (625)..(627)
<223> OTHER INFORMATION: n is a, c, g, or t

<400> SEQUENCE: 62

| | |
|---|---|
| cgcctgcgtg cggagccggg cgacggcgcg cagacctggg cccgtgtctc gcggcctcct | 60 |
| gcccccgagg ccgcgggcct cttccagggc accttccccg acggcttcct ctgggccgtg | 120 |
| ggcagcgccg cctaccagac cgaggcggc tggcagcagc acggcaaggg tgcgtccatc | 180 |
| tgggacacgt tcacccacca ccccctggca ccccgggag actcccggaa cgccagtctg | 240 |
| ccgttgggcg ccccgtcgcc gctgcagccc gccaccgggg acgtagccag cgacagctac | 300 |
| aacaacgtct tccgcgacac ggaggcgctg cgcgagctcg gggtcactca ctaccgcttc | 360 |
| tccatctcgt gggcgcgagt gctccccaat ggcagcgcgg gcgtccccaa ccgcgagggg | 420 |
| ctgcgctact accggcgcct gctggagcgg ctgcgggagc tgggcgtgca gcccgtggtc | 480 |
| accctgtacc actgggaccct gccccagcgc ctgcaggacg cctacggcgg ctgggccaac | 540 |
| cgcgccctgg ccgaccactt cagggattac gcggagctct gcttccgcca cttcggcggt | 600 |
| caggtcaagt actggatcac catcnnnaac ccctacgtgg tggcctggca cggctacgcc | 660 |
| accgggcgcc tggcccccgg catccggggc agcccgcggc tcgggtacct ggtggcgcac | 720 |
| aacctcctcc tggctcatgc caaagtctgg catctctaca atacttcttt ccgtcccact | 780 |
| cagggaggtc aggtgtccat tgccctaagc tctcactgga tcaatcctcg aagaatgacc | 840 |
| gaccacagca tcaaagaatg tcaaaaatct ctggactttg tactaggttg gtttgccaaa | 900 |
| cccgtatttta ttgatggtga ctatcccgag agcatgaaga ataaccttc atctattctg | 960 |
| cctgatttta ctgaatctga aaaaagttc atcaaaggaa ctgctgactt ttttgctctt | 1020 |
| tgctttggac ccaccttgag ttttcaactt ttggaccctc acatgaagtt ccgccaattg | 1080 |
| gaatctccca acctgaggca actgctttcc tggattgacc ttgaatttaa ccatcctcaa | 1140 |
| atatttattg tggaaaatgg ctggtttgtc tcagggacca ccaagagaga tgatgccaaa | 1200 |
| tatatgtatt acctcaaaaa gttcatcatg gaaaccttaa aagccatcaa gctggatggg | 1260 |
| gtggatgtca tcgggtatac cgcatggtcc ctcatggatg gtttcgagtg gcacagaggt | 1320 |
| tacagcatca ggcgtggact cttctatgtt gactttctaa gccaggacaa gatgttgttg | 1380 |
| ccaaagtctt cagccttgtt ctaccaaaag ctgatagaga aaaatggctt ccctcctttta | 1440 |
| cctgaaaatc agcccctaga agggacattt ccctgtgact ttgcttgggg agttgttgac | 1500 |
| aactacattc aagtagatac cactctgtct cagtttaccg acctgaatgt ttacctgtgg | 1560 |
| gatgtccacc acagtaaaag gcttattaaa gtggatgggg ttgtgaccaa gagaggaaa | 1620 |
| tcctactgtg ttgactttgc tgccatccag ccccagatcg ctttactcca ggaaatgcac | 1680 |
| gttacacatt ttcgcttctc cctggactgg gccctgattc tccctctggg taaccagtcc | 1740 |
| caggtgaacc acaccatcct gcagtactat cgctgcatgg ccagcgagct tgtccgtgtc | 1800 |

```
aacatcaccc cagtggtggc cctgtggcag cctatggccc cgaaccaagg actgccgcgc    1860
ctcctggcca ggcagggcgc ctgggagaac ccctacactg ccctggcctt tgcagagtat    1920
gcccgactgt gctttcaaga gctcggccat cacgtcaagc tttggataac gatgaatgag    1980
ccgtatacaa ggaatatgac atacagtgct ggccacaacc ttctgaaggc ccatgccctg    2040
gcttggcatg tgtacaatga aaagtttagg catgctcaga tgggaaaat atccatagcc     2100 ttgcaggcta attggataga acctgcctgc cctttctccc aaaaggacaa agaggtggcc    2160
gagagagttt tggaatttga cattggctgg ctggctgagc ccattttcgg ctctggagat    2220
tatccatggg tgatgaggga ctggctgaac caaagaaaca attttcttct tccttatttc    2280
actgaagatg aaaaaaagct aatccagggt acctttgact ttttggcttt aagccattat    2340
accaccatcc ttgtagactc agaaaaagaa gatccaataa aatacaatga ttacctagaa    2400
gtgcaagaaa tgaccgacat cacgtggctc aactccccca gtcaggtggc ggtagtgccc    2460
tgggggttgc gcaaagtgct gaactggctg aagttcaagt acggagacct ccccatgtac    2520
ataatatcca acggaatcga tgacgggctg catgctgagg acgaccagct gagggtgtat    2580
tatatgcaga attacataaa cgaagctctc aaagcccaca tactggatgg tatcaatctt    2640
tgcggatact ttgcttattc gtttaacgac cgcacagctc cgaggtttgg cctctatcgt    2700
tatgctgcag atcagtttga gcccaaggca tccatgaaac attacaggaa aattattgac    2760
agcaatggtt tcccgggccc agaaactctg gaaagatttt gtccagaaga attcaccgtg    2820
tgtactgagt gcagttttt tcacacccga aagtctttac tggctttcat agcttttcta    2880 tttttgctt ctattatttc tctctccctt atattttact actcgaagaa aggcagaaga    2940
agttacaaa                                                           2949
```

<210> SEQ ID NO 63
<211> LENGTH: 2940
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t

<400> SEQUENCE: 63

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtgtctcgcg gcctcctgcc cccgaggccg cgggcctctt ccagggcacc    180
ttccccgacg gcttcctctg ggccgtgggc agcgccgcct accagaccga gggcggctgg    240
cagcagcacg gcaagggtgc gtccatctgg gacacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acgcgggctg ggccaaccgc gccctggccg accacttcag ggattacgcg    660
gagctctgct tccgccactt cggcggtcag gtcaagtact ggatcaccat cnnnaacccc    720
```

```
tacgtggtgg cctggcacgg ctacgccacc gggcgcctgg cccccggcat ccggggcagc    780
ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaaatctctg     960 gactttgtac taggttggtt tgccaaaccc gtatttattg atggtgacta tcccgagagc   1020
atgaagaata acctttcatc tattctgcct gattttactg aatctgagaa aaagttcatc   1080
aaaggaactg ctgactttt tgctctttgc tttggaccca ccttgagttt tcaacttttg    1140
gaccctcaca tgaagttccg ccaattggaa tctcccaacc tgaggcaact gctttcctgg   1200
attgaccttg aatttaacca tcctcaaata tttattgtgg aaaatggctg gtttgtctca   1260
gggaccacca agagagatga tgccaaatat atgtattacc tcaaaaagtt catcatggaa   1320
accttaaaag ccatcaagct ggatggggtg gatgtcatcg ggtataccgc atggtccctc   1380
atggatggtt tcgagtggca cagaggttac agcatcaggc gtggactctt ctatgttgac   1440
tttctaagcc aggacaagat gttgttgcca aagtcttcag ccttgttcta ccaaaagctg   1500
atagagaaaa atggcttccc tcctttacct gaaaatcagc ccctagaagg gacatttccc   1560
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtggccct gtggcagcct   1920
atggccccga accaaggact gccgcgcctc ctggccaggc agggcgcctg ggagaacccc   1980
tacactgccc tggccttttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg gaaaatatc catagccttg caggctgatt ggatagaacc tgcctgccct   2220
ttctcccaaa aggacaaaga ggtggccgag agagttttgg aatttgacat tggctggctg   2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggctttaag ccattatacc accatccttg tagactcaga aaaagaagat   2460
ccaataaaat acaatgatta cctagaagtg caagaaatga ccgacatcac gtggctcaac   2520
tcccccagtc aggtggcggt agtgcccctgg gggttgcgca aagtgctgaa ctggctgaag   2580
ttcaagtacg agagacctccc catgtacata atatccaacg gaatcgatga cgggctgcat   2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagatc agtttgagcc caaggcatcc   2820
atgaaacatt acaggaaaat tattgacagc aatggttttcc cgggcccaga aactctggaa   2880
agattttgtc cagaagaatt caccgtgtgt actgagtgca gttttttttca cacccgaaag   2940
```

<210> SEQ ID NO 64
<211> LENGTH: 2857
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (629)..(631)
<223> OTHER INFORMATION: n is a, c, g, or t

<400> SEQUENCE: 64

```
ccgccgcctg cgtgcggagc cgggcgacgg cgcgcagacc tgggcccgtg tctcgcggcc      60
tcctgccccc gaggccgcgg gcctcttcca gggcaccttc cccgacggct tcctctgggc     120
cgtgggcagc gccgcctacc agaccgaggg cggctggcag cagcacggca agggtgcgtc     180
catctgggac acgttcaccc accacccct ggcaccccg ggagactccc ggaacgccag       240
tctgccgttg ggcgccccgt cgccgctgca gcccgccacc ggggacgtag ccagcgacag     300
ctacaacaac gtcttccgcg acacggaggc gctgcgcgag ctcggggtca ctcactaccg     360
cttctccatc tcgtgggcgc gagtgctccc caatggcagc gcgggcgtcc ccaaccgcga     420
ggggctgcgc tactaccggc gcctgctgga gcggctgcgg gagctgggcg tgcagcccgt     480
ggtcaccctg taccactggg acctgcccca gcgcctgcag gacgcctacg gcggctgggc     540
caaccgcgcc ctggccgacc acttcaggga ttacgcggag ctctgcttcc gccacttcgg     600
cggtcaggtc aagtactgga tcaccatcnn naaccctac gtggtggcct ggcacggcta      660
cgccaccggg cgcctggccc ccggcatccg gggcagcccg cggctcgggt acctggtggc     720
gcacaacctc ctcctggctc atgccaaagt ctggcatctc tacaatactt ctttccgtcc     780
cactcaggga ggtcaggtgt ccattgccct aagctctcac tggatcaatc ctcgaagaat     840
gaccgaccac agcatcaaag aatgtcaaaa atctctggac tttgtactag gttggtttgc     900
caaacccgta tttattgatg gtgactatcc cgagagcatg aagaataacc tttcatctat     960
tctgcctgat tttactgaat ctgagaaaaa gttcatcaaa ggaactgctg acttttttgc    1020
tctttgcttt ggacccacct tgagttttca acttttggac cctcacatga agttccgcca    1080
attggaatct cccaacctga ggcaactgct ttcctggatt gaccttgaat ttaaccatcc    1140
tcaaatattt attgtggaaa atggctggtt tgtctcaggg accaccaaga gagatgatgc    1200
caaatatatg tattacctca aaaagttcat catggaaacc ttaaaagcca tcaagctgga    1260
tgggggtggat gtcatcgggt ataccgcatg gtccctcatg gatggtttcg agtggcacag    1320
aggttacagc atcaggcgtg gactcttcta tgttgacttt ctaagccagg acaagatgtt    1380
gttgccaaag tcttcagcct tgttctacca aaagctgata gagaaaaatg gcttccctcc    1440
tttacctgaa aatcagcccc tagaagggac atttccctgt gactttgctt ggggagttgt    1500
tgacaactac attcaagtag ataccactct gtctcagttt accgacctga atgtttacct    1560
gtgggatgtc caccacagta aaaggcttat taaagtggat gggggttgtga ccaagaagag    1620
gaaatcctac tgtgttgact ttgctgccat ccagcccag atcgctttac tccaggaaat    1680
gcacgttaca cattttcgct ctccctgga ctgggcctg attctccctc tgggtaacca      1740
gtcccaggtg aaccacacca tcctgcagta ctatcgctgc atggccagcg agcttgtccg    1800
tgtcaacatc accccagtgg tggccctgtg gcagcctatg gccccgaacc aaggactgcc    1860
gcgcctcctg gccaggcagg gcgccctggga gaaccctac actgccctgg cctttgcaga    1920
gtatgcccga ctgtgctttc aagagctcgg ccatcacgtc aagctttgga taacgatgaa    1980
tgagccgtat acaaggaata tgacatacag tgctggccac aaccttctga aggcccatgc    2040
cctggcttgg catgtgtaca atgaaaagtt taggcatgct cagaatggga aaatatccat    2100
```

| | |
|---|---|
| agccttgcag gctgattgga tagaacctgc ctgcccttc tcccaaaagg acaaagaggt | 2160 |
| ggccgagaga gttttggaat ttgacattgg ctggctggct gagcccattt tcggctctgg | 2220 |
| agattatcca tgggtgatga gggactggct gaaccaaaga aacaatttc ttcttcctta | 2280 |
| tttcactgaa gatgaaaaaa agctaatcca gggtaccttt gacttttgg ctttaagcca | 2340 |
| ttataccacc atccttgtag actcagaaaa agaagatcca ataaaataca atgattacct | 2400 |
| agaagtgcaa gaaatgaccg acatcacgtg gctcaactcc cccagtcagg tggcggtagt | 2460 |
| gccctggggg ttgcgcaaag tgctgaactg gctgaagttc aagtacggag acctccccat | 2520 |
| gtacataata tccaacggaa tcgatgacgg gctgcatgct gaggacgacc agctgagggt | 2580 |
| gtattatatg cagaattaca taaacgaagc tctcaaagcc cacatactgg atggtatcaa | 2640 |
| tctttgcgga tactttgctt attcgtttaa cgaccgcaca gctccgaggt ttggcctcta | 2700 |
| tcgttatgct gcagatcagt tgagcccaa ggcatccatg aaacattaca ggaaaattat | 2760 |
| tgacagcaat ggtttcccgg gcccagaaac tctggaaaga ttttgtccag aagaattcac | 2820 |
| cgtgtgtact gagtgcagtt tttttcacac ccgaaag | 2857 |

<210> SEQ ID NO 65
<211> LENGTH: 1704
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t

<400> SEQUENCE: 65

| | |
|---|---|
| atgcccgcca gcgccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc gtgtctcgcg gcctcctgcc cccgaggccg cgggcctctt ccagggcacc | 180 |
| ttccccgacg gcttcctctg gccgtgggc agcgccgcct accagaccga gggcggctgg | 240 |
| cagcagcacg gcaagggtgc gtccatctgg gacacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggcg tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |
| caggacgcct acggcggctg gccaaccgc gccctggccg accacttcag ggattacgcg | 660 |
| gagctctgct tccgccactt cggcggtcag gtcaagtact ggatcaccat cnnnaacccc | 720 |
| tacgtggtgg cctggcacgg ctacgccacc gggcgcctgg cccccggcat ccggggcagc | 780 |
| ccgcggctcg ggtacctggt ggcgcacaac ctcctcctgg ctcatgccaa agtctggcat | 840 |
| ctctacaata cttctttccg tcccactcag ggaggtcagg tgtccattgc cctaagctct | 900 |
| cactggatca atcctcgaag aatgaccgac cacagcatca aagaatgtca aaatctctg | 960 |
| gactttgtac taggttggtt tgccaaaccc gtatttattg atggtgacta tcccgagagc | 1020 |
| atgaagaata acctttcatc tattctgcct gattttactg aatctgagaa aaagttcatc | 1080 |
| aaaggaactg ctgactttt tgctctttgc tttggaccca ccttgagttt tcaacttttg | 1140 |
| gaccctcaca tgaagttccg ccaattggaa tctcccaacc tgaggcaact gctttcctgg | 1200 |

```
attgaccttg aatttaacca tcctcaaata tttattgtgg aaaatggctg gtttgtctca   1260
gggaccacca agagagatga tgccaaatat atgtattacc tcaaaaagtt catcatggaa   1320
accttaaaag ccatcaagct ggatggggtg gatgtcatcg ggtataccgc atggtccctc   1380
atggatggtt tcgagtggca cagaggttac agcatcaggc gtggactctt ctatgttgac   1440
tttctaagcc aggacaagat gttgttgcca agtcttcag ccttgttcta ccaaaagctg    1500
atagagaaaa atggcttccc tcctttacct gaaaatcagc cctagaagg acatttccc     1560 tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gagg                                          1704
```

<210> SEQ ID NO 66
<211> LENGTH: 1621
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (629)..(631)
<223> OTHER INFORMATION: n is a, c, g, or t

<400> SEQUENCE: 66

```
ccgccgcctg cgtgcggagc cgggcgacgg cgcgcagacc tgggcccgtg tctcgcggcc    60
tcctgccccc gaggccgcgg gcctcttcca gggcaccttc cccgacggct tcctctgggc   120
cgtgggcagc gccgcctacc agaccgaggg cggctggcag cagcacggca agggtgcgtc   180
catctgggac acgttcaccc accacccct ggcacccccg ggagactccc ggaacgccag    240
tctgccgttg ggcgccccgt cgccgctgca gcccgccacc ggggacgtag ccagcgacag   300
ctacaacaac gtcttccgcg cacggaggc gctgcgcgag ctcggggtca ctcactaccg    360
cttctccatc tcgtgggcgc gagtgctccc caatggcagc gcgggcgtcc ccaaccgcga   420
ggggctgcgc tactaccggc gcctgctgga gcggctgcgg gagctgggcg tgcagcccgt   480
ggtcaccctg taccactggg acctgccccc agcgcctgcag gacgcctacg gcggctgggc   540
caaccgcgcc ctggccgacc acttcaggga ttacgcggag ctctgcttcc gccacttcgg   600
cggtcaggtc aagtactgga tcaccatcnn naacccctac gtggtggcct ggcacggcta   660
cgccaccggg cgcctggccc ccggcatccg gggcagcccg cggctcgggt acctggtggc   720
gcacaacctc ctcctggctc atgccaaagt ctggcatctc tacaatactt ctttccgtcc   780
cactcaggga ggtcaggtgt ccattgccct aagctctcac tggatcaatc ctcgaagaat   840
gaccgaccac agcatcaaag aatgtcaaaa atctctggac tttgtactag gttggtttgc   900
caaacccgta tttattgatg gtgactatcc cgagagcatg aagaataacc tttcatctat    960
tctgcctgat tttactgaat ctgagaaaaa gttcatcaaa ggaactgctg acttttttgc   1020 tctttgctttt ggacccacct tgagttttca acttttggac cctcacatga agttccgcca   1080
attggaatct cccaacctga ggcaactgct ttcctggatt gaccttgaat ttaaccatcc   1140
tcaaatattt attgtggaaa atggctggtt tgtctcaggg accaccaaga gagatgatgc   1200
caaatatatg tattacctca aaaagttcat catggaaacc ttaaaagcca tcaagctgga   1260
tggggtggat gtcatcgggt ataccgcatg gtccctcatg gatggtttcg agtggcacag   1320
aggttacagc atcaggcgtg gactcttcta tgttgacttt ctaagccagg acaagatgtt   1380
```

```
gttgccaaag tcttcagcct tgttctacca aaagctgata gagaaaaatg gcttccctcc      1440
tttacctgaa aatcagcccc tagaagggac atttccctgt gactttgctt ggggagttgt      1500
tgacaactac attcaagtag ataccactct gtctcagttt accgacctga atgtttacct      1560
gtgggatgtc caccacagta aaaggcttat taaagtggat ggggttgtga ccaagaagag      1620
g                                                                     1621
```

<210> SEQ ID NO 67
<211> LENGTH: 1548
<212> TYPE: DNA
<213> ORGANISM: Artificial
<220> FEATURE:
<223> OTHER INFORMATION: DNA encoding recombinant polypeptide
<220> FEATURE:
<221> NAME/KEY: misc_feature
<222> LOCATION: (613)..(615)
<223> OTHER INFORMATION: n is a, c, g, or t

<400> SEQUENCE: 67

```
gagccgggcg acggcgcgca gacctgggcc cgtgtctcgc ggcctcctgc ccccgaggcc        60
gcgggcctct tccagggcac cttccccgac ggcttcctct gggccgtggg cagcgccgcc       120
taccagaccg agggcggctg gcagcagcac ggcaagggtg cgtccatctg ggacacgttc       180
acccaccacc ccctggcacc cccgggagac tcccggaacg ccagtctgcc gttgggcgcc       240
ccgtcgccgc tgcagcccgc caccggggac gtagccagcg acagctacaa caacgtcttc       300
cgcgacacgg aggcgctgcg cgagctcggg gtcactcact accgcttctc catctcgtgg       360
gcgcgagtgc tccccaatgg cagcgcgggc gtccccaacc gcgaggggct gcgctactac       420
cggcgcctgc tggagcggct gcgggagctg ggcgtgcagc ccgtggtcac cctgtaccac       480
tgggacctgc cccagcgcct gcaggacgcc tacggcggct gggccaaccg cgccctggcc       540
gaccacttca gggattacgc ggagctctgc ttccgccact cggcggtca ggtcaagtac        600 tggatcacca tcnnnaaccc ctacgtggtg ggctggcacg gctacgccac cgggcgcctg       660
gcccccggca tccggggcag cccgcggctc gggtacctgg tggcgcacaa cctcctcctg       720
gctcatgcca aagtctggca tctctacaat acttctttcc gtcccactca gggaggtcag       780
gtgtccattg ccctaagctc tcactggatc aatcctcgaa gaatgaccga ccacagcatc       840
aaagaatgtc aaaatctctc tggactttgta ctaggttggt ttgccaaacc cgtatttatt       900
gatggtgact atcccgagag catgaagaat aacctttcat ctattctgcc tgatttact        960 gaatctgaga aaaagttcat caaaggaact gctgactttt ttgctctttg ctttggaccc      1020
accttgagtt ttcaactttt ggaccctcac atgaagttcc gccaattgga atctcccaac      1080
ctgaggcaac tgctttcctg gattgacctt gaatttaacc atcctcaaat atttattgtg      1140
gaaaatggct ggtttgtctc agggaccacc aagagagatg atgccaaata tatgtattac      1200
ctcaaaaagt tcatcatgga aaccttaaaa gccatcaagc tggatggggt ggatgtcatc      1260
gggtataccg catggtccct catggatggt ttcgagtgg acagaggtta cagcatcagg      1320
cgtggactct tctatgttga ctttctaagc caggacaaga tgttgttgcc aaagtcttca      1380
gccttgttct accaaaagct gatagagaaa aatggcttcc ctcctttacc tgaaaatcag      1440
cccctagaag ggacatttcc ctgtgacttt gcttgggag ttgttgacaa ctacattcaa       1500
gtagatacca ctctgtctca gtttaccgac ctgaatgttt acctgtgg                   1548
```

<210> SEQ ID NO 68
<211> LENGTH: 1647

```
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t

<400> SEQUENCE: 68
atgcccgcca gcgccccgcc gcgccgcccg cggccgccgc cgccgtcgct gtcgctgctg      60
ctggtgctgc tgggcctggg cggccgccgc ctgcgtgcgg agccgggcga cggcgcgcag     120
acctgggccc gtgtctcgcg gcctcctgcc cccgaggccg cgggcctctt ccagggcacc     180
ttccccgacg gcttcctctg ggccgtgggc agcgccgcct accagaccga gggcggctgg     240
cagcagcacg gcaagggtgc gtccatctgg gacacgttca cccaccaccc cctggcaccc     300
ccgggagact cccggaacgc cagtctgccg ttgggcgccc cgtcgccgct gcagcccgcc     360
accggggacg tagccagcga cagctacaac aacgtcttcc gcgacacgga ggcgctgcgc     420
gagctcgggg tcactcacta ccgcttctcc atctcgtggg cgcgagtgct ccccaatggc     480
agcgcgggcg tccccaaccg cgaggggctg cgctactacc ggcgcctgct ggagcggctg     540
cgggagctgg gcgtgcagcc cgtggtcacc ctgtaccact gggacctgcc ccagcgcctg     600
caggacgcct acgcggctg ggccaaccgc gccctggccg accacttcag ggattacgcg     660
gagctctgct tccgccactt cggcggtcag gtcaagtact ggatcaccat cnnnaaccccc     720
tacgtggtgg cctggcacgg ctacgccacc gggcgcctgg cccccggcat ccggggcagc     780
ccgcggctcg ggtacctggt ggcgcacaac ctcctcctgg ctcatgccaa agtctggcat     840
ctctacaata cttctttccg tcccactcag ggaggtcagg tgtccattgc cctaagctct     900
cactggatca atcctcgaag aatgaccgac cacagcatca agaatgtca aaaatctctg      960
gactttgtac taggttggtt tgccaaaccc gtatttattg atggtgacta tcccgagagc    1020
atgaagaata acctttcatc tattctgcct gattttactg aatctgagaa aaagttcatc    1080
aaaggaactg ctgactttt tgctctttgc tttggaccca ccttgagttt caactttttg    1140
gaccctcaca tgaagttccg ccaattggaa tctcccaacc tgaggcaact gctttcctgg    1200
attgaccttg aatttaacca tcctcaaata tttattgtgg aaaatggctg gtttgtctca    1260
gggaccacca agagagatga tgccaaatat atgtattacc tcaaaaagtt catcatgaa    1320
accttaaaag ccatcaagct ggatggggtg gatgtcatcg ggtataccgc atggtccctc    1380
atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tcctttacct gaaaatcagc cctagaagg gacatttccc    1560
tgtgactttg cttggggagt gtttgacaac tacattcaag taagtcagct gacaaaacca    1620
atcagcagtc tcaccaagcc ctatcac                                        1647

<210> SEQ ID NO 69
<211> LENGTH: 1563
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (628)..(630)
<223> OTHER INFORMATION: n is a, c, g, or t
```

<400> SEQUENCE: 69

```
cgccgcctgc gtgcggagcc gggcgacggc gcgcagacct gggcccgtgt ctcgcggcct      60
cctgccccg aggccgcggg cctcttccag ggcaccttcc ccgacggctt cctctgggcc     120
gtgggcagcg ccgcctacca gaccgagggc ggctggcagc agcacggcaa gggtgcgtcc     180
atctgggaca cgttcaccca ccaccccctg gcaccccgg gagactcccg gaacgccagt      240
ctgccgttgg gcgccccgtc gccgctgcag cccgccaccg gggacgtagc cagcgacagc     300
tacaacaacg tcttccgcga cacggaggcg ctgcgcgagc tcgggtcac tcactaccgc      360
ttctccatct cgtgggcgcg agtgctcccc aatggcagcg cgggcgtccc caaccgcgag     420
gggctgcgct actaccggcg cctgctggag cggctgcggg agctgggcgt gcagcccgtg     480
gtcaccctgt accactggga cctgcccag cgcctgcagg acgcctacgg cggctgggcc      540
aaccgcgccc tggccgacca cttcagggat tacgcggagc tctgcttccg ccacttcggc     600
ggtcaggtca agtactggat caccatcnnn aaccccctacg tggtggcctg gcacggctac   660
gccaccgggc gcctggcccc cggcatccgg ggcagcccgc ggctcgggta cctggtggcg     720
cacaacctcc tcctggctca tgccaaagtc tggcatctct acaatacttc tttccgtccc     780
actcaggag gtcaggtgtc cattgcccta agctctcact ggatcaatcc tcgaagaatg     840
accgaccaca gcatcaaaga atgtcaaaaa tctctggact ttgtactagg ttggtttgcc     900
aaacccgtat ttattgatgg tgactatccc gagagcatga agaataaccct ttcatctatt     960
ctgcctgatt ttactgaatc tgagaaaaag ttcatcaaag gaactgctga cttttttgct    1020
cttttgctttg gacccacctt gagttttcaa cttttggacc ctcacatgaa gttccgccaa    1080
ttggaatctc ccaacctgag gcaactgctt tcctggattg accttgaatt taaccatcct    1140
caaatattta ttgtggaaaa tggctggttt gtctcaggga ccaccaagag agatgatgcc    1200
aaatatatgt attacctcaa aaagttcatc atggaaacct aaaagccat caagctggat    1260
ggggtggatg tcatcgggta taccgcatgg tccctcatgg atggtttcga gtggcacaga    1320
ggttacagca tcaggcgtgg actcttctat gttgactttc taagccagga caagatgttg    1380
ttgccaaagt cttcagcctt gttctaccaa aagctgatag agaaaaatgg cttccctcct    1440
ttacctgaaa atcagcccct agaagggaca tttcctgtg actttgcttg gggagttgtt    1500
gacaactaca ttcaagtaag tcagctgaca aaaccaatca gcagtctcac caagccctat    1560
cac                                                                  1563
```

<210> SEQ ID NO 70
<211> LENGTH: 1548
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (613)..(615)
<223> OTHER INFORMATION: n is a, c, g, or t

<400> SEQUENCE: 70

```
gagccgggcg acggcgcgca gacctgggcc cgtgtctcgc ggcctcctgc ccccgaggcc      60
gcgggcctct tccagggcac cttccccgac ggcttcctct gggccgtggg cagcgccgcc    120
taccagaccg agggcggctg gcagcagcac ggcaagggtg cgtccatctg ggacacgttc    180
acccaccacc ccctgcaccc ccggggagac tcccggaacg ccagtctgcc gttgggcgcc    240
ccgtcgccgc tgcagcccgc caccggggac gtagccagcg acagctacaa caacgtcttc    300
```

```
cgcgacacgg aggcgctgcg cgagctcggg gtcactcact accgcttctc catctcgtgg    360
gcgcgagtgc tccccaatgg cagcgcgggc gtccccaacc gcgaggggct gcgctactac    420
cggcgcctgc tggagcggct gcgggagctg ggcgtgcagc ccgtggtcac cctgtaccac    480
tgggacctgc cccagcgcct gcaggacgcc tacggcggct gggccaaccg cgccctggcc    540
gaccacttca gggattacgc ggagctctgc ttccgccact tcggcggtca ggtcaagtac    600
tggatcacca tcnnnaaccc ctacgtggtg gcctggcacg gctacgccac cgggcgcctg    660
gcccccggca tccggggcag cccgcggctc gggtacctgg tggcgcacaa cctcctcctg    720
gctcatgcca aagtctggca tctctacaat acttctttcc gtcccactca gggaggtcag    780
gtgtccattg ccctaagctc tcactggatc aatcctcgaa gaatgaccga ccacagcatc    840
aaagaatgtc aaaatctct ggactttgta ctaggttggt ttgccaaacc cgtatttatt    900
gatggtgact atcccgagag catgaagaat aacctttcat ctattctgcc tgattttact    960
gaatctgaga aaaagttcat caaaggaact gctgactttt ttgctctttg ctttggaccc   1020
accttgagtt ttcaactttt ggaccctcac atgaagttcc gccaattgga atctcccaac   1080
ctgaggcaac tgctttcctg gattgacctt gaatttaacc atcctcaaat atttattgtg   1140
gaaaatggct ggtttgtctc agggaccacc aagagagatg atgccaaata tatgtattac   1200
ctcaaaaagt tcatcatgga aaccttaaaa gccatcaagc tggatggggt ggatgtcatc   1260
gggtataccg catggtccct catggatggt ttcgagtggc acagaggtta cagcatcagg   1320
cgtggactct tctatgttga cttctaagc caggacaaga tgttgttgcc aaagtcttca   1380
gccttgttct accaaaagct gatagagaaa aatggcttcc ctcctttacc tgaaaatcag   1440
cccctagaag ggacatttcc ctgtgacttt gcttggggag ttgttgacaa ctacattcaa   1500
gtaagtcagc tgacaaaacc aatcagcagt ctcaccaagc cctatcac                1548
```

<210> SEQ ID NO 71
<211> LENGTH: 3036
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (1240)..(1242)
<223> OTHER INFORMATION: n is a, c, g, or t

<400> SEQUENCE: 71

```
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag   120
acctgggccc gtgtctcgcg gcctcctgcc ccgaggccg cgggcctctt ccagggcacc    180
ttccccgacg gcttcctctg ggccgtgggc agcgccgcct accagaccga gggcggctgg   240
cagcagcacg gcaagggtgc gtccatctgg gacacgttca cccaccaccc cctggcaccc   300
ccgggagact cccggaacgc cagtctgccg ttgggcgccc cgtcgccgct gcagcccgcc   360
accggggacg tagccagcga cagctacaac aacgtcttcc gcgacacgga ggcgctgcgc   420
gagctcgggg tcactcacta ccgcttctcc atctcgtggg cgcgagtgct ccccaatggc   480
agcgcgggcg tccccaaccg cgaggggctg cgctactacc ggcgcctgct ggagcggctg   540
```

```
cgggagctgg gcgtgcagcc cgtggtcacc ctgtaccact gggacctgcc ccagcgcctg    600
caggacgcct acggcggctg ggccaaccgc gccctggccg accacttcag ggattacgcg    660
gagctctgct tccgccactt cggcggtcag gtcaagtact ggatcaccat cnnnaacccc    720
tacgtggtgg cctggcacgg ctacgccacc gggcgcctgg ccccggcat ccggggcagc     780
ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaaatctctg     960
gactttgtac taggttggtt tgccaaaccc gtatttattg atggtgacta tcccgagagc   1020
atgaagaata acctttcatc tattctgcct gattttactg aatctgagaa aaagttcatc   1080
aaaggaactg ctgactttt tgctctttgc tttggaccca ccttgagttt tcaacttttg    1140
gaccctcaca tgaagttccg ccaattggaa tctcccaacc tgaggcaact gctttcctgg   1200
attgaccttg aatttaacca tcctcaaata tttattgtgn nnaatggctg gtttgtctca   1260
gggaccacca agagagatga tgccaaatat atgtattacc tcaaaaagtt catcatggaa   1320
accttaaaag ccatcaagct ggatggggtg gatgtcatcg gtataccgc atggtccctc    1380
atggatggtt tcgagtggca cagaggttac agcatcaggc gtggactctt ctatgttgac   1440
tttctaagcc aggacaagat gttgttgcca aagtcttcag ccttgttcta ccaaaagctg   1500
atagagaaaa atggcttccc tcctttacct gaaaatcagc ccctagaagg gactttccc    1560
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatgggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtggccct gtggcagcct   1920
atggccccga accaaggact gccgcgcctc ctggccaggc agggcgcctg ggagaacccc   1980
tacactgccc tggcctttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg ggaaaatatc catagccttg caggctgatt ggatagaacc tgcctgccct   2220
ttctcccaaa aggacaaaga ggtggccgag agagttttgg aatttgacat tggctggctg   2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggctttaag ccattatacc accatccttg tagactcaga aaaagaagat   2460
ccaataaaat acaatgatta cctagaagtg caagaaatga ccgacatcac gtggctcaac   2520
tcccccagtc aggtggcggt agtgccctgg gggttgcgca aagtgctgaa ctggctgaag   2580
ttcaagtacg agacctcccc catgtacata atatccaacg gaatcgatga cgggctgcat   2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagatc agtttgagcc caaggcatcc   2820
atgaaacatt acaggaaaat tattgacagc aatggtttcc cggcccaga aactctggaa     2880
agattttgtc cagaagaatt caccgtgtgt actgagtgca gttttttca cacccgaaag    2940
```

```
tctttactgg ctttcatagc ttttctattt tttgcttcta ttatttctct ctcccttata    3000
ttttactact cgaagaaagg cagaagaagt tacaaa                              3036

<210> SEQ ID NO 72
<211> LENGTH: 2949
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (625)..(627)
<223> OTHER INFORMATION: n is a, c, g, or t
<220> FEATURE:
<221> NAME/KEY: misc_feature
<222> LOCATION: (1153)..(1155)
<223> OTHER INFORMATION: n is a, c, g, or t

<400> SEQUENCE: 72
cgcctgcgtg cggagccggg cgacggcgcg cagacctggg cccgtgtctc gcggcctcct      60
gcccccgagg ccgcgggcct cttccagggc accttccccg acggcttcct ctgggccgtg     120
ggcagcgccg cctaccagac cgagggcggc tggcagcagc acggcaaggg tgcgtccatc     180
tgggacacgt tcacccacca cccctggca ccccgggag actcccggaa cgccagtctg       240
ccgttgggcg ccccgtcgcc gctgcagccc gccaccgggg acgtagccag cgacagctac     300
aacaacgtct tccgcgacac ggaggcgctg cgcgagctcg gggtcactca ctaccgcttc     360
tccatctcgt gggcgcgagt gctccccaat ggcagcgcgg gcgtcccca ccgcgagggg      420 ctgcgctact accggcgcct gctggagcgg ctgcgggagc tgggcgtgca gcccgtggtc     480
accctgtacc actgggacct gccccagcgc ctgcaggacg cctacggcgg ctgggccaac     540
cgcgccctgg ccgaccactt cagggattac gcggagctct gcttccgcca cttcggcggt     600
caggtcaagt actggatcac catcnnnaac ccctacgtgg tggcctggca cggctacgcc     660
accgggcgcc tggccccccgg catccggggc agcccgcggc tcgggtacct ggtggcgcac   720
aacctcctcc tggctcatgc caaagtctgg catctctaca atacttcttt ccgtcccact     780
cagggaggtc aggtgtccat tgccctaagc tctcactgga tcaatcctcg aagaatgacc     840
gaccacagca tcaaagaatg tcaaaaatct ctggactttg tactaggttg gtttgccaaa     900
cccgtattta ttgatggtga ctatcccgag agcatgaaga taaccttc atctattctg       960 cctgatttta ctgaatctga gaaaagttc atcaaggaa ctgctgactt ttttgctctt      1020
tgctttggac ccaccttgag ttttcaactt ttggacctc acatgaagtt ccgccaattg    1080
gaatctccca acctgaggca actgctttcc tggattgacc ttgaatttaa ccatcctcaa    1140
atatttattg tgnnnaatgg ctggtttgtc tcagggacca ccaagagaga tgatgccaaa    1200
tatatgtatt acctcaaaaa gttcatcatg gaaaccttaa aagccatcaa gctggatggg    1260
gtggatgtca tcgggtatac cgcatggtcc ctcatggatg gtttcgagtg cacagaggt    1320 tacagcatca ggcgtggact cttctatgtt gactttctaa gccaggacaa gatgttgttg    1380
ccaaagtctt cagccttgtt ctaccaaaag ctgatagaga aaatggctt ccctccttta    1440 cctgaaaatc agcccctaga agggacattt ccctgtgact tgcttgggg agttgttgac    1500 aactacattc aagtagatac cactctgtct cagtttaccg acctgaatgt ttacctgtgg    1560
gatgtccacc acagtaaaag gcttattaaa gtggatgggg ttgtgaccaa gaagaggaaa    1620
tcctactgtg ttgactttgc tgccatccag ccccagatcg ctttactcca ggaaatgcac    1680
```

| gttacacatt | ttcgcttctc | cctggactgg | gccctgattc | tccctctggg | taaccagtcc | 1740 |
| gttacacatt | ttcgcttctc | cctggactgg | gccctgattc | tccctctggg | taaccagtcc | 1740 |

```
gttacacatt ttcgcttctc cctggactgg gccctgattc tccctctggg taaccagtcc  1740
caggtgaacc acaccatcct gcagtactat cgctgcatgg ccagcgagct tgtccgtgtc  1800
aacatcaccc cagtggtggc cctgtggcag cctatggccc cgaaccaagg actgccgcgc  1860
ctcctggcca ggcagggcgc ctgggagaac ccctacactg ccctggcctt tgcagagtat  1920
gcccgactgt gctttcaaga gctcggccat cacgtcaagc tttggataac gatgaatgag  1980
ccgtatacaa ggaatatgac atacagtgct ggccacaacc ttctgaaggc ccatgccctg  2040
gcttggcatg tgtacaatga aaagtttagg catgctcaga atgggaaaat atccatagcc  2100
ttgcaggctg attggataga acctgcctgc cctttctccc aaaaggacaa agaggtggcc  2160
gagagagttt tggaatttga cattggctgg ctggctgagc ccattttcgg ctctggagat  2220
tatccatggg tgatgaggga ctggctgaac caaagaaaca attttcttct tccttatttc  2280
actgaagatg aaaaaaagct aatccagggt acctttgact ttttggcttt aagccattat  2340
accaccatcc ttgtagactc agaaaaagaa gatccaataa aatacaatga ttacctagaa  2400
gtgcaagaaa tgaccgacat cacgtggctc aactccccca gtcaggtggc ggtagtgccc  2460
tgggggttgc gcaaagtgct gaactggctg aagttcaagt acggagacct ccccatgtac  2520
ataatatcca acggaatcga tgacgggctg catgctgagg acgaccagct gagggtgtat  2580
tatatgcaga attacataaa cgaagctctc aaagcccaca tactggatgg tatcaatctt  2640
tgcggatact ttgcttattc gtttaacgac cgcacagctc cgaggtttgg cctctatcgt  2700
tatgctgcag atcagtttga gcccaaggca tccatgaaac attacaggaa aattattgac  2760
agcaatggtt tcccgggccc agaaactctg gaaagatttt gtccagaaga attcaccgtg  2820
tgtactgagt gcagtttttt tcacacccga aagtctttac tggctttcat agcttttcta  2880
ttttttgctt ctattatttc tctctcccct atatttttact actcgaagaa aggcagaaga  2940
agttacaaa                                                         2949
```

<210> SEQ ID NO 73
<211> LENGTH: 2940
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (1240)..(1242)
<223> OTHER INFORMATION: n is a, c, g, or t

<400> SEQUENCE: 73

```
atgcccgcca gcgccccgcc gcgccgcccg cggccgccgc cgccgtcgct gtcgctgctg   60
ctggtgctgc tgggcctggg cggccgccgc ctgcgtgcgg agccgggcga cggcgcgcag  120
acctgggccc gtgtctcgcg gcctcctgcc cccgaggccg cgggcctctt ccagggcacc  180
ttccccgacg gcttcctctg ggccgtgggc agcgccgcct accagaccga gggcggctgg  240
cagcagcacg gcaagggtgc gtccatctgg gacacgttca cccaccaccc cctgcaccc   300 ccgggagact cccggaacgc cagtctgccg ttgggcgccc cgtcgccgct gcagcccgcc  360
accggggacg tagccagcga cagctacaac aacgtcttcc gcgacacgga ggcgctgcgc  420
gagctcgggg tcactcacta ccgcttctcc atctcgtggg cgcgagtgct ccccaatggc  480
agcgcgggcg tccccaaccg cgaggggctg cgctactacc ggcgcctgct ggagcggctg  540
```

```
cgggagctgg gcgtgcagcc cgtggtcacc ctgtaccact gggacctgcc ccagcgcctg      600
caggacgcct acggcggctg ggccaaccgc gccctggccg accacttcag ggattacgcg      660
gagctctgct tccgccactt cggcggtcag gtcaagtact ggatcaccat cnnnaacccc      720
tacgtggtgg cctggcacgg ctacgccacc gggcgcctgg cccccggcat ccggggcagc      780
ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca agaatgtca aaaatctctg      960 gactttgtac taggttggtt tgccaaaccc gtatttattg atggtgacta tcccgagagc     1020
atgaagaata accttcatc tattctgcct gattttactg aatctgagaa aaagttcatc     1080
aaaggaactg ctgactttt tgctctttgc tttggaccca ccttgagttt tcaacttttg     1140
gaccctcaca tgaagttccg ccaattggaa tctcccaacc tgaggcaact gctttcctgg     1200
attgaccttg aatttaacca tcctcaaata tttattgtgn nnaatggctg gtttgtctca     1260
gggaccacca agagagatga tgccaaatat atgtattacc tcaaaaagtt catcatggaa     1320
accttaaaag ccatcaagct ggatggggtg gatgtcatcg gtataccgc atggtccctc     1380 atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tccttacct gaaaatcagc ccctagaagg gacatttccc     1560
tgtgactttg cttggggagt tgttgacaac tacattcaag tagataccac tctgtctcag     1620
tttaccgacc tgaatgttta cctgtgggat gtccaccaca gtaaaaggct tattaaagtg     1680
gatggggttg tgaccaagaa gaggaaatcc tactgtgttg actttgctgc catccagccc     1740
cagatcgctt tactccagga aatgcacgtt acacattttc gcttctccct ggactgggcc     1800
ctgattctcc ctctgggtaa ccagtcccag gtgaaccaca ccatcctgca gtactatcgc     1860
tgcatggcca gcgagcttgt ccgtgtcaac atcacccag tggtggccct gtggcagcct     1920
atggccccga accaaggact gccgcgcctc ctggccaggc agggcgcctg ggagaaccc     1980 tacactgccc tggcctttgc agagtatgcc cgactgtgct tcaagagct cggccatcac     2040 gtcaagcttt ggataacgat gaatgagccg tatacaagga atatgacata cagtgctggc     2100
cacaaccttc tgaaggccca tgccctggct tggcatgtgt acaatgaaaa gtttaggcat     2160
gctcagaatg ggaaaatatc catagccttg caggctgatt ggatagaacc tgcctgccct     2220
ttctcccaaa aggacaaaga ggtggccgag agagttttgg aatttgacat tggctggctg     2280
gctgagccca ttttcggctc tggagattat ccatgggtga tgagggactg gctgaaccaa     2340
agaaacaatt ttcttcttcc ttatttcact gaagatgaaa aaaagctaat ccagggtacc     2400
tttgactttt tggctttaag ccattatacc accatccttg tagactcaga aaagaagat     2460 ccaataaaat acaatgatta cctagaagtg caagaaatga ccgacatcac gtggctcaac     2520
tcccccagtc aggtggcggt agtgcctgg gggttgcgca agtgctgaa ctggctgaag     2580 ttcaagtacg gagacctccc catgtacata atatccaacg gaatcgatga cgggctgcat     2640
gctgaggacg accagctgag ggtgtattat atgcagaatt acataaacga agctctcaaa     2700
gcccacatac tggatggtat caatctttgc ggatactttg cttattcgtt taacgaccgc     2760
acagctccga ggtttggcct ctatcgttat gctgcagatc agtttgagcc caaggcatcc     2820
atgaaacatt acaggaaaat tattgacagc aatggtttcc cgggcccaga aactctggaa     2880
```

```
agattttgtc cagaagaatt caccgtgtgt actgagtgca gttttttca cacccgaaag    2940
```

<210> SEQ ID NO 74
<211> LENGTH: 2857
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (629)..(631)
<223> OTHER INFORMATION: n is a, c, g, or t
<220> FEATURE:
<221> NAME/KEY: misc_feature
<222> LOCATION: (1157)..(1159)
<223> OTHER INFORMATION: n is a, c, g, or t

<400> SEQUENCE: 74

```
ccgccgcctg cgtgcggagc cgggcgacgg cgcgcagacc tgggcccgtg tctcgcggcc      60
tcctgccccc gaggccgcgg gcctcttcca gggcaccttc cccgacggct tcctctgggc     120
cgtgggcagc gccgcctacc agaccagggg cggctggcag cagcacggca agggtgcgtc     180
catctgggac acgttcaccc accacccct ggcaccccg ggagactccc ggaacgccag      240
tctgccgttg ggcgccccgt cgccgctgca gcccgccacc ggggacgtag ccagcgacag    300
ctacaacaac gtcttccgcg cacggaggc gctgcgcgag ctcggggtca ctcactaccg     360
cttctccatc tcgtgggcgc gagtgctccc caatggcagc gcgggcgtcc caaccgcga     420
ggggctgcgc tactaccggc gcctgctgga gcggctgcgg gagctgggcg tgcagcccgt    480
ggtcaccctg taccactggg acctgcccca gcgcctgcag gacgcctacg gcggctgggc    540
caaccgcgcc ctggccgacc acttcaggga ttacgcggag ctctgcttcc gccacttcgg    600
cggtcaggtc aagtactgga tcaccatcnn naacccctac gtggtggcct ggcacggcta    660
cgccaccggg cgcctggccc ccggcatccg gggcagcccg cggctcgggt acctggtggc    720
gcacaacctc ctcctggctc atgccaaagt ctggcatctc tacaatactt ctttccgtcc    780
cactcaggga ggtcaggtgt ccattgccct aagctctcac tggatcaatc ctcgaagaat    840
gaccgaccac agcatcaaag aatgtcaaaa atctctggac tttgtactag ttggtttgc     900
caaacccgta tttattgatg gtgactatcc cgagagcatg aagaataacc tttcatctat    960
tctgcctgat tttactgaat ctgagaaaaa gttcatcaaa ggaactgctg acttttttgc   1020
tctttgcttt ggacccacct tgagttttca acttttggac cctcacatga gttccgcca    1080
attggaatct cccaacctga ggcaactgct ttcctggatt gaccttgaat ttaaccatcc   1140
tcaaatattt attgtgnnna atggctggtt tgtctcaggg accaccaaga gagatgatgc   1200
caaatatatg tattacctca aaagttcat catggaaacc ttaaaagcca tcaagctgga    1260
tggggtggat gtcatcgggt ataccgcatg gtccctcatg gatggtttcg agtggcacag    1320
aggttacagc atcaggcgtg gactcttcta tgttgactt ctaagccagg acaagatgtt    1380
gttgccaaag tcttcagcct tgttctacca aaagctgata gagaaaaatg gcttccctcc    1440
tttacctgaa aatcagcccc tagaagggac atttccctgt gactttgctt ggggagttgt   1500
tgacaactac attcaagtag ataccactct gtctcagttt accgacctga atgtttacct    1560
gtgggatgtc caccacagta aaaggcttat taaagtggat ggggttgtga ccaagaagag    1620
gaaatcctac tgtgttgact tgctgccat ccagccccag atcgcttac tccaggaaat    1680
gcacgttaca cattttcgct ctcccctgga ctggccctg attctcccct cgggtaacca    1740
gtcccaggtg aaccacacca tcctgcagta ctatcgctgc atggccagcg agcttgtccg    1800
```

```
tgtcaacatc accccagtgg tggccctgtg gcagcctatg gccccgaacc aaggactgcc    1860
gcgcctcctg gccaggcagg gcgcctggga gaacccctac actgccctgg cctttgcaga    1920
gtatgcccga ctgtgctttc aagagctcgg ccatcacgtc aagctttgga taacgatgaa    1980
tgagccgtat acaaggaata tgacatacag tgctggccac aaccttctga aggcccatgc    2040
cctggcttgg catgtgtaca atgaaaagtt taggcatgct cagaatggga aaatatccat    2100
agccttgcag gctgattgga tagaacctgc ctgcccttc tcccaaaagg acaagaggt     2160 ggccgagaga gttttggaat ttgacattgg ctggctggct gagcccattt tcggctctgg    2220
agattatcca tgggtgatga gggactggct gaaccaaaga aacaattttc ttcttcctta    2280
tttcactgaa gatgaaaaaa agctaatcca gggtaccttt gacttttgg ctttaagcca     2340 ttataccacc atccttgtag actcagaaaa agaagatcca ataaaataca atgattacct    2400
agaagtgcaa gaaatgaccg acatcacgtg gctcaactcc cccagtcagg tggcggtagt    2460
gccctggggg ttgcgcaaag tgctgaactg gctgaagttc aagtacggag acctccccat    2520
gtacataata tccaacggaa tcgatgacgg gctgcatgct gaggacgacc agctgagggt    2580
gtattatatg cagaattaca taaacgaagc tctcaaagcc cacatactgg atggtatcaa    2640
tctttgcgga tactttgctt attcgtttaa cgaccgcaca gctccgaggt ttggcctcta    2700
tcgttatgct gcagatcagt ttgagcccaa ggcatccatg aaacattaca ggaaaattat    2760
tgacagcaat ggtttccgg gcccagaaac tctggaaaga ttttgtccag aagaattcac     2820
cgtgtgtact gagtgcagtt tttttcacac ccgaaag                             2857
```

<210> SEQ ID NO 75
<211> LENGTH: 1704
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (1240)..(1242)
<223> OTHER INFORMATION: n is a, c, g, or t

<400> SEQUENCE: 75

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtgtctcgcg gcctcctgcc cccgaggccg cgggcctctt ccagggcacc    180
ttccccgacg gcttcctctg ggccgtgggc agcgccgcct accagaccga ggcggctgg     240 cagcagcacg gcaagggtgc gtccatctgg gacacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acggcggctg gccaaccgc gccctggccg accacttcag ggattacgcg     660
gagctctgct tccgccactt cggcggtcag gtcaagtact ggatcaccat cnnnaaccc     720
```

| | |
|---|---:|
| tacgtggtgg cctggcacgg ctacgccacc gggcgcctgg cccccggcat ccggggcagc | 780 |
| ccgcggctcg ggtacctggt ggcgcacaac ctcctcctgg ctcatgccaa agtctggcat | 840 |
| ctctacaata cttctttccg tcccactcag ggaggtcagg tgtccattgc cctaagctct | 900 |
| cactggatca atcctcgaag aatgaccgac cacagcatca aagaatgtca aaaatctctg | 960 |
| gactttgtac taggttggtt tgccaaaccc gtatttattg atggtgacta tcccgagagc | 1020 |
| atgaagaata acctttcatc tattctgcct gattttactg aatctgagaa aaagttcatc | 1080 |
| aaaggaactg ctgactttt tgctctttgc tttggaccca ccttgagttt tcaacttttg | 1140 |
| gaccctcaca tgaagttccg ccaattggaa tctcccaacc tgaggcaact gctttcctgg | 1200 |
| attgaccttg aatttaacca tcctcaaata tttattgtgn nnaatggctg gtttgtctca | 1260 |
| gggaccacca agagagatga tgccaaatat atgtattacc tcaaaaagtt catcatggaa | 1320 |
| accttaaaag ccatcaagct ggatggggtg gatgtcatcg ggtataccgc atggtccctc | 1380 |
| atggatggtt tcgagtggca cagaggttac agcatcaggc gtggactctt ctatgttgac | 1440 |
| tttctaagcc aggacaagat gttgttgcca aagtcttcag ccttgttcta ccaaaagctg | 1500 |
| atagagaaaa atggcttccc tcctttacct gaaaatcagc ccctagaagg gacatttccc | 1560 |
| tgtgactttg cttggggagt tgttgacaac tacattcaag tagataccac tctgtctcag | 1620 |
| tttaccgacc tgaatgttta cctgtgggat gtccaccaca gtaaaaggct tattaaagtg | 1680 |
| gatggggttg tgaccaagaa gagg | 1704 |

<210> SEQ ID NO 76
<211> LENGTH: 1621
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (629)..(631)
<223> OTHER INFORMATION: n is a, c, g, or t
<220> FEATURE:
<221> NAME/KEY: misc_feature
<222> LOCATION: (1157)..(1159)
<223> OTHER INFORMATION: n is a, c, g, or t

<400> SEQUENCE: 76

| | |
|---|---:|
| ccgccgcctg cgtgcggagc cgggcgacgg cgcgcagacc tgggcccgtg tctcgcggcc | 60 |
| tcctgccccc gaggccgcgg gcctcttcca gggcaccttc cccgacggct tcctctgggc | 120 |
| cgtgggcagc gccgcctacc agaccgaggg cggctggcag cagcacggca aggtgcgtc | 180 |
| catctgggac acgttcaccc accaccccct ggcaccccg ggagactccc ggaacgccag | 240 |
| tctgccgttg ggcgccccgt cgccgctgca gcccgccacc ggggacgtag ccagcgacag | 300 |
| ctacaacaac gtcttccgcg acacggaggc gctgcgcgag ctcggggtca ctcactaccg | 360 |
| cttctccatc tcgtgggcgc gagtgctccc caatggcagc gcgggcgtcc caaccgcga | 420 |
| ggggctgcgc tactaccggc gcctgctgga gcggctgcgg gagctgggcg tgcagcccgt | 480 |
| ggtcacccctg taccactggg acctgcccca gcgcctgcag gacgcctacg gcggctgggc | 540 |
| caaccgcgcc ctggccgacc acttcaggga ttacgcggag ctctgcttcc gccacttcgg | 600 |
| cggtcaggtc aagtactgga tcaccatcnn naaccctac gtggtggcct ggcacggcta | 660 |
| cgccaccggg cgcctggccc ccggcatccg gggcagcccg cggctcgggt acctggtggc | 720 |
| gcacaacctc ctcctggctc atgccaaagt ctggcatctc tacaatactt ctttccgtcc | 780 |
| cactcaggga ggtcaggtgt ccattgccct aagctctcac tggatcaatc ctcgaagaat | 840 |

```
gaccgaccac agcatcaaag aatgtcaaaa atctctggac tttgtactag gttggtttgc    900
caaacccgta tttattgatg gtgactatcc cgagagcatg aagaataacc tttcatctat    960
tctgcctgat tttactgaat ctgagaaaaa gttcatcaaa ggaactgctg acttttttgc   1020
tctttgcttt ggaccacct tgagttttca acttttggac cctcacatga agttccgcca    1080
attggaatct cccaacctga ggcaactgct ttcctggatt gaccttgaat ttaaccatcc   1140
tcaaatattt attgtgnnna atggctggtt tgtctcaggg accaccaaga gagatgatgc   1200
caaatatatg tattacctca aaaagttcat catggaaacc ttaaaagcca tcaagctgga   1260
tggggtggat gtcatcgggt ataccgcatg gtccctcatg gatggtttcg agtggcacag   1320
aggttacagc atcaggcgtg gactcttcta tgttgacttt ctaagccagg acaagatgtt   1380
gttgccaaag tcttcagcct tgttctacca aaagctgata gagaaaaatg cttccctcc    1440 tttacctgaa aatcagcccc tagaagggac atttccctgt gactttgctt ggggagttgt   1500
tgacaactac attcaagtag ataccactct gtctcagttt accgacctga atgtttacct   1560
gtgggatgtc caccacagta aaaggcttat taaagtggat ggggttgtga ccaagaagag   1620
g                                                                   1621

<210> SEQ ID NO 77
<211> LENGTH: 1548
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (613)..(615)
<223> OTHER INFORMATION: n is a, c, g, or t
<220> FEATURE:
<221> NAME/KEY: misc_feature
<222> LOCATION: (1141)..(1143)
<223> OTHER INFORMATION: n is a, c, g, or t

<400> SEQUENCE: 77
gagccgggcg acggcgcgca gacctgggcc cgtgtctcgc ggcctcctgc ccccgaggcc     60
gcgggcctct tccagggcac cttccccgac ggcttcctct gggccgtggg cagcgccgcc    120
taccagaccg agggcggctg gcagcagcac ggcaagggtg cgtccatctg ggacacgttc    180
acccaccacc ccctggcacc cccggggagac tcccggaacg ccagtctgcc gttgggcgcc    240
ccgtcgccgc tgcagcccgc caccggggac gtagccagcg acagctacaa caacgtcttc    300
cgcgacacgg aggcgctgcg cgagctcggg gtcactcact accgcttctc catctcgtgg    360
gcgcgagtgc tccccaatgg cagcgcgggc gtccccaacc gcgaggggct gcgctactac    420
cggcgcctgc tggagcggct gcgggagctg gcgtgcagc ccgtggtcac cctgtaccac    480
tgggacctgc cccagcgcct gcaggacgcc tacgcggct gggccaaccg cgccctggcc    540
gaccacttca gggattacgc ggagctctgc ttccgcact cggcggtca ggtcaagtac     600 tggatcacca tcnnnaaccc ctacgtggtg gcctggcacg gctacgccac cgggcgcctg    660
gcccccggca tccggggcag cccgcggctc gggtacctgg tggcgcacaa cctcctcctg    720
gctcatgcca aagtctggca tctctacaat acttcttcc gtcccactca gggaggtcag    780
gtgtccattg ccctaagctc tcactggatc aatcctcgaa gaatgaccga ccacagcatc    840
aaagaatgtc aaaatctct ggactttgta ctaggttggt ttgccaaacc cgtatttatt     900
gatggtgact atcccgagag catgaagaat aacctttcat ctattctgcc tgattttact    960
```

```
gaatctgaga aaaagttcat caaaggaact gctgactttt ttgctctttg ctttggaccc    1020
accttgagtt ttcaactttt ggaccctcac atgaagttcc gccaattgga atctcccaac    1080
ctgaggcaac tgctttcctg gattgacctt gaatttaacc atcctcaaat atttattgtg    1140
nnnaatggct ggtttgtctc agggaccacc aagagagatg atgccaaata tatgtattac    1200
ctcaaaaagt tcatcatgga aaccttaaaa gccatcaagc tggatggggt ggatgtcatc    1260
gggtataccg catggtccct catggatggt ttcgagtggc acagaggtta cagcatcagg    1320
cgtggactct tctatgttga ctttctaagc caggacaaga tgttgttgcc aaagtcttca    1380
gccttgttct accaaaagct gatagagaaa aatggcttcc ctcctttacc tgaaaatcag    1440
cccctagaag ggacatttcc ctgtgacttt gcttgggag ttgttgacaa ctacattcaa    1500
gtagatacca ctctgtctca gtttaccgac ctgaatgttt acctgtgg               1548
```

<210> SEQ ID NO 78
<211> LENGTH: 1647
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (1240)..(1242)
<223> OTHER INFORMATION: n is a, c, g, or t

<400> SEQUENCE: 78

```
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag   120
acctgggccc gtgtctcgcg gcctcctgcc cccgaggccg cgggcctctt ccagggcacc   180
ttccccgacg gcttcctctg ggccgtgggc agcgccgcct accagaccga gggcggctgg   240
cagcagcacg gcaagggtgc gtccatctgg gacacgttca cccaccaccc cctggcaccc   300
ccgggagact cccggaacgc cagtctgccg ttgggcgccc cgtcgccgct gcagcccgcc   360
accggggacg tagccagcga cagctacaac aacgtcttcc gcgacacgga ggcgctgcgc   420
gagctcgggg tcactcacta ccgcttctcc atctcgtggg cgcgagtgct ccccaatggc   480
agcgcgggcg tccccaaccg cgaggggctg cgctactacc ggcgcctgct ggagcggctg   540
cgggagctgg gcgtgcagcc cgtggtcacc ctgtaccact gggacctgcc ccagcgcctg   600
caggacgcct acggcggctg ggccaaccgc gccctggccg accacttcag ggattacgcg   660
gagctctgct ccgccacttt cggcggtcag gtcaagtact ggatcaccat cnnnaacccc    720
tacgtggtgg cctggcacgg ctacgccacc gggcgcctgg ccccggcat ccggggcagc    780 ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaatctctg     960 gactttgtac taggttggtt tgccaaaccc gtatttatg atggtgacta tcccgagagc   1020
atgaagaata acctttcatc tattctgcct gattttactg aatctgagaa aaagttcatc   1080
aaaggaactg ctgactttt tgctctttgc tttggaccca ccttgagttt tcaacttttg   1140
gaccctcaca tgaagttccg ccaattggaa tctcccaacc tgaggcaact gctttcctgg   1200
attgaccttg aatttaacca tcctcaaata tttattgtgn nnaatggctg gtttgtctca   1260
```

```
gggaccacca agagagatga tgccaaatat atgtattacc tcaaaaagtt catcatggaa    1320
accttaaaag ccatcaagct ggatggggtg gatgtcatcg gtataccgc atggtccctc    1380 atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tcctttacct gaaaatcagc ccctagaagg gacatttccc    1560
tgtgactttg cttggggagt tgttgacaac tacattcaag taagtcagct gacaaaacca    1620
atcagcagtc tcaccaagcc ctatcac                                       1647
```

<210> SEQ ID NO 79
<211> LENGTH: 1563
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (628)..(630)
<223> OTHER INFORMATION: n is a, c, g, or t
<220> FEATURE:
<221> NAME/KEY: misc_feature
<222> LOCATION: (1156)..(1158)
<223> OTHER INFORMATION: n is a, c, g, or t

<400> SEQUENCE: 79

```
cgccgcctgc gtgcggagcc gggcgacggc gcgcagacct gggcccgtgt ctcgcggcct    60 cctgccccg aggccgcggg cctcttccag ggcaccttcc ccgacggctt cctctgggcc    120
gtgggcagcg ccgcctacca gaccgagggc ggctggcaga agcacggcaa gggtgcgtcc    180
atctgggaca cgttcaccca ccaccccctg gcaccccgg gagactcccg gaacgccagt    240
ctgccgttgg gcgccccgtc gccgctgcag cccgccaccg gggacgtagc cagcgacagc    300
tacaacaacg tcttccgcga cacggaggcg ctgcgcgagc tcggggtcac tcactaccgc    360
ttctccatct cgtgggcgcg agtgctcccc aatggcagcg cgggcgtccc caaccgcgag    420
gggctgcgct actaccggcg cctgctggag cggctgcggg agctgggcgt gcagcccgtg    480
gtcaccctgt accactggga cctgcccag cgcctgcagg acgcctacgg cggctgggcc    540
aaccgcgccc tggccgacca cttcagggat tacgcggagc tctgcttccg ccacttcggc    600
ggtcaggtca agtactggat caccatcnnn aaccctacg tggtggcctg gcacggctac    660
gccaccgggc gcctggcccc cggcatccgg ggcagcccgc ggctcgggta cctggtggcg    720
cacaacctcc tcctggctca tgccaaagtc tggcatctct acaatacttc tttccgtccc    780
actcagggag tcaggtgtc cattgcccta agctctcact ggatcaatcc tcgaagaatg    840
accgaccaca gcatcaaaga atgtcaaaaa tctctggact ttgtactagg ttggtttgcc    900
aaacccgtat ttattgatgg tgactatccc gagagcatga agaataaccct ttcatctatt    960 ctgcctgatt ttactgaatc tgagaaaaag ttcatcaaag gaactgctga cttttttgct    1020
ctttgctttg gacccacctt gagttttcaa cttttggacc ctcacatgaa gttccgccaa    1080
ttggaatctc ccaacctgag gcaactgctt tcctggattg accttgaatt taaccatcct    1140 caaatatttta ttgtgnnnaa tggctggttt gtctcaggga ccaccaagag agatgatgcc    1200
aaatatatgt attacctcaa aaagttcatc atggaaaccct taaaagccat caagctggat    1260
ggggtggatg tcatcgggta taccgcatgg tccctcatgg atggtttcga gtggcacaga    1320
ggttacagca tcaggcgtgg actcttctat gttgactttc taagccagga caagatgttg    1380
```

```
ttgccaaagt cttcagcctt gttctaccaa aagctgatag agaaaaatgg cttccctcct    1440
ttacctgaaa atcagcccct agaagggaca tttccctgtg actttgcttg gggagttgtt    1500
gacaactaca ttcaagtaag tcagctgaca aaaccaatca gcagtctcac caagccctat    1560
cac                                                                  1563
```

<210> SEQ ID NO 80
<211> LENGTH: 1548
<212> TYPE: DNA
<213> ORGANISM: Artificial
<220> FEATURE:
<223> OTHER INFORMATION: DNA encoding recombinant variant polypeptide
<220> FEATURE:
<221> NAME/KEY: misc_feature
<222> LOCATION: (613)..(615)
<223> OTHER INFORMATION: n is a, c, g, or t
<220> FEATURE:
<221> NAME/KEY: misc_feature
<222> LOCATION: (1141)..(1143)
<223> OTHER INFORMATION: n is a, c, g, or t

<400> SEQUENCE: 80

```
gagccgggcg acggcgcgca gacctgggcc cgtgtctcgc ggcctcctgc ccccgaggcc     60
gcgggcctct tccagggcac cttccccgac ggcttcctct gggccgtggg cagcgccgcc    120
taccagaccg agggcggctg gcagcagcac ggcaagggtg cgtccatctg ggacacgttc    180
acccaccacc ccctggcacc cccgggagac tcccggaacg ccagtctgcc gttgggcgcc    240
ccgtcgccgc tgcagcccgc caccggggac gtagccagcg acagctacaa caacgtcttc    300
cgcgacacgg aggcgctgcg cgagctcggg gtcactcact accgcttctc catctcgtgg    360
gcgcgagtgc tccccaatgg cagcgcgggc gtccccaacc gcgaggggct gcgctactac    420
cggcgcctgc tggagcggct gcgggagctg gcgtgcagc ccgtggtcac cctgtaccac    480
tgggacctgc cccagcgcct gcaggacgcc tacgcggct gggccaaccg cgccctggcc    540
gaccacttca gggattacgc ggagctctgc ttccgccact cggcggtca ggtcaagtac    600 tggatcacca tcnnnaaccc ctacgtggtg gcctggcacg gctacgccac cgggcgcctg    660
gcccccggca tccggggcag cccgcggctc gggtacctgg tggcgcacaa cctcctcctg    720
gctcatgcca aagtctggca tctctacaat acttcttcc gtcccactca gggaggtcag    780
gtgtccattg ccctaagctc tcactggatc aatcctcgaa gaatgaccga ccacagcatc    840
aaagaatgtc aaaaatctct ggactttgta ctaggttggt ttgccaaacc cgtatttatt    900
gatggtgact atcccgagag catgaagaat aacctttcat ctattctgcc tgattttact    960
gaatctgaga aaaagttcat caaaggaact gctgactttt ttgctctttg ctttggaccc   1020
accttgagtt ttcaactttt ggaccctcac atgaagttcc gccaattgga atctcccaac   1080
ctgaggcaac tgctttcctg gattgacctt gaatttaacc atcctcaaat atttattgtg   1140
nnnaatggct ggtttgtctc agggaccacc aagagagatg atgccaaata tatgtattac   1200
ctcaaaaagt tcatcatgga aaccttaaaa gccatcaagc tggatggggt ggatgtcatc   1260
gggtataccg catggtccct catggatggt ttcgagtggc acagaggtta cagcatcagg   1320
cgtggactct tctatgttga ctttctaagc caggacaaga tgttgttgcc aaagtcttca   1380
gccttgttct accaaaagct gatagagaaa aatggcttcc ctcctttacc tgaaaatcag   1440
cccctagaag ggacatttcc ctgtgacttt gcttggggag ttgttgacaa ctacattcaa   1500
gtaagtcagc tgacaaaaacc aatcagcagt ctcaccaagc cctatcac                1548
```

-continued

```
<210> SEQ ID NO 81
<211> LENGTH: 1014
<212> TYPE: PRT
<213> ORGANISM: Mouse
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 81

Met Leu Ala Arg Ala Pro Pro Arg Arg Pro Arg Leu Val Leu Leu
1               5                   10                  15

Arg Leu Leu Leu Leu His Leu Leu Leu Ala Leu Arg Ala Arg Cys
            20                  25                  30

Leu Ser Ala Glu Pro Gly Gln Gly Ala Gln Thr Trp Ala Arg Phe Ala
            35                  40                  45

Arg Ala Pro Ala Pro Glu Ala Ala Gly Leu Leu His Asp Thr Phe Pro
        50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Leu Ser Ser Thr Gly Asp Val Ala Ser
            115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
    210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
    290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
```

|   | 355 |   |   |   | 360 |   |   |   | 365 |   |   |
|---|---|---|---|---|---|---|---|---|---|---|---|

Phe Ala Leu Ser Phe Gly Pro Thr Leu Ser Phe Gln Leu Leu Asp Pro
370 375 380

Asn Met Lys Phe Arg Gln Leu Glu Ser Pro Asn Leu Arg Gln Leu Leu
385 390 395 400

Ser Trp Ile Asp Leu Glu Tyr Asn His Pro Pro Ile Phe Ile Val Glu
405 410 415

Asn Gly Trp Phe Val Ser Gly Thr Thr Lys Arg Asp Asp Ala Lys Tyr
420 425 430

Met Tyr Tyr Leu Lys Lys Phe Ile Met Glu Thr Leu Lys Ala Ile Arg
435 440 445

Leu Asp Gly Val Asp Val Ile Gly Tyr Thr Ala Trp Ser Leu Met Asp
450 455 460

Gly Phe Glu Trp His Arg Gly Tyr Ser Ile Arg Arg Gly Leu Phe Tyr
465 470 475 480

Val Asp Phe Leu Ser Gln Asp Lys Glu Leu Leu Pro Lys Ser Ser Ala
485 490 495

Leu Phe Tyr Gln Lys Leu Ile Glu Asp Asn Gly Phe Pro Pro Leu Pro
500 505 510

Glu Asn Gln Pro Leu Glu Gly Thr Phe Pro Cys Asp Phe Ala Trp Gly
515 520 525

Val Val Asp Asn Tyr Val Gln Val Asp Thr Thr Leu Ser Gln Phe Thr
530 535 540

Asp Pro Asn Val Tyr Leu Trp Asp Val His His Ser Lys Arg Leu Ile
545 550 555 560

Lys Val Asp Gly Val Val Ala Lys Lys Arg Lys Pro Tyr Cys Val Asp
565 570 575

Phe Ser Ala Ile Arg Pro Gln Ile Thr Leu Leu Arg Glu Met Arg Val
580 585 590

Thr His Phe Arg Phe Ser Leu Asp Trp Ala Leu Ile Leu Pro Leu Gly
595 600 605

Asn Gln Thr Gln Val Asn His Thr Val Leu His Phe Tyr Arg Cys Met
610 615 620

Ile Ser Glu Leu Val His Ala Asn Ile Thr Pro Val Val Ala Leu Trp
625 630 635 640

Gln Pro Ala Ala Pro His Gln Gly Leu Pro His Ala Leu Ala Lys His
645 650 655

Gly Ala Trp Glu Asn Pro His Thr Ala Leu Ala Phe Ala Asp Tyr Ala
660 665 670

Asn Leu Cys Phe Lys Glu Leu Gly His Trp Val Asn Leu Trp Ile Thr
675 680 685

Met Asn Glu Pro Asn Thr Arg Asn Met Thr Tyr Arg Ala Gly His His
690 695 700

Leu Leu Arg Ala His Ala Leu Ala Trp His Leu Tyr Asp Asp Lys Phe
705 710 715 720

Arg Ala Ala Gln Lys Gly Lys Ile Ser Ile Ala Leu Gln Ala Asp Trp
725 730 735

Ile Glu Pro Ala Cys Pro Phe Ser Gln Asn Asp Lys Glu Val Ala Glu
740 745 750

Arg Val Leu Glu Phe Asp Ile Gly Trp Leu Ala Glu Pro Ile Phe Gly
755 760 765

Ser Gly Asp Tyr Pro Arg Val Met Arg Asp Trp Leu Asn Gln Lys Asn
770 775 780

-continued

Asn Phe Leu Leu Pro Tyr Phe Thr Glu Asp Glu Lys Leu Val Arg
785                 790                 795                 800

Gly Ser Phe Asp Phe Leu Ala Val Ser His Tyr Thr Thr Ile Leu Val
                805                 810                 815

Asp Trp Glu Lys Glu Asp Pro Met Lys Tyr Asn Asp Tyr Leu Glu Val
            820                 825                 830

Gln Glu Met Thr Asp Ile Thr Trp Leu Asn Ser Pro Ser Gln Val Ala
        835                 840                 845

Val Val Pro Trp Gly Leu Arg Lys Val Leu Asn Trp Leu Arg Phe Lys
850                 855                 860

Tyr Gly Asp Leu Pro Met Tyr Val Thr Ala Asn Gly Ile Asp Asp Asp
865                 870                 875                 880

Pro His Ala Glu Gln Asp Ser Leu Arg Ile Tyr Tyr Ile Lys Asn Tyr
                885                 890                 895

Val Asn Glu Ala Leu Lys Ala Tyr Val Leu Asp Asp Ile Asn Leu Cys
            900                 905                 910

Gly Tyr Phe Ala Tyr Ser Leu Ser Asp Arg Ser Ala Pro Lys Ser Gly
        915                 920                 925

Phe Tyr Arg Tyr Ala Ala Asn Gln Phe Glu Pro Lys Pro Ser Met Lys
930                 935                 940

His Tyr Arg Arg Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
            980                 985                 990

Phe Thr Phe Ile Ile Ser Leu Ala Leu Ile Phe His Tyr Ser Lys Lys
        995                 1000                1005

Gly Gln Arg Ser Tyr Lys
    1010

<210> SEQ ID NO 82
<211> LENGTH: 550
<212> TYPE: PRT
<213> ORGANISM: Mouse
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 82

Met Leu Ala Arg Ala Pro Pro Arg Arg Pro Pro Arg Leu Val Leu Leu
1               5                   10                  15

Arg Leu Leu Leu Leu His Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

```
Ser Gly Ala Pro Ser Pro Leu Ser Ser Thr Gly Asp Val Ala Ser
        115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
                180                 185                 190

Leu Tyr His Trp Asp Leu Pro Gln Arg Leu Gln Asp Thr Tyr Gly Gly
                195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
                260                 265                 270

Leu Leu Leu Ala His Ala Lys Val Trp His Leu Tyr Asn Thr Ser Phe
                275                 280                 285

Arg Pro Thr Gln Gly Gly Arg Val Ser Ile Ala Leu Ser Ser His Trp
                290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
                340                 345                 350

Asp Phe Thr Glu Ser Glu Lys Arg Leu Ile Arg Gly Thr Ala Asp Phe
                355                 360                 365

Phe Ala Leu Cys Phe Gly Pro Thr Leu Ser Phe Gln Leu Leu Asp Pro
                370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
                420                 425                 430

Met Tyr Tyr Leu Lys Lys Phe Ile Met Glu Thr Leu Lys Ala Ile Arg
                435                 440                 445

Leu Asp Gly Val Asp Val Ile Gly Tyr Thr Ala Trp Ser Leu Met Asp
                450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
                500                 505                 510

Glu Asn Gln Pro Leu Glu Gly Thr Phe Pro Cys Asp Phe Ala Trp Gly
                515                 520                 525
```

Val Val Asp Asn Tyr Val Gln Val Ser Pro Leu Thr Lys Pro Ser Val
    530                 535                 540

Gly Leu Leu Leu Pro His
545                 550

<210> SEQ ID NO 83
<211> LENGTH: 5032
<212> TYPE: DNA
<213> ORGANISM: Mouse
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 83

```
cctcccggct cccgcagcat gctagcccgc gcccctcctc gccgcccgcc gcggctggtg      60
ctgctccgtt tgctgttgct gcatctgctg ctgctcgccc tgcgcgcccg ctgcctgagc     120
gctgagccgg tcagggcgc gcagacctgg gctcgcttcg cgcgcgctcc tgccccagag     180
gccgctggcc tcctccacga caccttcccc gacggtttcc tctgggcggt aggcagcgcc     240
gcctatcaga ccgagggcgg ctggcgacag cacggcaaag gcgcgtccat ctgggacact     300
ttcacccatc actctggggc ggccccgtcc gactccccga tcgtcgtggc gccgtcgggt     360
gccccgtcgc ctcccctgtc ctccactgga gatgtggcca gcgatagtta caacaacgtc     420
taccgcgaca cagagggct gcgcgaactg ggggtcaccc actaccgctt ctccatatcg     480
tgggcgcggt tgctccccaa tggcaccgcg ggcactccca accgcagggg gctgcgctac     540
taccggcggc tgctggagcg gctgcgggag ctgggcgtgc agccggtggt tacccctgtac     600
cattgggacc tgccacagcg cctgcaggac acctatggcg gatgggccaa tcgcgccctg     660
gccgaccatt tcagggatta tgccgagctc tgcttccgcc acttcggtgg tcaggtcaag     720
tactggatca ccattgacaa cccctacgtg gtggcctggc acgggtatgc caccgggcgc     780
ctggccccgg gcgtgagggg cagctccagg ctcgggtacc tggttgccca caacctactt     840
ttggctcatg ccaaagtctg gcatctctac aacacctctt ccgcccac acagggaggc      900
cgggtgtcta tcgccttaag ctcccattgg atcaatcctc gaagaatgac tgactataat     960
atcagagaat gccagaagtc tcttgacttt gtgctaggct ggtttgccaa acccatattt    1020
attgatggcg actacccaga gagtatgaag acaacctct cgtctcttct gcctgatttt    1080
actgaatctg agaagaggct catcagagga actgctgact tttttgctct ctccttcgga    1140
ccaaccttga gctttcagct attggaccct aacatgaagt tccgccaatt ggagtctccc    1200
aacctgaggc agcttctgtc ttggatagat ctggaatata accacccctcc aatatttatt    1260
gtggaaaatg gctggtttgt ctcgggaacc accaaaaggg atgatgccaa atatatgtat    1320
tatctcaaga agttcataat ggaaacctta aaagcaatca gactggatgg ggtcgacgtc    1380
attgggtaca ccgcgtggtc gctcatggac ggtttcgagt ggcataggg ctacagcatc     1440
cggcgaggac tcttctacgt tgactttctg agtcaggaca aggagctgtt gccaaagtct    1500
tcggccttgt tctaccaaaa gctgatagag acaatggct tcctcctttt acctgaaaac    1560
cagcccttg aagggacatt tccctgtgac tttgcttggg gagttgttga caactacgtt     1620
caagtggaca ctactctctc tcagtttact gacccgaatg tctatctgtg ggatgtgcat    1680
cacagtaaga ggcttattaa agtagacggg gttgtagcca agaagagaaa accttactgt    1740
gttgatttct ctgccatccg gcctcagata accttacttc gagaaatgcg ggtcacccac    1800
```

```
tttcgcttct ccctggactg ggccctgatc ttgcctctgg gtaaccagac ccaagtgaac    1860
cacacggttc tgcacttcta ccgctgcatg atcagcgagc tggtgcacgc caacatcact    1920
ccagtggtgg ccctgtggca gccagcagcc ccgcaccaag gcctgccaca tgcccttgca    1980
aaacatgggg cctgggagaa cccgcacact gctctggcgt ttgcagacta cgcaaacctg    2040
tgttttaaag agttgggtca ctgggtcaat ctctggatca ccatgaacga gccaaacaca    2100
cggaacatga cctatcgtgc cgggcaccac ctcctgagag cccatgcctt ggcttggcat    2160
ctgtacgatg acaagtttag ggcggctcag aaaggcaaaa tatccatcgc cttgcaggct    2220
gactggatag aaccggcctg ccctttctct caaaatgaca agaagtggc cgagagagtt    2280
ttggaatttg atataggctg gctggcagag cctattttg gttccggaga ttatccacgt    2340
gtgatgaggg actggctgaa ccaaaaaaac aattttcttt tgccctattt caccgaagat    2400
gaaaaaagc tagtccgggg ttcctttgac ttcctggcgg tgagtcatta caccaccatt    2460
ctggtagact gggaaaagga ggatccgatg aaatacaacg attacttgga ggtacaggag    2520
atgactgaca tcacatggct caactctccc agtcaggtgg cagtggtgcc ttggggctg    2580
cgcaaagtgc tcaactggct aaggttcaag tacggagacc tcccgatgta tgtgacagcc    2640
aatgaatcg atgatgaccc ccacgccgag caagactcac tgaggatcta ttatattaag    2700
aattatgtga atgaggctct gaaagcctac gtgttggacg acatcaacct ttgtggctac    2760
tttgcgtatt cacttagtga tcgctcagct cccaagtctg gcttttatcg atatgctgcg    2820
aatcagtttg agcccaaacc atctatgaaa cattacagga gaattattga cagcaatggc    2880
ttcctgggtt ctggaacact gggaaggttt tgtccagaag aatacactgt gtgcaccgaa    2940
tgtggatttt ttcaaacccg gaagtctttg ctggtcttca tctcgtttct tgtttttact    3000
tttattattt ctcttgctct cattttcac tactccaaga aaggccagag aagttataag    3060
taatgtgaac gtctgcctgg ccattcgctt tgggatcaag atgtacacgc cgtcagccgt    3120
ttgcacctct ctgtgttgtg agccgcattc cacacatttc gattctagaa aacccttttt    3180
gtcatgggtg gtagaggttt aaacaggaa ttggtgagaa taaaatattg cagggtgaat    3240
ggtatctgaa tctgctctct ttggtggcaa ttacggaatt atactcacca cagtttctac    3300
agtgccccgg aatggaaggc atagaatacg gtagggataa cagtgccaag cagacagaag    3360
tttaaagaac aactttaggg acttgtttat ccatggccat ttttaaattc actcctgttg    3420
gggagtaaca ctctctcaat taccatctta acacctggac tttacctgat ccagttttac    3480
aaggtgaagt agaaaaatat ccagtaaagg tggccaagag ccctgagtcc agagcagccc    3540
attaagaagc actattccta ccaaatgctg ctaatgtcaa tttacaaata tacttagaaa    3600
gcacattatg gacatttgta ttcttgtgaa tgttttgag gtgtgcccta accccagat     3660
ccttgagggc tttctcttac caactttcct ttcagagcct gcttgttgga gattcttccc    3720
cagcccctt ccccttttccc tcttgctctg ccccacctcg ctccacccag cttgctccag    3780
cccaaagatt ctttatttgt ttctcattac cgaaggttgt gagccaccat gtggtttctg    3840
ggatttgaac tcatgacctc cggaggagct gtcatgctct taaccagccc atgttgaaga    3900
ttcttttgat aaatattcac aaaaaataaa gatgagccat gagctgttgg cctcttcgga    3960
agcggaaact gagtgatttg attgaacatc cttttatctt tgaccagacc ttggaatgaa    4020
tgcaatgacc tttcccacag gaagaaggag gagctctcag tcaaactgta aagaatgcct    4080
cttcagaata tgctgtcagt gcttggatgc catgatgttc aactttctta gtcgatccgg    4140
cagcaatcac agtgtgagca cactgggaac ctgtccttgc ggccgccgag atctaccgtg    4200
```

```
tgcttctgtg aagaggcttt gacgtagccc ctctttgagc tcttacacca tgctactgac    4260
ttctagaaag gctaattagg tcttcttcta cacctaatac cctaagtctt actgactctc    4320
acgggagaag tctctgtgct acacctgagt ggtcttattg ataaccctga taccagatca    4380
ggcaagataa atccgtcata gcaggcatgg ctacccttgc tgccacaggg tcacagcaca    4440
tagctcatca ccctgttatt cttcatcttg caatgtggta tggttttcct ggtgaatgat    4500
cagcttttgc tgtggtattc tttatacatc tggacttatt attgaaatca aatgctatag    4560
aatcaatagt ttattttatg tctattttc ttgatcgcag agtaatatat attaattgta    4620
aaaaatttaa gaaacaaaaa ctatatgtaa agaaaaaatt ataatataat acagagatgc    4680
tgctgacagt tcctatgtgt tgtgttttgt atactgagat catgtgatac gtaggcatac    4740
atcttcttgg gttttttttgt ttttgttttt tgttttgttt tgttttgttt tggttttttg    4800
agatagggtt tctctgtata gccctggctg tcctggaact cactttgcag accaggctag    4860
cctcaaactc ttattcattt ttactgaagt aattttctg tcattagtct tcaagagcaa    4920
aactttaata gttatggaga atattgccag aacagctcaa aactgtttta tttgttggtc    4980
caatttccca ttaattagtt caataataaa tatcatttag aaataaaaaa aa           5032
```

<210> SEQ ID NO 84
<211> LENGTH: 1650
<212> TYPE: DNA
<213> ORGANISM: Mouse
<300> PUBLICATION INFORMATION:
<302> TITLE: Polypeptide, novel DNA and novel antibody
<310> PATENT DOCUMENT NUMBER: US6579850
<311> PATENT FILING DATE: 1999-06-25
<312> PUBLICATION DATE: 2003-06-17

<400> SEQUENCE: 84

```
atgctagccc gcgcccctcc tcgccgcccg ccgcggctgg tgctgctccg tttgctgttg      60
ctgcatctgc tgctgctcgc cctgcgcgcc cgctgcctga gcgctgagcc gggtcagggc     120
gcgcagacct gggctcgctt cgcgcgcgct cctgccccag aggccgctgg cctcctccac     180
gacaccttcc ccgacggttt tcctctgggcg gtaggcagcg ccgcctatca gaccgagggc    240
ggctggcgac agcacggcaa aggcgcgtcc atctgggaca ctttcaccca tcactctggg    300
gcggccccgt ccgactcccc gatcgtcgtg gcgccgtcgg gtgccccgtc gcctcccctg    360
tcctccactg gagatgtggc cagcgatagt tacaacaacg tctaccgcga cacagagggg    420
ctgcgcgaac tggggtcac ccactaccgc ttctccatat cgtgggcgcg ggtgctcccc     480
aatggcaccg cgggcactcc caaccgcgag gggctgcgct actaccggcg gctgctggag    540
cggctgcggg agctgggcgt gcagccggtg gttaccctgt accattggga cctgccacag    600
cgcctgcagg acacctatgg cggatgggcc aatcgcgccc tggccgacca tttcagggat    660
tatgccgagc tctgcttccg ccacttcggt ggtcaggtca agtactggat caccattgac    720 aaccctacg tggtggcctg gcacgggtat gccaccgggc gcctggcccc gggcgtgagg    780
ggcagctcca ggctcgggta cctggttgcc cacaacctac ttttggctca tgccaaagtc    840
tggcatctct acaacacctc tttccgcccc acacagggag gcgggtgtc tatcgcctta    900 agctcccatt ggatcaatcc tcgaagaatg actgactata atatcagaga atgccagaag    960
tctcttgact ttgtgctagg ctggtttgcc aaacccatat ttattgatgg cgactaccca   1020
gagagtatga agaacaacct ctcgtctctt ctgcctgatt ttactgaatc tgagaagagg   1080
ctcatcagag gaactgctga cttttttgct ctctgcttcg gaccaacctt gagctttcag   1140
```

```
ctattggacc ctaacatgaa gttccgccaa ttggagtctc ccaacctgag gcagcttcts    1200
tcttggatag atctggaata taaccaccct ccaatattta ttgtggaaaa tggctggttt    1260
gtctcgggaa ccaccaaaag ggatgatgcc aaatatatgt attatctcaa gaagttcata    1320
atggaaacct taaaagcaat cagactggat ggggtcgacg tcattgggta caccgcgtgg    1380
tcgctcatgg acggtttcga gtggcatagg ggctacagca tccggcgagg actcttctac    1440
gttgactttc tgagtcagga caaggagctg ttgccaaagt cttcggcctt gttctaccaa    1500
aagctgatag aggacaatgg ctttcctcct ttacctgaaa accagcccct tgaagggaca    1560
tttccctgtg actttgcttg gggagttgtt gacaactacg tacaagtaag tcctttgaca    1620
aaacccagtg tcggcctctt gcttcctcac                                    1650
```

<210> SEQ ID NO 85
<211> LENGTH: 411
<212> TYPE: PRT
<213> ORGANISM: Homo sapiens

<400> SEQUENCE: 85

```
Lys Ser Tyr Cys Val Asp Phe Ala Ala Ile Gln Pro Gln Ile Ala Leu
1               5                   10                  15

Leu Gln Glu Met His Val Thr His Phe Arg Phe Ser Leu Asp Trp Ala
            20                  25                  30

Leu Ile Leu Pro Leu Gly Asn Gln Ser Gln Val Asn His Thr Ile Leu
        35                  40                  45

Gln Tyr Tyr Arg Cys Met Ala Ser Glu Leu Val Arg Val Asn Ile Thr
    50                  55                  60

Pro Val Val Ala Leu Trp Gln Pro Met Ala Pro Asn Gln Gly Leu Pro
65                  70                  75                  80

Arg Leu Leu Ala Arg Gln Gly Ala Trp Glu Asn Pro Tyr Thr Ala Leu
                85                  90                  95

Ala Phe Ala Glu Tyr Ala Arg Leu Cys Phe Gln Glu Leu Gly His His
            100                 105                 110

Val Lys Leu Trp Ile Thr Met Asn Glu Pro Tyr Thr Arg Asn Met Thr
        115                 120                 125

Tyr Ser Ala Gly His Asn Leu Leu Lys Ala His Ala Leu Ala Trp His
    130                 135                 140

Val Tyr Asn Glu Lys Phe Arg His Ala Gln Asn Gly Lys Ile Ser Ile
145                 150                 155                 160

Ala Leu Gln Ala Asp Trp Ile Glu Pro Ala Cys Pro Phe Ser Gln Lys
                165                 170                 175

Asp Lys Glu Val Ala Glu Arg Val Leu Glu Phe Asp Ile Gly Trp Leu
            180                 185                 190

Ala Glu Pro Ile Phe Gly Ser Gly Asp Tyr Pro Trp Val Met Arg Asp
        195                 200                 205

Trp Leu Asn Gln Arg Asn Asn Phe Leu Leu Pro Tyr Phe Thr Glu Asp
    210                 215                 220

Glu Lys Lys Leu Ile Gln Gly Thr Phe Asp Phe Leu Ala Leu Ser His
225                 230                 235                 240

Tyr Thr Thr Ile Leu Val Asp Ser Glu Lys Glu Asp Pro Ile Lys Tyr
                245                 250                 255

Asn Asp Tyr Leu Glu Val Gln Glu Met Thr Asp Ile Thr Trp Leu Asn
            260                 265                 270

Ser Pro Ser Gln Val Ala Val Pro Trp Gly Leu Arg Lys Val Leu
        275                 280                 285
```

```
Asn Trp Leu Lys Phe Lys Tyr Gly Asp Leu Pro Met Tyr Ile Ile Ser
    290             295                 300

Asn Gly Ile Asp Asp Gly Leu His Ala Glu Asp Asp Gln Leu Arg Val
305             310              315                 320

Tyr Tyr Met Gln Asn Tyr Ile Asn Glu Ala Leu Lys Ala His Ile Leu
            325                 330                 335

Asp Gly Ile Asn Leu Cys Gly Tyr Phe Ala Tyr Ser Phe Asn Asp Arg
            340              345             350

Thr Ala Pro Arg Phe Gly Leu Tyr Arg Tyr Ala Ala Asp Gln Phe Glu
        355             360             365

Pro Lys Ala Ser Met Lys His Tyr Arg Lys Ile Ile Asp Ser Asn Gly
    370             375             380

Phe Pro Gly Pro Glu Thr Leu Glu Arg Phe Cys Pro Glu Glu Phe Thr
385             390             395             400

Val Cys Thr Glu Cys Ser Phe Phe His Thr Arg
            405             410
```